United States Patent [19]
Randall et al.

[11] Patent Number: 6,143,561
[45] Date of Patent: Nov. 7, 2000

[54] DNA ENCODING PLASTID PYRUVATE DEHYDROGENASE AND BRANCHED CHAIN OXOACID DEHYDROGENASE COMPONENTS

[75] Inventors: Douglas D. Randall; Brian P. Mooney, both of Columbia, Mo.; Mark L. Johnston, Gales Ferry; Michael H. Luethy, Old Mystic, both of Conn.; Jan A. Miernyk, Peoria, Ill.

[73] Assignee: The Curators of the University of Missouri, Columbia, Mo.

[21] Appl. No.: 09/108,020

[22] Filed: Jun. 30, 1998

Related U.S. Application Data

[60] Provisional application No. 60/051,291, Jun. 30, 1997, provisional application No. 60/055,255, Aug. 1, 1997, provisional application No. 60/076,544, Mar. 2, 1998, and provisional application No. 60/076,554, Mar. 2, 1998.

[51] Int. Cl.$^7$ .............................. C12N 1/21; C12N 5/14; C12N 15/29; C12N 15/52; C12N 15/82
[52] U.S. Cl. .................. 435/419; 435/252.3; 435/320.1; 536/23.2; 536/23.6
[58] Field of Search ................................ 435/69.1, 320.1, 435/419, 468, 252.3; 536/23.2, 23.6; 800/278, 298

[56] References Cited

FOREIGN PATENT DOCUMENTS

| | | |
|---|---|---|
| WO9219747 | 11/1992 | WIPO . |
| WO9302187 | 2/1993 | WIPO . |
| WO 95/04150 | 2/1995 | WIPO . |
| WO9505472 | 2/1995 | WIPO . |
| WO9800557 | 1/1997 | WIPO . |

OTHER PUBLICATIONS

Hahn, J. J., et al., "Growth Kinetcs, Nutrient Uptake, and Expression of the *Alcaligenes eutrophus* Poly(β–hydroxybutyrate) Synthesis Pathway in Transgenic Maize Cell Suspension Cultures," *Biotechnol. Prog.*, 13, pp. 347–354, 1997.
Johnston, Mark L., et al., "Cloning and molecular analyses of the *Arabidopsis thaliana* plastid pyruvate dehydrogenase subunits," *Biochimica et Biophysica Acta*, 1321, pp. 200–206, 1997.
Lee, Sang Yup, "Plastic bacteria? Progress and prospects for polyhydroxyalkanoate production in bacteria," *Tibtech*, vol. 14, pp. 431–438, Nov. 1996.
Luethy, Michael H., et al., "The nucleotide and deduced amino acid sequences of a cDNA encoding the E1β–subunti of the *Arabidopsis thaliana* mitochondrial pyruvate dehydrogenase complex," *Biochimca et Biophysica Acta*, 1187, pp. 95–98, 1994.
Luethy, Michael H., et al., "The mitochondrial pyruvate dehydrogenase complex: nucleotide and deduced amino–acid sequences of a cDNA encoding the *Arabidopsis thaliana* E1α–subunit," *Gene*, 164, pp. 251–254, 1995.
Luethy, M. H., et al., "Plant pyruvate dehydrogenase complexes" In M.S. Patel et al., Eds., *Alpha–Keto Acid Dehydrogenase Complexes*, Birkhauser Verlag, Basel, Switzerland, pp. 71–92, 1996.
Luethy, Michael H., et al., "The Nucleotide Sequence Of A cDNA Encoding The E1–beta Subunit Of The Branched–Chain Alpha–Keto Acid Dehydrogenase From *Arabidopsis thaliana*," Plant Gene Register PGR 98–133, *Plant Physiol.*, 118:329, 1998.
Mooney, Brian P., et al., "Nucleotide sequence of a cDNA encoding the dihydrolipoylacyltransferase E2) subunit of the branched–chain alpha–keto acid dehydrogenase complex from *Arabidopsis thaliana*," Plant Gene Register PGR 98–071, *Plant Physiol.*, 117:331, 1998.
Poirier, Yves, et al., "Polyhydroxybutyrate, a Biodegradable Thermoplastic, Produced in Transgenic Plants," *Science*, vol. 256, pp. 520–523, Apr. 24, 1992.
Poirier, Yves, et al., "Production of Polyhydroxyalkanoates, a Family of Biodegradable Plastics and Elastomers, in Bacteria and Plants," *Bio/Technology*, vol. 13, pp. 142–150, Feb. 13, 1995.
Guan, Y., et al., "Cloning and Characterization of a Dihydrolipoamide Acetyltransferase (E2) subunit of the Pyruvate Dehydrogenase Complex from *Arabidopsis thaliana*," *Journal of Biological Chemistry*, vol. 270, No. 10, 1995, pp. 5412–5417.
Johnston, M. L., et al., "Cloning and molecular analyses of the *Arabidopsis thaliana* plastid pyruvate dehydrogenase subunits," *Plant Biology '97: 1997 Annual Meetings of the American Society of Plant Physiologists and the Canadian Society of Plant Physiologists, Japanese Society of Plant Physiologists and the Australian Society of Plant Physiologists*, Vancouver, British Columbia, 1997.
Nawrath, C., et al., "Plastid Targeting of the Enzymes Required for the Production of Polyhydroxybutyrate in Higher Plants," *Biodegradable Plastics and Polymers*, Y. Doi et al., Eds., Elsevier Science B.V., 1994, pp. 136–149.
Nawrath, C., et al., "Plant polymers for biodegradable plastics: cellulose, starch and polyhydroxyalkanoates," *Molecular Breeding*, vol. 1, No. 2, 1995, pp. 105–122.
Newman, T., et al., "EST AC T04217," *EMBL Database*, Aug. 30, 1993, Heidelberg.
Newman, T., et al., "EST AC T42996," *EMBL Database*, Feb. 3, 1995, Heidelberg.
Newman, T., et al., "EST AC R29966," *EMBL Database*, Aug. 11, 1995, Heidelberg.
Newman, T., et al., "EST AC N65566," *EMBL Database*, Mar. 8, 1996, Heidelberg.
Newman, T., et al., "EST AC N96042," *EMBL Database*, Apr. 19, 1996, Heidelberg.
Newman, T., et al., "EST AC W43179," *EMBL Database*, May 27, 1996, Heidelberg.
Stam M, et al. "The silence of genes in transgenic plants." Ann. Bot. 79: 3–12, 1997.
Koziel MG, et al. "Optimizing expression of transgenes with an emphasis on post–transcriptional events." Plant Mol. Biol. 32: 393–405, 1996.
De Luca V. "Molecular characterization of secondary metabolic pathways." Ag. Biotech. 5: 225N–228N, 1993.

*Primary Examiner*—Amy J. Nelson
*Attorney, Agent, or Firm*—Senniger, Powers, Leavitt & Roedel

[57] ABSTRACT

Provided are nucleic acid sequences encoding E1α, E1β, and E2 subunits of plastid pyruvate dehydrogenase complexes and branched chain oxoacid dehydrogenase complexes.

18 Claims, 27 Drawing Sheets

BRANCHED-CHAIN E1α

PLASTID E1α

PLASTID TARGETED BRANCHED-CHAIN E1α CHIMERA

CONSTRUCT 1: ATTACH THE CHLOROPLAST TARGETING PEPTIDE OF E1α TO THE BRANCHED-CHAIN E1α. THIS CREATES A PLASTID TARGETED BRANCHED-CHAIN E1α CHIMERA.

BRANCHED-CHAIN E1β

PLASTID E1β

PLASTID TARGETED BRANCHED-
CHAIN E1β CHIMERA

CONSTRUCT 2: REPLACE THE N-TERMINUS OF
THE BRANCHED-CHAIN E1β (INCLUDING THE E2
BINDING DOMAIN) WITH THE N-TERMINUS OF THE
PLASTID E1β (INCLUDING THE CHLOROPLAST
TARGETING PEPTIDE AND THE PLASTID E2
BINDING DOMAIN). THIS CREATES A PLASTID
TARGETED BRANCHED-CHAIN E1β CHIMERA.

BRANCHED-CHAIN E2

PLASTID E2

PLASTID TARGETED BRANCHED-CHAIN E2

CONSTRUCT 3: ATTACH THE CHLOROPLAST TARGETING PEPTIDE OF THE PLASTID E2 TO THE MATURE PORTION OF THE BRANCHED-CHAIN E2, TO CREATE A PLASTID TARGETED BRANCHED-CHAIN E2 CHIMERA.

CONSTRUCT 4: MEGA PLASMID CODING FOR BOTH CHIMERIC (PLASTID TARGETED BRANCHED-CHAIN) SUBUNITS IF THE PDH. ATTACH THE E1α CHIMERIC SEQUENCE TO THE E1β CHIMERIC SEQUENCE WITH TRANSCRIPTION TERMINATOR AND PROMOTER SEQUENCES BETWEEN THE TWO.

BRANCHED-CHAIN E1β

E2 BINDING DOMAIN     CATALYTIC DOMAIN

PLASTID E1β

CHLOROPLAST TARGETING PEPTIDE

PLASTID TARGETED BRANCHED-CHAIN E1β CHIMERA

CONSTRUCT 5: ATTACH THE CHLOROPLAST TARGETING PEPTIDE OF THE PLASTID E1β TO THE MATURE PORTION OF THE BRANCHED-CHAIN E1β. THIS CREATES A PLASTID TARGETED BRANCHED-CHAIN E1β CHIMERA.

FIGURE 8

```
Plastid A.t.    MATAFAPTKLTATVPLHGSHENRLLLPIRLAPPSSFLGSTRSLSLRRLNH   50
P.purpurea      --------------------------------------------------    
A.thaliana      ------------------MALSRLSSRSNIITRPFSAAFSRLIS          26
H.sapiens II    -----------------MRKMLAAVSRVLSGASQKPASRVLVAS          27
S.cerevisiae    ---MLAASFKRQPSQLVRGLGAVLRTPTRIGHVRTMATLKTTDKKAPEDI    47
A.suum I        ---------------------MIFVFANIFKVPTVSPSVMAISV          23
M.capricolum    ----------------------------------------------MTYL    4
B.subtilis      ------------------------------------MGVKTFQFPFAEQL   14

Consensus       ..................................................   50
```

```
                                                          Motif 1
                SNATRRSPVVSVQEVVKEKQSTNNTSLLITKEEGLELYEDMILGRSFEDM    100
                ----------MSYPKKVELPLTNCNQINLTKHKLLVLYEDMLLGRNFEDM     40
                TDTTPITIETSLPFTAHLCDPPSRSVESSSQELLD-FFRTMALMRRMEIA     75
                RNFANDATFEIKKCDLHRLEEGPPVTTVLTREDGLKYYRMMQTVRRMELK     77
                EGSDTVQIELPESSFESYMLEPPDLSYETSKATLLQMYKDMVIIRRMEMA     97
                RLASTEATFQTKPFKLHKLDSGPDINVHVTKEDAVHYYTQMLTIRRMESA     73
                GKFDPLKNEKVCVLDKDGKVINPKLMPKISDQEILEAYKIMNLSRRQDIY     54
                EKVAEQFPTFQILNEEGEVVNEEAMPELSDEQLKE-LMRRMVYTRILDQR     63

...........................L..Y..M...RR.E..         100
```

```
                          o
                CAQMYYRGKMFGFVHLYNGQEAVSTGFIKLLTKSDSVVSTYRDHVHALSK   150
                CAQMYYKGKMFGFVHLYNGQEAVSTGVIKLLDSKDYVCSTYRDHVHALSK    90
                ADSLYKANVIRGFCHLYDGQEAVAIGMEAAITKKDAIITAYRDHCIFLGR   125
                ADQLYKQKIIRGFCHLCDGQEACCVGLEAGINPTDHLITAYRAHGFTFTR   127
                CDALYKAKKIRGFCHLSVGQEAIAVGIENAITKLDSIITSYRCHGFTFMR   147
                AGNLYKEKKVRGFCHLYSGQEACAVGTKAAMDAGDAAVTAYRCHGWTYLS   123
                QNTMQRQGRLLSFLSSTGQEACEVAYINALNKKTDHFVSGYRNNAAWLAM   104
                SISLNRQGRL-GFYAPTAGQEASQIASHFALEKEDFILPGYRDVPQIIWH   112
```

FIGURE 8

```
...LY......GF.HL..GQEA...G......K.D.....YR.H......      150

TPP-binding site
GVSAR/MSELFGKVTGCCRGQGGSMHMFSKEHNMLGGFAFIGEGIPVAT        200
GVPSQNVMAELFGKETGCSRGRGGSMHIFSAPHNFLGGFAFIAEGIPVAT       140
GGSLHEVFSELMGRQAGCSKGKGGSMHFYKKESSFYGGHGIVGAQVPLGC       175
GLSVREILAELTGRKGGCAKGKGGSMHMYAKN--FYGGNGIVGAQVPLGA       175
GASVKAVLAELMGRRAGVSYGKGGSMHLYAPG--FYGGNGIVGAQVPLGA       195
GSSVAKVLCELTGRITGNVYGKGGSMHMYGEN--FYGGNGIVGAQQPLGT       171
GQLVRNIMLYWIGNEAG-GKAPEG-VNCLPPN-------IVIGSQYSQAT       145
GLPLYQAFLFSRGHFHG-NQIPEG-VNVLPPQ-------IIIGAQYIQAA       153

G.S...V..EL.G...G...G.GGSMH......--F.GG..I.GAQ.P...     200

PDH β binding site
GAAFSSKYRREVLKQDCD-DVTVAFFGDGTCNNGQFFECLNMAALYKLPI       249
GAAFQSIYRQQVLKEPGELRVTACFFGDGTTNNGQFFECLNMAVLWKLPI       190
GIAFAQKYNKE---EA----VTFALYGDGAANQGQLFEALNISALWDLPA       218
GIALACKYNGK---DE----VCLTLYGDGAANQGQIFEAYNMAALWKLPC       218
GLAFAHQYKNE---DA----CSFTLYGDGASNQGQVFESFNMAKLWNLPV       238
GIAFAMKYRKE---KN----VCITMFGDGATNQGQLFESMNMAKLWDLPV       214
GIAFADKYRKT---GG----VVVTTTGDGGSSEGETYEAMNFAKLHEVPC       188
GVALGLKMRGK---KA----VAITYTGDGGTSQGDFYEGINFAGAFKAPA       196

G.AFA.KYR..----..----V..T..GDG..NQGQ.FE..NMA.LW.LP.     250

*3
IFVVENNLWAIGMSHLRATSDPEIWKKGPAFGMPGVHVDGMDVLKVREVA       299
IFVVENNQWAIGMAHHRSSSIPEIHKKAEAFGLPGIEVDGMDVLAVRQVA       240
ILVCENNHYGMGTAEWRAAKSPSYYKRGD-Y-VPGLKVDGMDAFAVKQAC       266
IFICENNRYGMGTSVERAAASTDYYKRGD-F-IPGLRVDGMDILCVREAT       266
VFCCENNKYGMGTAASRSSAMTEYFKRGQ-Y-IPGLKVNGMDILAVYQAS       286
LYVCENNGYGMGTAAARSSASTDYYTRGD-Y-VPGIWVDGMDVLAVRQAV       262
IFVIENNKWAISTARSEQTKSINFAVKGIATGIPSIIVDGNDYLACIGVF       238
IFVVQNNRFAISTPVEKQTVAKTLAQKVAAGIPGIQVDGMDPLAVYAAV        246

IFV.ENN....GTA..R........K.G.....PG..VDGMD.LAV..A.      300

*1        .2
KEAVTRARRGEGPTLVECETYRFRGHSLADPD-ELRDAAE-KAKYAARDP       347
EKAVERARQGQGPTLIEALTYRFRGHSLADPD-ELRSRQE-KEAWVARDP       288
KFAKQHALE-KGPIILEMDTYRHGHSMSDPGSTYRTRDEISGVRQERDP        315
RFAAAYCRSGKGPILMELQTYRYHGHSMSDPGVSYRTREEIQEVRSKSDP       316
KFAKDWCLSGKGPLVLEYETYRYGGHSMSDPGTTYRTRDEIQHMRSKNDP       336
RWAKEWCNAGKGPLMIEMATYRYSGHSMSDPGTSYRTREEVQEVRKTRDP       312
KEVVEYVRKGNGPVLVECDTYRLGAHSSSDNPDAYRPKGEFEEM-AKFDP       287
```

FIGURE 8

```
KAARERAINGEGPTLIETLCFRYGPHTMSGDDPTRYRSKELENEWAKKDP    296

K.A......G.GP.L.E..TYRY.GHSMSDP...YR.R.E........DP   350

IAALKKYLIENKLAKEAELKSIEKKIDELVEEAVEFADASPQPG--RSQL    395
IKKLKKHILDNQIASSDELNDIQSSVKIDLEQSVEFAMSSPEPN--ISEL    336
IERIKKLVLSHDLATEKELKDMEKEIRKEVDDAIAKAKDCPMPE--PSEL    336
IMLLKDRMVNSNLASVEELKEIDVEVRKEIEDAAQFATADPEPP--LEEL    363
IAGLKMHLIDLGIATEAEVKAYDKSARKYVDEQVELADAAPPPEAKLSIL   364
ITGFKDKIVTAGLVTEDEIKEIDKQVRKEIDAAVKQAHTDKESPVELMLT   386
LIRLKQYLIDKKIWSDEQQAQLEAEQDKFVADEFAWVEKNKNYDL-IDIF   362
LVRFRKFLEAKGLWSEEEENNVIEQAKEEIKEAIKKADETPKQK--VTDL   336
                                                   344

I..LK.......LA.E.E.K.......K...A...A...P.P.--...L    400

LENVFADPKGFGIGPDGRYRCEDPKFTEG-TAQV          428
--------K--------RY-----LFADN-----          344
FTNVYV--KGFG---TESFGPDRKEVKAS-LP--          389
GYHIYSSDPPF----EVRGANQWIKFKSVS----          390
FEDVYVKGTETPTLRGRIPEDTWDFKKQGFASRD          420
DIYYNTPAQYVRCTTDEVLQKYLTSEEAVKALAK          396
KYQYDKMDIFLEEQYKEAKEFFEKYPESKEGGHH          370
ISIMFE-ELPF------NLKEQYEIYKEKESK--          369

```
Plastid A.t.   MSSIIHGAGAATTTLSTFNSVDSKKLFVAPSRTNLSVRSQRYIVAGSDAS   50
P.purpurea     --------------------------------------------------
A.thaliana     --------------------------------------------------
H.sapiens      --------------------------------------------------
S.cerevisiae   ----------------------------------------------MFS   3
A.suum         --------------------------------------------------
M.capricolum   --------------------------------------------------
B.subtilis     --------------------------------------------------

Consensus      --------------------------------------------------   50
```

```
               KKSFGSGLRVRHSQKLIPNAVATKEADTSASTGHELLLFEALQEGLEEEM   100
               -------------------------------MSKVFMFDALRAATDEEM    18
               MLGILRQRAIDGASTLRRTRFALVSARSYAAGAKEMTVRDALNSAIDEEM   50
               ---MAAVSGLVRRPLREVSGLLKRRFHWTAPAALQVTVRDAINQGMDEEL   47
               RLPTSLARNVARRAPTSFVRPSAAAAALRFSSTKTMTVREALNSAMAEEL   53
               --MAVNGCMRLLRNGLTSACALEQSVRRLASGTLNVTVRDALNAALDEEI   48
               --------------------------------MAIINNIKAVTDALDCAM   18
               --------------------------------MAQMTMVQAITDALRIEL   18

--............................T...AL..A.DEE.        100
```

```
                           Region 1
               DRDPHVCVMGEDVGHYGGSYKVTKGLADKFGDLRVLDTPICENAFTGMGI   150
               EKDLTVCVIGEDVGHYGGSYKVTKDLHSKYGDLRVLDTPIAENSFTGMAI   68
               SADPKVFVMGEEVGQYQGAYKITKGLLEKYGPERVYDTPITEAGFTGIGV   100
               ERDEKVFLLGEEVAQYDGAYKVSRGLWKKYGDKRIIDTPISEMGFAGIAV   97
               DRDDDVFLIGEEVAQYNGAYKVSKGLLDRFGERRVVDTPITEYGFTGLAV   103
               KRDDRVFLIGEEVAQYDGAYKISKGLWKKYGDGRIWDTPITEMAIAGLSV   98
               QRDPNVIVFGEDVGTEGGVFRATQGLAVKFGNDRCFNAPISEAMFAGVGL   68
               KNDPNVLIFGEDVGVNGGVFRATEGLQAEFGEDRVFDTPLAESGIGGLAI   68

.RD..V...GE.VG.Y.G.YK.TKGL..K.G..RV.DTPI.E..F.G...   150
```

```
               GAAMTGLRPVIEGMNMGFLLLAFNQISNNCGMLHYTSGGQFTIPVVIRGP   200
               GAAITGLRPIVEGMNMSFLLLAFNQISNNAGMLRYTSGGNFTLPLVIRGP   118
               GAAYAGLKPVVEFMTFNFSMQAIDHIINSAAKSNYMSAGQINVPIVFRGP   150
               GAAMAGLRPICEFMTFNFSMQAIDQVINSAAKTYYMSGGLQPVPIVFRGP   147
```

FIGURE 9

```
GAALKGLKPIVEFMSFNFSMQAIDHVVNSAAKTHYMSGGTQKCQMVFRGP 153
GAAMNGLRPICEFMSMNFSMQGIDHIINSAAKAHYMSAGRFHVPIVFRGA 148
GMAMNGMKPVLEMQFEGLGLASLQNIFTNISRMRNRTRGKYTAPMVIRMP 118
GLALQGFRPVPEIQFFGFVYEVMDSICGQMARIRYRTGGRYHMPITIRSP 118

GAA..GLRP..E.M...F...A.D.I.N.AA...Y.SGG....P.V.RGP 200
```

Region 2
```
GGVGRQLGAEHSQRLESYFQSIPGIQMVACSTPYNAKGLMKAAIRSENPV 250
GGVGRQLGAEHSQRLEAYFQAIPGLKIVACSTPYNAKGLLKSAIRDNNPV 168
NGAAAGVGAQHSQCYAAWYASVPGLKVLAPYSAEDARGLLKAAIRDPDPV 200
NGASAGVAAQHSQCFAAWYGHCPGLKVVSPWNSEDAKGLIKSAIRDNNPV 197
NGAAVGLGAQHSQDFSPWYGSIPGLKVLVPYSAEDARGLLKAAIRDPNPV 203
NGAAVGVAQQHSQDFTAWFMHCPGVKVVVPYDCEDARGLLKAAVRDDNPV 198
MGGGIRALEHHSEALEAVYAHIPGVQIVCPSTPYDTKGLILAAIDSPDPV 168
FGGGVHTPELHSDSLEGLVAQQPGLKVVIPSTPYDAKGLLISAIRDNDPV 168

.G......A.HSQ...A.....PGLKVV.P....DAKGLLKAAIRD.NPV 250

ILFEHVLLYN----LKEKIPDEDYICNLEEAEMVRPGEHITILTYSRMRY 296
VFFEHVLLYN----LQEEIPEDEYLIPLDKAEVVRKGKDITILTYSRMRH 214
VFLENELLYGESFPISEEALDSSFCLPIGKAKIEREGKDVTIVTFSKMVG 250
VVLENELMYGVPFEFLPEAQSKDFLIPIGKAKIERQGTHITVVSHSRPVG 247
VFLENELLYGESFEISEEALSPEFTLPY-KAKIEREGTDISIVTYTRNVQ 252
ICLENEILYGMKFPVSPEAQSPDFVLPFGQAKIQRPGKDITIVSLSIGVD 248
IVVEPTKLYR---AFKQEVPDEHYIVPIGEGYKIQEGNDLTVVTYGAQTV 215
IFLEHLKLYR---SFRQEVPEGEYTIPIGKADIKREGKDITIIAYGAMVH 215

..LE..LLY........E........P.GKA.I.R.G.DITIVTYS...V. 300
```

Region 3
```
HVMQAAKTLVNK--GYDPEVIDIRSLKPFDLHTIGNSVKKTHRVLIVEEC 344
HVTEALPLLLND--GYDPEVLDLISLKPLDIDSISVSVKKTHRVLIVEEC 262
FALKAAEKLAEE--GISAEVINLRSIRPLDRATINASVRKTSRLVTVEEG 298
HCLEAAAVLSKE--GVECEVINMRTIRPMDMETIEASVMKTNHLVTVEGG 295
FSLEAAEILQKKY-GVSAEVINLRSIRPLDTEAIIKTVKKTNHLITVEST 301
VSLHAADELAKS--GIDCEVINLRCVRPLDFQTVKDSVIKTKHLVTVESG 296
DCQKAIALLKETHPNATIDLIDLRSIKPWDKKMVIESVKKTGRLLVVHEA 265
ESLKAAAELEKE--GISAEVVDLRTVQPLDIETIIGSVEKTGRAIVVQEA 263

..L.AA..L...--G...EVI.LRS..PLD..TI..SV.KT.RL..VEE. 350
```

Region 4
```
MRTGGIGASLTAAINE-NFHDYLDAPVMCLSSQDVPTPYAGTLEEWTVVQ 393
MKTAGIGAELIAQINE-HLFDELDAPVVRLSSQDIPTPYNGSLEQATVIQ 311
FPQHGVCAEICASVVE-ESFSYLDAPVERIAGADVPIPYTANLERLALPQ 347
```

FIGURE 9

```
WPQFGVGAEICARIMEGPAFNFLDAPAVRVTGADVPMPYAKILEDNSIPQ 345
FPSFGVGAEIVAQVMESEAFDYLDAPIQRVTGADVPTPYAKELEDFAFPD 351
WPNCGVGAEISARVTESDAFGYLDGPILRVTGVDVPMPYAQPLETAALPQ 346
VKSFSVSAEIIATVNE-ECFEYIKAPLSRCTGYDVITPFDRG-EGYFQVN 313
QRQAGIAANVVAEINE-RAILSLEAPVLRVAAPDTVYPFAQA-ESVWLPN 311

....GVGAEI.A...E-..F.YLDAP..R...G.DVP.PYA...LE....PQ 400

PAQIVTAVEQLCQ------                                  406
PHQIIDAVKNIVNSSKTITT                                 331
IEDIVRASKRACYRSK----                                 363
VKDIIFAIKKTLNI------                                 359
TPTIVKAVKEVLSIE-----                                 366
PADVVKMVKKCLNVQ-----                                 361
PKKVLVKMQELLDFKF----                                 329
FKDVIETAKKVMNF------                                 325

```
A. t.      MAA------LLG-RSC------RKLSFPSLTHG-----------ARR-
23
Human      MAVVAAAAGWLLRLRAAGAEGHWRRLPGAGLARGFLHPAATVEDAAQRRQ
50
Bovine     MAAVAAFAGWLLRLRAAGADGPWRRLCGAGLSRGFLQSASAY-GAAQRRQ
49

Consensus  MAAVAA.AGWLLRLRAAGA.G.WRRL.GAGL.RGFL..A....-.AAQRRQ
50

V----------STETGKP--LNLYSAINQALHIALDTDPRSYVFGEDVGF   61
           VAHFTFQPDPEPREYGQTQKMNLFQSVTSALDNSLAKDPTAVIFGEDVAF  100
           VAHFTFQPDPEPVEYGQTQKMNLFQAVTSALDNSLAKDPTAVIFGEDVAF   99

VAHTFQPDPEP.EYGQTQKMNLFQAVTSALDNSLAKDPTAVIFGEDVAF   100

GGVFRCTTGLAERFGKNRVFNTPLCEQGIVGFGIGLAAMGNRAIVEIQFA  111
           GGVFRCTVGLRDKYGKDRVFNTPLCEQGIVGFGIGIAVTGATAIAEIQFA  150
           GGVFRCTVGLRDKYGKDRVFNTPLCEQGIVGFGIGIAVTGATAIAEIQFA  149

GGVFRCTVGLRDKYGKDRVFNTPLCEQGIVGFGIGIAVTGATAIAEIQFA  150

DYIYPAFDQIVNEAAKFRYRSGNQFNCGGLTIRAPYGAVGHGGHYHSQSP  161
           DYIFPAFDQIVNEAAKYRYRSGDLFNCGSLTIRSPWGCVGHGALYHSQSP  200
           DYIFPAFDQIVNEAAKYRYRSGDLFNCGSLTIRSPWGCVGHGALYHSQSP  199

DYIFPAFDQIVNEAAKYRYRSGDLFNCGSLTIRSPWGCVGHGALYHSQSP  200

EAFFCHVPGIKVVIPRSPREAKGLLLSCIRDPNPVVFFEPKWLYRQAVEE  211
           EAFFAHCPGIKVVIPRSPFQAKGLLLSCIEDKNPCIFFEPKILYRAAAEE  250
           EAFFAHCPGIKVVVPRSPFQAKGLLLSCIEDKNPCIFFEPKILYRAAVEQ  249

EAFFAHCPGIKVVIPRSPFQAKGLLLSCIEDKNPCIFFEPKILYRAAVEE  250
```

FIGURE 10

```
VPEHDYMIPLSEAEVIREGNDITLVGWGAQLTVMEQ-ACLDAEKEGISCE    260
VPIEPYNIPLSQAEVIQEGSDVTLVAWGTQVHVIREVASMAKEKLGVSCE    300
VPVEPYNIPLSQAEVIQEGSDVTLVAWGTQVHEIREVAAMAQEKLGVSCE    299

VP.EPYNIPLSQAEVIQEGSDVTLVAWGTQVHVIREVA.MA.EKLGVSCE    300

LIDLKTLLPWDKETVEASVKKTGRLLISHEAPVTGGFGAEISATILERCF    310
VIDLRTIIPWDVDTICKSVIKSGRLLISHEAPLTGGFASEISSTVQEECF    350
VIDLRTILPWDVDTVCKSVIKTGRLLVSHEAPLTGGFASEISSTVQEQCF    349

VIDLRTILPWDVDTVCKSVIKTGRLLISHEAPLTGGFASEISSTVQE.CF    350

LKLEAPVSRVCGLDTPFPLVFEPFYMPTKNKILDAIKSTVNY    352
LNLEAPISRVCGYDTPFPHIFEPFYIPDKWKCYDALRKMINY    392
LNLEAPISRVCGYDTPFPHIFEPFYIPDKWKCYDALRKMINY    391

LNLEAPISRVCGYDTPFPHIFEPFYIPDKWKCYDALRKMINY    392
```

FIGURE 11

```
CATCTCTTGT TCTCTCCGCC CATCTCTGCT CTCTTTTATT TTCCCAGAAA GTTTTTTTTT      60
TTTTTTCCGA ATTCCGTTAA TCTCATTGGG GTTTCCATTG ATAGCAATGG CGACGGCTTT     120
CGCTCCCACT AAGCTCACTG CCACGGTTCC TCTGCATGGA TCCCATGAGA ATCGTCTCTT     180
GCTCCCGATC CGATTGGCTC CTCCTTCTTC TTTCCTCGGA TCCACCCGTT CCCTCTCCCT     240
TCGCAGACTC AATCACTCCA ACGCCACCCG TCGATCTCCC GTCGTCTCTG TCCAGGAAGT     300
TGTCAAGGAG AAGCAATCCA CCAATAATAC CAGCCTGTTG ATAACCAAAG AGGAAGGATT     360
GGAGTTGTAT GAAGATATGA TACTAGGTAG ATCTTTCGAA GACATGTGTG CTCAAATGTA     420
TTACCGAGGC AAGATGTTTG GTTTTGTTCA CTTGTACAAT GGCCAAGAGG CTGTTTCTAC     480
TGGCTTTATC AAGCTCCTTA CCAAGTCTGA CTCTGTCGTT AGTACCTACC GTGACCATGT     540
CCATGCCCTC AGCAAAGGTG TCTCTGCTCG TGCTGTTATG AGCGAGCTCT TCGGCAAGGT     600
TACTGGATGC TGCAGAGGCC AAGGTGGATC CATGCACATG TTCTCCAAAG AACACAACAT     660
GCTTGGTGGC TTTGCTTTTA TTGGTGAAGG CATTCCTGTC GCCACTGGTG CTGCCTTTAG     720
CTCCAAGTAC AGGAGGGAAG TCTTGAAACA GGATTGTGAT GATGTCACTG TCGCCTTTTT     780
CGGAGATGGA ACTTGTAACA ACGGACAGTT CTTCGAGTGT CTCAACATGG CTGCTCTCTA     840
TAAACTGCCT ATTATCTTTG TTGTCGAGAA TAACTTGTGG GCCATTGGGA TGTCTCACTT     900
GAGAGCCACT TCTGACCCCG AGATTTGGAA GAAAGGTCCT GCATTTGGGA TGCCTGGTGT     960
TCATGTTGAC GGTATGGATG TCTTGAAGGT CAGGGAAGTC GCTAAAGAAG CTGTCACTAG    1020
AGCTAGAAGA GGAGAAGGTC CAACCTTGGT TGAATGTGAG ACTTATAGAT TCAGAGGACA    1080
CTCCTTGGCT GATCCCGATG AGCTCCGTGA TGCTGCTGAG AAAGCCAAAT ACGCGGCTAG    1140
AGACCCAATC GCAGCATTGA AGAAGTATTT GATAGAGAAC AAGCTTGCAA AGGAAGCAGA    1200
GCTAAAGTCA ATAGAGAAAA AGATAGACGA GTTGGTGGAG GAAGCGGTTG AGTTTGCAGA    1260
CGCTAGTCCA CAGCCCGGTC GCAGTCAGTT GCTAGAGAAT GTGTTTGCTG ATCCAAAAGG    1320
ATTTGGAATT GGACCTGATG GACGGTACAG ATGTGAGGAC CCCAAGTTTA CCGAAGGCAC    1380
AGCTCAAGTC TGAGAAGACA AGTTTAACCA TAAGCTGTCT ACTGTCTCTT CGATGTTTCT    1440
ATATATCTTA TTAAGTTAAA TGCTACAGAG AATCAGTTTG AATCATTGC ACTTTTTGCT    1500
TAAAAAAAAA AAAAAAAAAA AAAAAAAAA                                     1530
```

FIGURE 12

| | |
|---|---:|
| MATAFAPTKL TATVPLHGSH ENRLLLPIRL APPSSFLGST RSLSLRRLNH SNATRRSPVV | 60 |
| SVQEVVKEKQ STNNTSLLIT KEEGLELYED MILGRSFEDM CAQMYYRGKM FGFVHLYNGQ | 120 |
| EAVSTGFIKL LTKSDSVVST YRDHVHALSK GVSARAVMSE LFGKVTGCCR GQGGSMHMFS | 180 |
| KEHNMLGGFA FIGEGIPVAT GAAFSSKYRR EVLKQDCDDV TVAFFGDGTC NNGQFFECLN | 240 |
| MAALYKLPII FVVENNLWAI GMSHLRATSD PEIWKKGPAF GMPGVHVDGM DVLKVREVAK | 300 |
| EAVTRARRGE GPTLVECETY RFRGHSLADP DELRDAAEKA KYAARDPIAA LKKYLIENKL | 360 |
| AKEAELKSIE KKIDELVEEA VEFADASPQP GRSQLLENVF ADPKGFGIGP DGRYRCEDPK | 420 |
| FTEGTAQV | 428 |

FIGURE 13

```
GAAAAAATGT CTTCGATAAT CCATGGAGCT GGAGCTGCTA CGACGACGTT ATCGACGTTT      60
AATTCCGTCG ATTCCAAGAA ACTCTTCGTT GCTCCTTCTC GCACAAATCT TTCAGTGAGG     120
AGCCAGAGAT ATATAGTGGC TGGATCTGAT GCGAGTAAGA AGAGCTTTGG TTCTGGACTT     180
AGAGTTCGTC ACTCTCAGAA ATTGATTCCA AATGCTGTTG CGACGAAGGA GGCGGATACG     240
TCTGCGAGCA CTGGACATGA ACTATTGCTT TTCGAGGCTC TTCAGGAAGG TCTGGAAGAA     300
GAGATGGACA GAGATCCACA TGTATGTGTT ATGGGTGAAG ATGTTGGCCA TTACGGAGGT     360
TCCTACAAGG TAACCAAAGG CCTTGCTGAT AAATTTGGTG ACCTCAGGGT TCTCGACACT     420
CCTATTTGTG AAAATGCATT CACCGGTATG GGCATTGGAG CTGCCATGAC TGGTCTAAGA     480
CCCGTTATTG AAGGTATGAA CATGGGTTTC CTCCTCCTCG CCTTCAACCA AATCTCCAAC     540
AACTGTGGAA TGCTTCACTA CACATCCGGT GGTCAGTTTA CGATCCCGGT TGTCATCCGT     600
GGACCTGGTG GAGTGGGACG CCAGCTTGGT GCTGAGCATT CACAGAGGTT AGAATCTTAC     660
TTTCAGTCCA TCCCTGGGAT CCAGATGGTT GCTTGCTCAA CTCCTTACAA CGCCAAAGGG     720
TTGATGAAAG CCGCAATAAG AAGCGAGAAC CCTGTGATTC TGTTCGAACA CGTGCTGCTT     780
TACAATCTCA AGGAGAAAAT CCCGGATGAA GATTACATCT GTAACCTTGA AGAAGCTGAG     840
ATGGTCAGAC CTGGCGAGCA CATTACCATC CTCACTTACT CGCGAATGAG GTACCATGTG     900
ATGCAGGCAG CAAAAACTCT GGTGAACAAA GGGTATGACC CCGAGGTTAT CGACATCAGG     960
TCACTGAAAC CGTTCGACCT TCACACAATT GGAAACTCGG TGAAGAAAAC ACATCGGGTT    1020
TTGATCGTGG AGGAGTGTAT GAGAACCGGT GGGATTGGGG CAAGTCTTAC AGCTGCCATC    1080
AACGAGAACT TCATGACTA CTTAGATGCT CCGGTGATGT GTTTATCTTC TCAAGACGTT    1140
CCTACACCTT ACGCTGGTAC ACTGGAGGAG TGGACCGTGG TTCAACCGGC TCAGATCGTG    1200
ACCGCTGTCG AGCAGCTTTG CCAGTAAATT CATATTTATC CGATGAACCA TTATTTATCA    1260
TTTACCTCTC CATTTCCTTT CTCTGTAGCT TAGTTCTTAA AGAATTTGTC TAAGATGGTT    1320
TGTTTTTGTT AAAGTTTGTC TCCTTTGTTG TGTCTTTTAA TATGGTTTGT AACTCAGAAT    1380
GTTTGTTTGT TAATTTTATC TCCCACTTTC TTTTAAAAAA AAAAAAAAAA AAAAAAAAA    1440
A                                                                   1441
```

FIGURE 14

| | |
|---|---|
| MSSIIHGAGA ATTTLSTFNS VDSKKLFVAP SRTNLSVRSQ RYIVAGSDAS KKSFGSGLRV | 60 |
| RHSQKLIPNA VATKEADTSA STGHELLLFE ALQEGLEEEM DRDPHVCVMG EDVGHYGGSY | 120 |
| KVTKGLADKF GDLRVLDTPI CENAFTGMGI GAAMTGLRPV IEGMNMGFLL LAFNQISNNC | 180 |
| GMLHYTSGGQ FTIPVVIRGP GGVGRQLGAE HSQRLESYFQ SIPGIQMVAC STPYNAKGLM | 240 |
| KAAIRSENPV ILFEHVLLYN LKEKIPDEDY ICNLEEAEMV RPGEHITILT YSRMRYHVMQ | 300 |
| AAKTLVNKGY DPEVIDIRSL KPFDLHTIGN SVKKTHRVLI VEECMRTGGI GASLTAAINE | 360 |
| NFHDYLDAPV MCLSSQDVPT PYAGTLEEWT VVQPAQIVTA VEQLCQ | 406 |

FIGURE 15

```
GGGCGATCTG GTTTGCTAGA TCCAAAACCC TTGTTTCTAG CTTGAGACAT      50
AATCTAAATT TGTCGACAAT TCTCATAAAA CGTGATTACT CTCATCGTCC     100
CATCTTCTAT ACAACTTCTC AGTTATCTTC AACGGCGTAT TTGAGTCCCT     150
TCGGTAGCCT CCGTCATGAG TCTACGGCCG TGGAGACACA GGCTGATCAT     200
TTGGTTCAGC AGATTGATGA AGTCGATGCC CAGGAACTGG ATTTCCAGG      250
AGCCAAAGTC CGTTACACAT CGGAGATGAA ATTCATACCG GAATCATCTT     300
CAAGGAGGAT TCCATGTTAC CGGGTTCTTG ACGAAGACGG ACGAATCATC     350
CCCGATAGCG ATTTTATTCC CGTCAGTGAG AAACTCGCTG TTAGAATGTA     400
CGAACAAATG GCGACGCTAC AAGTAATGGA TCACATCTTC TACGAAGCTC     450
AACGTCAACG AAGAATATCT TTTTATCTTA CTTCCGTCGG AGAAGAAGCC     500
ATTAACATCG CTTCAGCAGC TGCTCTCAGT CCTGACGACG TCGTTTTACC     550
TCAGTACCGA GAACCTGGAG TTCTTTTGTG GCGTGCCTTC ACGTTGGACG     600
AGTTTGCTAA TCAGTGTTTT GGGAACAAAG CTGATTATGG CAAAGGCAGA     650
CAAATGCCAA TTCATTACGG TTCCAATCGT CTTAATTACT TCACTATCTC     700
CTCTCCAATT GCCACGCAAC TTCCTCAAGC TGCTGGAGTT GGTTATTCTT     750
TGAAAATGGA CAAGAAGAAT GCTTGTACTG TTACATTCAT CGGAGATGGT     800
GGCACAAGCG AGGAGATTT TCACGCCGGA TTGAATTTTG CGGCCGTAAT      850
GGAAGCTCCG GTTGTGTTTA TATGTCGGAA CAACGGTTCG GCGATTAGTA     900
CTCATATCTC AGAACAGTTT AGAAGTGATG GAATAGTTGT GAAAGCTCAA     950
GCTTACGGTA TCCCGAAGCA TCCCGTGTGG GACGGTACCG ATGCACTTGC    1000
CGTTTATAGT GCTGTACCCT CAGCTCGAGA AATGGCTGTA ACAGAACAAA    1050
GACCTGTTCT CATTGAGATG ATGACATATA GAGTAGGACA TCATTCTACA    1100
TCAGATGATT CAACTAAGTA CAGGCGGCG GATGAAATCC AGTACTGGAA     1150
AATGTCGAGA AACCCTGTGA ATAGATTTCG GAAATCGGTC GAAGATAACG    1200
GATGGTCGAG TGAGGAAGAT GAATCCAAGC TAAGATCTAA CGCAAGAAAA    1250
CAGCTTCTGC AAGCGATTCA GGCTCCGAG AAGTCGGACA AACAACCATT     1300
GACAGAGTTG TTTAACGATG TATATGATGT TAAACCGAAG AACCTAGAAG    1350
AGCAAGAACT TGGTTGAAG GAATTAGTAA AGAAACAACC TCAAGATTAT     1400
CCTCCTCCT TTCATGTTTG AATCTAGACG AACTGTGTGG TTAAATACC      1450
TCGCGGACCG CGAATTCGAT ATCAAGCTTC TCATTCAGA CTATTTATAT     1500
TGTCCACGTA TCGAATAGTA ATCAAGTATC AATGTAGAGA CCAGCATTTG    1550
GAGCATCAAA AAAAAAAAA AAAAAAAAA AAAAAA                     1587
```

FIGURE 16

```
AIWFARSKTL  VSSLRHNLNL  STILIKRDYS  HRPIFYTTSQ  LSSTAYLSPF     50

GSLRHESTAV  ETQADHLVQQ  IDEVDAQELD  FPGGKVGYTS  EMKFIPESSS    100

RRIPCYRVLD  EDGRIIPDSD  FIPVSEKLAV  RMYEQMATLQ  VMDHIFYEAQ    150

RQGRISFYLT  SVGEEAINIA  SAAALSPDDV  VLPQYREPGV  LLWRGFTLEE    200
                                                TPP binding site
FANQCFGNKA  DYGKGRQMPI  HYGSNRLNYF  TISSPIATQL  PQAAGVGYSL    250
                        BCOADC E1β binding site
KMDKKNACTV  TFIGDGGTSE  GDFHAGLNFA  AVMEAPVVFI  CRNNGWAIST    300

HISEQFRSDG  IVVKGQAYGI  PKHPVWDGTD  ALAVYSAVRS  AREMAVTEQR    350
            •           ○
PVLIEMMTYR  VGHHSTSDDS  TKYRAADEIQ  YWKMSRNPVN  RFRKWVEDNG    400

WWSEEDESKL  RSNARKQLLQ  AIQAAEKWEK  QPLTELFNDV  YDVKPKNLEE    450

QELGLKELVK  KQPQDYPPGF  HV                                    472
```

FIGURE 17

```
          10         20         30         40         50
    1234567890 1234567890 1234567890 1234567890 1234567890
    TTCTTCACCC ACCAAAAGTA GCAAACCTTT GCCACCTAAA AATCTTACCA    50
    GTTGGGTGAA AGTTGCCAAA ATAGAGCTTG CTTTTGTCGC AATCCTATAT   100
    TTTTCAGATT GATTGTTGGT GGGTTTGTGT AAATGGCGGC TCTTTTAGGC   150
    AGATCCTGCC GGAAACTGAG TTTTCCGAGC TTGACTCACG GAGCTAGGAG   200
    GGTATCGACG GAAACTGGAA AACCATTGAA TCTATACTCT GCTATTAATC   250
    AAGCGCTTCA CATCGCTTTG GACACCGATC CTCGGTCTTA TGTCTTTGGG   300
    GAAGACGTTG GCTTTGGTGG AGTCTTTCGC TGTACAACTG GTTAGCTGA    350
    ACGATTCGGG AAAAACCGTG TCTTCAATAC TCCTCTTTGT GAGCAGGGCA   400
    TTGTTGGATT TGGCATTGGT CTAGCAGCAA TGGGTAATCG AGCAATTGTA   450
    GAGATTCAGT TTGCAGATTA TATATATCCT GCTTTTGATC AGATTGTTAA   500
    TGAAGCTGCA AAGTTCAGAT ACCGAAGTGG TAACCAATTC AACTGTGGAG   550
    GACTTACGAT AAGAGCACCA TATGGAGCAG TTGGTCATGG TGACATTAC    600
    CATTCACAAT CCCCTGAAGC TTTCTTTTGC CATGTCCCTG GTATTAAGGT   650
    TGTTATCCCT CGGAGTCCAC GAGAAGCAAA GGACTGTTG  TTGTCATGTA   700
    TCCGTGATCC AAATCCCGTT GTTTCTTCG  AACCAAAGTG GCTGTATCGT   750
    CAAGCAGTAG AAGAAGTCCC TGAGCATGAC TATATGATAC CTTTATCAGA   800
    AGCAGAGGTT ATAAGAGAAG GCAATGACAT TACACTGGTT GGATGGGAG    850
    CTCAGCTTAC CGTTATGGAA CAAGCTTGTC TGGACGCGGA AAAGGAAGGA   900
    ATATCATGTG AACTGATAGA TCTCAAGACA CTGCTTCCTT GGACAAAGA    950
    AACCGTTGAG GCTTCAGTTA AAAAGACTGG CAGACTTCTT ATAAGCCATG  1000
    AAGCTCCTGT AACAGGAGGT TTGGAGCAG  AGATCTCTGC AACAATTCTG  1050
    GAACGTTGCT TTTTCAAGTT AGAAGCTCCA GTAAGCAGAG TTTGTGGTCT  1100
    GGATACTCCA TTTCCTCTTG TGTTTGAACC ATTCTACATG CCCACCAAGA  1150
    ACAAGATATT GGATGCAATC AAATCGACTG TGAATTACTA GCCGTACTAT  1200
    CTGTAGTTTA CTGTTTACAC TAGGACTAAT GTAATCGCAT GTCTTTGTTA  1250
    TCAATTCGTC TAATGTAACA CTACCGATTA ACTTTAATGA ATTTCAAGAT  1300
    AACGAAAAA  AAAAAAAA                                     1319
```

FIGURE 18

```
          10         20         30         40         50
     1234567890 1234567890 1234567890 1234567890 1234567890
     MAALLGRSCR KLSFPSLTHG ARRVSTETGK PLNLYSAINQ ALHIALDTDP      50
     RSYVFGEDVG FGGVFRCTTG LAERFGKNRV FNTPLCEQGI VGFGIGLAAM     100
     GNRAIVEIQF ADYIYPAFDQ IVNEAAKFRY RSGNQFNCGG LTIRAPYGAV     150
     GHGGHYHSQS PEAFFCHVPG IKVVIPRSPR EAKGLLLSCI RDPNPVVFFE     200
     PKWLYRQAVE EVPEHDYMIP LSEAEVIREG NDITLVGWGA QLTVMEQACL     250
     DAEKEGISCE LIDLKTLLPW DKEIVEASVK KTGRLLISHE APVTGGFGAE     300
     ISATILERCF LKLEAPVSRV CGLDTPFPLV FEPFYMPTKN KILDAIKSTV     350
     NY                                                        352
```

DNA ENCODING PLASTID PYRUVATE DEHYDROGENASE AND BRANCHED CHAIN OXOACID DEHYDROGENASE COMPONENTS

This application claims the benefit of priority of the following Provisional patent applications: Serial No. 60/051,291, filed Jun. 30, 1997; Ser. No. 60/055,255, filed Aug. 1, 1997; Ser. No. 60/076,544, filed Mar. 2, 1998; and Ser. No. 60/076,554, filed Mar. 2, 1998.

BACKGROUND OF THE INVENTION

1. Field of the Invention

The present invention relates to genetically engineered plants. More particularly, the present invention relates to the optimization of substrate pools to facilitate the biosynthetic production of commercially useful polyhydroxyalkanoates (PHAs) in plants.

The present invention especially relates to the production of copolyesters of 3-hydroxybutyrate (3HB) and 3-hydroxyvalerate (3HV), designated P(3HB-co-3HV) copolymer, and derivatives thereof.

2. Description of Related Art

Polyhydroxyalkanoates

Polyhydroxyalkanoates are polyesters that accumulate in a wide variety of bacteria. These polymers have properties ranging from stiff and brittle plastics to rubber-like materials, and are biodegradable. Due to these properties, PHAs are an attractive source of non-polluting plastics and elastomers.

Currently, there are approximately a dozen biodegradable plastics in commercial use that possess properties suitable for producing a number of specialty and commodity products (Lindsay, 1992). One such biodegradable plastic in the polyhydroxyalkanoate (PHA) family that is commercially important is Biopol™, a random copolymer of 3-hydroxybutyrate (3HB) and 3-hydroxyvalerate (3HV). This bioplastic is used to produce biodegradable molded material (e.g., bottles), films, coatings, and in drug release applications. Biopol™ is produced via a fermentation process employing the bacterium Alcaligenes eutrophus (Byrom, 1987). The current market price is $6–7/lb, and the annual production is 1,000 tons. By best estimates, this price is likely to be reduced only about 2-fold via fermentation (Poirier et al., 1995). Competitive synthetic plastics such as polypropylene and polyethylene cost about 35–45¢/lb (Layman, 1994). The annual global demand for polyethylene alone is about 37 million metric tons (Poirier et al., 1995). It is therefore likely that the cost of producing P(3HB-co-3HV) by microbial fermentation will restrict its use to low-volume specialty applications.

Nakamura et al. (1992) reported using threonine (20 g/L) as the sole carbon source for the production of P(3HB-co-3HV) copolymer in A. eutrophus. These workers initially suggested that the copolymer might form via the degradation of threonine by threonine deaminase, with conversion of the resultant α-ketobutyrate (=2-oxobutyrate) to propionyl-CoA. However, they ultimately concluded that threonine was utilized directly, without breaking carbon-carbon bonds, to form valeryl-CoA as the 3HV precursor. The nature of this chemical conversion was not described, but since the breaking of carbon-carbon bonds was not postulated to occur, the pathway could not involve threonine deaminase in conjunction with an α-ketoacid decarboxylating step to form propionate or propionyl-CoA. In the experiments of Nakamura et al., the PHA polymer content was very low (<6% of dry cell weight). This result, in conjunction with the expense of feeding bacteria threonine, makes their approach impractical for the commercial production of P(3HB-co3HV) copolymer.

Yoon et al. (1995) have shown that growth of Alcaligenes sp. SH-69 on a medium supplemented with threonine, isoleucine, or valine resulted in significant increases in the 3HV fraction of the P(3HB-co-3HV) copolymer. In addition to these amino acids, glucose (3% wt/vol) was also added to the growth media. In contrast to the results obtained by Nakamura et al. (1992), growth of A. eutrophus under the conditions described by Yoon et al. (1995) did not result in the production of P(3HB-co-3HV) copolymer when the medium was supplemented with threonine as the sole carbon source. From their results, Yoon et al. (1995) implied that the synthetic pathway for the 3HV component in P(3HB-co-3HV) copolymer is likely the same as that described in WO 91/18995 and Steinbüchel and Pieper (1992). This postulated synthetic pathway involves the degradation of isoleucine to propionyl-CoA (FIG. 3).

The PHB Biosynthetic Pathway

Polyhydroxybutyrate (PHB) was first discovered in 1926 as a constituent of the bacterium Bacillus megaterium (Lemoigne, 1926). Since then, PHAs such as PHB have been found in more than 90 different genera of gram-negative and gram-positive bacteria (Steinbüchel, 1991). These microorganisms produce PHAs using R-β-hydroxyacyl-CoAs as the direct metabolic substrate for a PHA synthase, and produce polymers of R-(3)-hydroxyalkanoates having chain lengths ranging from C3–C14 (Steinbüchel and Valentin, 1995).

To date, the best understood biochemical pathway for PHB production is that found in the bacterium Alcaligenes eutrophus (Dawes and Senior, 1973; Slater et al., 1988; Schubert et al., 1988; Peoples and Sinskey, 1989a and 1989b). This pathway, which is also utilized by other microorganisms, is summarized in FIG. 1. In this organism, an operon encoding three gene products, i.e., PHB synthase, β-ketothiolase, and acetoacetyl-CoA reductase, encoded by the phbC, phbA, and phbB genes, respectively, are required to produce the PHA homopolymer R-polyhydroxy-butyrate (PHB).

As further shown in FIG. 1, acetyl-CoA is the starting substrate employed in the biosynthetic pathway. This metabolite is naturally available for PHB production in the cytoplasm and plastids of plants.

Poirier et al. (1992) demonstrated that a multi-enzyme pathway can be introduced into plants to produce polyhydroxybutyrate (PHB). In that work, the genes encoding the Alcaligenes eutrophus acetoacetyl-CoA reductase (phbB) and PHB synthase (phbC) genes were introduced into Arabidopsis thaliana, where the enzymes were expressed cytoplasmically. A 3-ketothiolase is already expressed in the cytoplasm of Arabidopsis. Although PHB was produced in the plants which expressed the three enzymes, the yield was low and the plants were stunted and had reduced seed production.

Nawrath et al. (1994) provided a solution to these problems. There, the genes for the three bacterial PHB enzymes (phbC, phbA, and phbB) were modified to comprise a pea chloroplast targeting peptide (="transit peptide"), which targeted the enzymes to the chloroplast. Arabidopsis plants which produced these three enzymes in the chloroplast accumulated large amounts of PHB. There was also no apparent affect of these transgenes, or of the PHB accumulation, on the growth and development of the transgenic plants.

The P(3HB-co-3HV) Copolymer Biosynthetic Pathway

As noted above, P(3HB-co-3HV) random copolymer, commercially known as Biopol™, is produced by fermentation employing A. eutrophus. A proposed biosynthetic pathway for P(3HB-co-3HV) copolymer production is shown in FIG. 2. Production of this polymer in plants has been reported (oral presentation by Mitsky et al., 1997).

Since the production of PHB in chloroplasts apparently does not affect plant growth and development as does production of PHB in the cytoplasm (Nawrath et al., 1992), the chloroplast is the preferred site of P(3HB-co-3HV) biosynthesis. The successful production of P(3HB-co-3HV) copolymer in plants thus requires the presence of three PHA biosynthetic enzymes as well as the substrates required for the copolymer biosynthesis (FIG. 2), preferably in the plastids. For the 3HB component of the polymer, the substrate naturally exists in chloroplasts in sufficient concentration in the form of acetyl-CoA (Nawrath et al., 1994). However, this is not true for the 3HV component of the polymer, where the starting substrate is propionyl-CoA. FIG. 3 is an overview of enzyme pathways which are related to the provision of these substrates. The engineering of plants to generate sufficient chloroplast pools of propionyl-CoA, along with the proper PHA biosynthetic enzymes (i.e., a β-ketothiolase, a β-ketoacyl-CoA reductase, and a PHA synthase), makes it possible to produce copolyesters of poly(3HB-co-3HV) in these organisms.

Methods for optimization of PHB and P(3HB-co-3HV) production in various crop plants are disclosed in Gruys et al. (1998). A major focus in that invention is the optimization of the substrate pools for P(3HB-co-3HV), in order to provide 2-ketobutyrate and propionyl-CoA to the site of copolymer synthesis. Gruys et al. (1998) also discusses exploring the potential use of a pyruvate dehydrogenase complex and a branched chain oxoacid dehydrogenase complex to convert 2-oxobutyrate to propionyl-CoA.

Gruys et al. (1998) also provides methods for the optimization of β-ketothiolase, β-ketoacyl-CoA reductase, and PHA synthase activities in plants and bacteria. It was determined therein that the A. eutrophus β-ketothiolase PhbB was metabolically blocked from producing P(3HB-co-3HV) due to its inability to utilize propionyl-CoA with acetyl-CoA to produce 3-ketovaleryl-CoA (see FIG. 2). However, Gruys et al. (1998) demonstrated that another A. eutrophus β-ketothiolase, designated BktB, is able to produce 3-ketovaleryl-CoA from propionyl-CoA and acetyl-CoA. Therefore, BktB is a preferred β-ketothiolase for the production of P(3HB-co-3HV). Gruys et al. also demonstrated that other β-ketothiolases are able to produce 3-keto-valeryl-CoA from propionyl-CoA and acetyl-CoA. These are: another A. eutrophus β-ketothiolase, designated pAE65, and two β-ketothiolases from Zoogloea ramigera, designated "A" and "B".

Gruys et al. (1998) noted that the sources of the three copolymer biosynthetic enzymes may encompass a wide range of organisms, including, for example, Alcaligenes eutrophus, Alcaligenes faecalis, Aphanothece sp., Azotobacter vinelandii, Bacillus cereus, Bacillus megaterium, Beijerinkia indica, Derxia gummosa, Methylobacterium sp., Microcoleus sp., Nocardia corallina, Pseudomonas cepacia, Pseudomonas extorguens, Pseudomonas oleovorans, Rhodobacter sphaeroides, Rhodobacter capsulatus, Rhodospirillum rubrum (Brandl et al., 1990; Doi, 1990), and Thiocapsa pfennigii.

Pyruvate Dehydrogenase Complex

The pyruvate dehydrogenase complex (PDC) is a large multi-enzyme structure composed of three primary component enzymes, pyruvate dehydrogenase (PDH) (E1, EC 1.2.41); dihydrolipoamide acetyltransferase (E2, EC 2.3.1.12); and dihydrolipoamide dehydrogenase (E3, EC 1.8.1.4) (Reed, 1974). In the well-characterized mammalian complex, 60 subunits of E2 comprise the central core, and the E1 and E3 components decorate the outer surface of this core (Patel et al., 1990). E1 is a heterotetramer composed of two α and two β subunits. The E3 component, a homodimer, associates with the complex via an E3 binding protein (Gopalakrishnan, 1989).

The PDC catalyzes the irreversible oxidative decarboxylation of pyruvate according to the equation:

Pyruvate+CoA+NAD$^+$→Acetyl-CoA+CO$_2$+NADH+H$^+$

In mitochondria, this reaction represents the irreversible commitment of carbon to the citric acid cycle, and therefore is a logical point for regulation. Previous experiments have shown that plant mitochondrial PDC activity is, in fact, regulated by product inhibition, metabolites, and reversible phosphorylation (Randall et al., 1977; Randall et al., 1989; Randall et al., 1996; Budde et al, 1991) as is the mammalian complex (Patel et al., 1990).

In prokaryotes, PDC is localized in the cytoplasm, while in eukaryotes it is within the mitochondrial matrix. Plants, however, are unique in that a second form of the complex exists in the plastids (Reid et al., 1975; Reid et al., 1977; Thompson et al, 1977b). Based upon enzymology (Thompson et al., 1977a; Williams et al., 1979; Camp et al., 1988) and immunochemical analyses (Taylor et al., 1992; Camp et al, 1985) it is clear that plastid PDC is distinct from its mitochondrial counterpart. In plants, de novo fatty acid biosynthesis occurs exclusively in the plastids (Miernyk et al., 1983; Kang et al., 1994; Zilket et al., 1969; Drennan et al., 1969; Ohlrogge et al., 1979). The plastid form of PDC can provide the fatty acid precursor, acetyl-CoA (Miernyk et al., 1983; Kang et al., 1994; Grof et al., 1995). The plastid PDC can also catalyze the oxidative decarboxylation of 2-oxobutyrate to produce propionyl CoA (Camp et al., 1988; Camp and Randall, 1985).

The cDNAs that encode the E1α and E1β subunits of plant mitochondrial PDH have been cloned (Grof et al., 1995; Leuthy et al., 1995; Leuthy et al, 1994). Recently, Reith and Munholland (1995) reported the sequence of the entire plastid genome of the red alga P. purpurea. Encoded in this genome are open reading frames homologous to PDH α and β subunits.

The cDNAs that encode the E2 component of the plant mitochondrial PDC have been similarly cloned (Guan et al., 1995). The sequence of the entire plastid genome of the cyanobacterium Synechocystis sp. has also recently been reported (Kaneko et al., 1996).

Branched Chain 2-Oxoacid Dehydrogenase Complex

The branched chain 2-oxoacid dehydrogenase complex (BCOADC) is a highly ordered macromolecular structure composed of three primary component enzymes, a branched chain dehydrogenase or decarboxylase (BCDH or E1; EC 1.2.4.4); dihydrolipoamide transacylase (LTA or E2; no EC number); and dihydrolipoamide dehydrogenase (LipDH or E3; EC 1.8.1.4) (Yeaman, 1989). The mammalian complex is assembled with 24 subunits of E2 as the central cubic core with 4:3:2 symmetry; the E1 and E3 components decorate the outer surface of the E2 core (Yeaman, 1989; Wynn et al., 1996). E1 is a heterotetramer composed of two identical α and two identical β subunits (Pettit et al., 1978). E3 associates loosely with the E2-E1 structure, and is a homodimer (Wynn et al., 1996; Pettit et al., 1978). The mammalian mitochondrial complex is also regulated by a specific E1-kinase and a phospho-E1 phosphatase, which modulate activity by reversible phosphorylation (inactivation) and dephosphorylation (reactivation). Additional regulation is achieved by product inhibition and modulation of gene expression (Yeaman, 1989; Wynn et al., 1996).

BCOADC catalyzes the irreversible oxidative decarboxylation of the branched-chain 2-oxoacids derived from valine, leucine and isoleucine, as well as 2-oxobutyrate and 4-methyl-2-oxobutyrate, with comparable rates and similar Km values (Yeaman 1989; Wynn et al., 1996; Paxton et al., 1986; Gerbling et al., 1988). The reactions are:

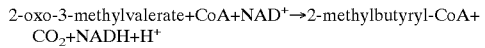
2-oxo-3-methylvalerate+CoA+NAD⁺→2-methylbutyryl-CoA+ CO₂+NADH+H⁺

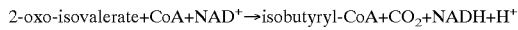
2-oxo-isovalerate+CoA+NAD⁺→isobutyryl-CoA+CO₂+NADH+H⁺

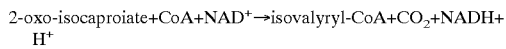
2-oxo-isocaproiate+CoA+NAD⁺→isovalyryl-CoA+CO₂+NADH+ H⁺

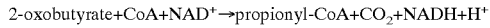
2-oxobutyrate+CoA+NAD⁺→propionyl-CoA+CO₂+NADH+H⁺

In mammals, BCOADC is found in the mitochondria and is involved in the catabolism of the branched-chain amino acids. The only reports describing BCOADC activity in plants have localized BCOADC to peroxisomes (Gerbling et al., 1988; Gerbling et al., 1989). The proposed function of a peroxisomal BCOADC is to catabolize the branched-chain amino acids during germination and growth, yielding an acyl-CoA product that would be further metabolized by the beta-oxidation pathway localized in the peroxisome (Gerbling et al., 1988; Gerbling et al., 1989).

To provide substrate pools to permit biosynthesis of P(3HB-co-3HV) copolymer in the plastid, there is a need for methods to engineer plants to produce plastid enzymes which convert 2-oxobutyrate to propionyl-CoA.

SUMMARY OF THE INVENTION

Accordingly, the present invention provides nucleotide sequences that encode the E1α and E1β subunits, and the E2 component of the plastid pyruvate dehydrogenase complex, as well as the E1α and E1β subunits, and the E2 component of the branched chain oxoacid dehydrogenase complex, of *Arabidopsis thaliana*. Methods of utilizing these nucleotide sequences to provide enzymatic activity to convert 2-oxobutyrate to propionyl-CoA, and to produce P(3HB-co-3HV) copolymer in plants, are also provided.

Accordingly, in a first aspect, the present invention provides an isolated DNA molecule, comprising a nucleotide sequence selected from: (a) the nucleotide sequence shown in SEQ ID NO:1, or the complement thereof; (b) a nucleotide sequence that hybridizes to the nucleotide sequence of (a) under a wash stringency equivalent to 0.5×SSC to 2×SSC, 0.1% SDS, at 55–65° C., and which encodes a polypeptide having enzymatic activity similar to that of *Arabidopsis thaliana* plastid pyruvate dehydrogenase complex E1α subunit; (c) a nucleotide sequence encoding the same genetic information as the nucleotide sequence of (a), but which is degenerate in accordance with the degeneracy of the genetic code; and (d) a nucleotide sequence encoding the same genetic information as the nucleotide sequence of (b), but which is degenerate in accordance with the degeneracy of the genetic code. Recombinant vectors comprising such isolated DNA molecules, host cells transformed with these vectors, and an isolated polypeptide having the amino acid sequence of SEQ ID NO.:2 are also provided.

In another aspect, the present invention provides an isolated DNA molecule, comprising a nucleotide sequence selected from: (a) the nucleotide sequence shown in SEQ ID NO:3, or the complement thereof; (b) a nucleotide sequence that hybridizes to the nucleotide sequence of (a) under a wash stringency equivalent to 0.5×SSC to 2×SSC, 0.1% SDS, at 55–65° C., and which encodes a polypeptide having enzymatic activity similar to that of *Arabidopsis thaliana* plastid pyruvate dehydrogenase complex E1β subunit; (c) a nucleotide sequence encoding the same genetic information as the nucleotide sequence of (a), but which is degenerate in accordance with the degeneracy of the genetic code; and (d) a nucleotide sequence encoding the same genetic information as the nucleotide sequence of (b), but which is degenerate in accordance with the degeneracy of the genetic code. Recombinant vectors comprising such isolated DNA molecules, host cells transformed with these vectors, and an isolated polypeptide having the amino acid sequence of SEQ ID NO.:4 are also provided.

In another aspect, the present invention provides an isolated DNA molecule, comprising a nucleotide sequence selected from: (a) the nucleotide sequence shown in SEQ ID NO:5, or the complement thereof; (b) a nucleotide sequence that hybridizes to the nucleotide sequence of (a) under a wash stringency equivalent to 0.5×SSC to 2×SSC, 0.1% SDS, at 55–65° C., and which encodes a polypeptide having enzymatic activity similar to that of *Arabidopsis thaliana* plastid pyruvate dehydrogenase complex E2 component; (c) a nucleotide sequence encoding the same genetic information as the nucleotide sequence of (a), but which is degenerate in accordance with the degeneracy of the genetic code; and (d) a nucleotide sequence encoding the same genetic information as the nucleotide sequence of (b), but which is degenerate in accordance with the degeneracy of the genetic code. Recombinant vectors comprising such isolated DNA molecules, host cells transformed with these vectors, and an isolated polypeptide having the amino acid sequence of SEQ ID NO.:6 are also provided.

In a further aspect, the present invention provides an isolated DNA molecule, comprising a nucleotide sequence selected from: (a) the nucleotide sequence shown in SEQ ID NO:11, or the complement thereof; (b) a nucleotide sequence that hybridizes to the nucleotide sequence of (a) under a wash stringency equivalent to 0.5×SSC to 2×SSC, 0.1% SDS, at 55–65° C., and which encodes a polypeptide having enzymatic activity similar to that of *Arabidopsis thaliana* branched chain 2-oxoacid dehydrogenase complex E1α subunit; (c) a nucleotide sequence encoding the same genetic information as the nucleotide sequence of (a), but which is degenerate in accordance with the degeneracy of the genetic code; and (d) a nucleotide sequence encoding the same genetic information as the nucleotide sequence of (b), but which is degenerate in accordance with the degeneracy of the genetic code. Recombinant vectors comprising such isolated DNA molecules, host cells transformed with these vectors, and an isolated polypeptide having the amino acid sequence of SEQ ID NO.:12 are also provided.

In another aspect, the present invention provides an isolated DNA molecule, comprising a nucleotide sequence selected from: (a) the nucleotide sequence shown in SEQ ID NO:13, or the complement thereof; (b) a nucleotide sequence that hybridizes to the nucleotide sequence of (a) under a wash stringency equivalent to 0.5×SSC to 2×SSC, 0.1% SDS, at 55–65° C., and which encodes a polypeptide having enzymatic activity similar to that of *Arabidopsis thaliana* branched chain 2-oxoacid dehydrogenase complex E1β subunit; (c) a nucleotide sequence encoding the same genetic information as the nucleotide sequence of (a), but which is degenerate in accordance with the degeneracy of the genetic code; and (d) a nucleotide sequence encoding the same genetic information as the nucleotide sequence of (b), but which is degenerate in accordance with the degeneracy of the genetic code. Recombinant vectors comprising such isolated DNA molecules, host cells transformed with these vectors, and an isolated polypeptide having the amino acid sequence of SEQ ID NO.:14 are also provided.

In another aspect, the present invention provides the foregoing isolated DNA molecules encoding a polypeptide having enzymatic activity similar to that of *Arabidopsis thaliana* branched chain 2-oxoacid dehydrogenase complex E1β subunit, but in which the naturally occurring branched chain oxoacid dehydrogenase complex E2 component binding region thereof is replaced with the E2 component binding region of a plastid pyruvate dehydrogenase complex E1β subunit. The plastid pyruvate dehydrogenase complex E1β subunit can have the sequence shown in SEQ ID NO.:3. Recombinant vectors comprising such isolated DNA molecules, host cells transformed with these vectors, and the isolated polypeptide are also provided.

In yet another aspect, the present invention provides an isolated DNA molecule, comprising a nucleotide sequence selected from: (a) the nucleotide sequence shown in SEQ ID NO:15, or the complement thereof; (b) a nucleotide sequence that hybridizes to the nucleotide sequence of (a) under a wash stringency equivalent to 0.5×SSC to 2×SSC, 0.1% SDS, at 55–65° C., and which encodes a polypeptide having enzymatic activity similar to that of *Arabidopsis thaliana* branched chain 2-oxoacid dehydrogenase complex E2 component; (c) a nucleotide sequence encoding the same genetic information as the nucleotide sequence of (a), but which is degenerate in accordance with the degeneracy of the genetic code; and (d) a nucleotide sequence encoding the same genetic information as the nucleotide sequence of (b), but which is degenerate in accordance with the degeneracy of the genetic code. Recombinant vectors comprising such isolated DNA molecules, host cells transformed with these vectors, and an isolated polypeptide having the amino acid sequence of SEQ ID NO.:16 are also provided.

In another aspect, the present invention provides a plant, a plastid of which comprises the following polypeptides: an enzyme that enhances the biosynthesis of
   2-oxobutyrate; a branched chain oxoacid dehydrogenase complex E1α subunit; a branched chain oxoacid dehydrogenase complex E1β subunit; and a branched chain oxoacid dehydrogenase complex E2 component. The branched chain oxoacid dehydrogenase complex E1α subunit can have the sequence shown in SEQ ID NO.:12, the branched chain oxoacid dehydrogenase complex E1β subunit can have the sequence shown in SEQ ID NO.:14, or the branched chain oxoacid dehydrogenase complex E2 component can have the sequence shown in SEQ ID NO.:16. In such plant, the plastid can further comprise the following polypeptides:
   a β-keto-thiolase; a β-ketoacyl-CoA reductase; and a polyhydroxy-alkanoate synthase. The genome of such plant can comprise introduced DNAs encoding these polypeptides, wherein each of the introduced DNAs is operatively linked to a targeting peptide coding region capable of directing transport of the polypeptide encoded thereby into a plastid. A method of producing P(3HB-co-3HV) copolymer comprises growing such plant, and recovering P(3HB-co-3HV) copolymer produced thereby.

In another aspect, the present invention comprises a plant, a plastid of which comprises the following polypeptides: an enzyme that enhances the biosynthesis of
   2-oxobutyrate; a branched chain oxoacid dehydrogenase complex E1α subunit; a branched chain oxoacid dehydrogenase complex E1β subunit; a branched chain oxoacid dehydrogenase complex E2 component; and a dihydrolipoamide dehydrogenase E3 component, which can be mitochondrially-derived. In such plant, the branched chain oxoacid dehydrogenase complex E1α subunit can have the sequence shown in SEQ ID NO.:12, the branched chain oxoacid dehydrogenase complex E1β subunit can have the sequence shown in SEQ ID NO.:14, or the branched chain oxoacid dehydrogenase complex E2 component can have the sequence shown in SEQ ID NO.:16. In such plant, the plastid can further comprise the following polypeptides:
   a β-keto-thiolase; a β-ketoacyl-CoA reductase; and a polyhydroxy-alkanoate synthase. The genome of such plant can comprise introduced DNAs encoding these polypeptides, wherein each of the introduced DNAs is operatively linked to a targeting peptide coding region capable of directing transport of the polypeptide encoded thereby into a plastid. A method of producing P(3HB-co-3HV) copolymer comprises growing such plant, and recovering P(3HB-co-3HV) copolymer produced thereby.

In yet another aspect, the present invention provides a plant, a plastid of which comprises the following polypeptides: an enzyme that enhances the biosynthesis of
   2-oxobutyrate; a branched chain oxoacid dehydrogenase complex E1α subunit; and a branched chain oxoacid dehydrogenase complex E1β subunit, the naturally occurring E2 binding region of which is replaced with the E2 binding region of a plastid pyruvate dehydrogenase complex E1β subunit. In such plant, the branched chain oxoacid dehydrogenase complex E1α subunit can have the sequence shown in SEQ ID NO.:12. Furthermore, in such plant, the plastid can further comprise the following polypeptides:
   a β-ketothiolase; a β-ketoacyl-CoA reductase; and a poly-hydroxyalkanoate synthase. In such plant, the genome can comprise introduced DNAs encoding these polypeptides, wherein each of the introduced DNAs is operatively linked to a targeting peptide coding region capable of directing transport of the polypeptide encoded thereby into a plastid.
A method of producing P(3HB-co-3HV) copolymer comprises growing such plant, and recovering P(3HB-co-3HV) copolymer produced thereby.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which:

FIGS. 5A and 5B, genomic Southern blots hybridized with random primed probes generated from gel-excised E1α and E1β cDNAs respectively. ($\alpha^{32}$P)-dCTP was incorporated using an oligolabelling kit (Pharmacia, Uppsala, Sweden). The positions of λ DNA markers digested with Hind III are indicated to the left of the figure.

FIG. 8 shows the alignment of the deduced amino acid sequences of PDC E1α from plastid A.t. (SEQ ID NO:33), P. purplirea (SEQ ID NO:34), A. taliana (SEQ ID NO:35), H. sapiens II (SEQ ID NO:36), S. cerevisiae (SEQ ID NO:37), A. suum I (SEQ ID NO:38), M. capricolum (SEQ ID NO:39), B. subtilis (SEQ ID NO:40) and consensus sequence (SEQ ID NO:41). Abbreviations are the same as in FIG. 6. "*" indicates conserved, "•" non-conserved phosphorylation sites. "°" indicates the conserved Cys 62 of the mature H.s. E1α sequence.

FIG. 9 shows the alignment of the deduced amino acid sequences of PDC E1β from Plastid A.t. (SEQ ID NO:42), P. purpurea (SEQ ID NO:43), A. thaliana (SEQ ID NO:44), H. sapiens (SEQ ID NO:45), S. cerevisiae (SEQ ID NO:46), A. suum (SEQ ID NO:47), M. capricolum (SEQ ID NO:48), B. subtilis (SEQ ID NO:49) and a consensus sequence (SEQ ID NO:50). Abbreviations are the same as in FIG. 6.

FIG. 10 shows the alignment of the deduced amino acid sequences of various BCOADC E1β subunits, A.t. (SEQ ID NO:51), Human (SEQ ID NO:52), Bovine (SEQ ID NO: 53) and consensus (SEQ ID NO:54). Abbreviations are the same as in FIG. 6. "•" indicates conserved amino acids; "–" indicates a gap inserted to maximize homology.

FIG. 11 shows the nucleotide sequence of Arabidopsis thaliana pyruvate dehydrogenase complex E1α, SEQ ID NO:1.

FIG. 12 shows the amino acid sequence of Arabidopsis thaliana pyruvate dehydrogenase complex E1β, SEQ ID NO:2.

FIG. 13 shows the nucleotide sequence of Arabidopsis thaliana pyruvate dehydrogenase complex E1β, SEQ ID NO:3.

FIG. 14 shows the amino acid sequence of Arabidopsis thaliana pyruvate dehydrogenase complex E1β, SEQ ID NO:4.

FIG. 15 shows the nucleotide sequence of Arabidopsis thaliana branched chain oxoacid dehydrogenase complex E1αu, SEQ ID NO:11.

FIG. 16 shows the amino acid sequence of Arabidopsis thaliana branched chain oxoacid dehydrogenase complex E1α, SEQ ID NO:12.

FIG. 17 shows the nucleotide sequence of Arabidopsis thaliana branched chain oxoacid dehydrogenase complex E1β, SEQ ID NO:13.

FIG. 18 shows the amino acid sequence of Arabidopsis thaliana branched chain oxoacid dehydrogenase complex E1β, SEQ ID NO:14.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including those of the references cited within these primary references, are herein incorporated by reference in their entirety.

The production of P(3HB-co-3HV) in plants requires the substrates propionyl-CoA and acetyl-CoA, and three enzymes which convert these substrates to P(3HB-co-3HV): a β-ketothiolase, a β-ketoacyl-CoA reductase, and a PHA synthase. β-ketothiolase is normally present in the plant cytoplasm, but not in the plastids. Acetyl-CoA is normally present in the cytoplasm and the plastids. All of the other required components must be introduced into the plant, preferably into the plastids.

Figure 1:
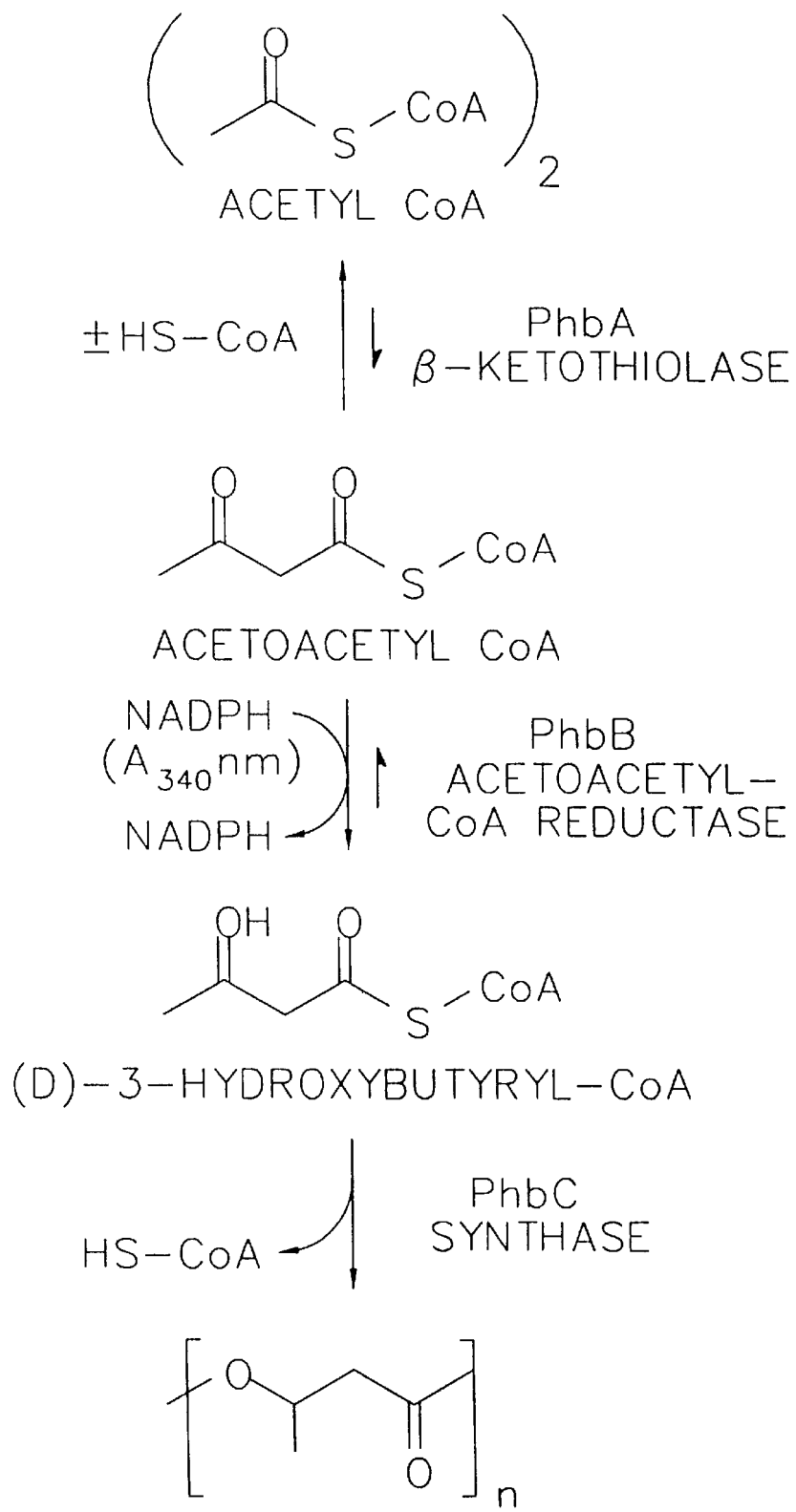
FIG. 1 shows the biochemical steps involved in the production of PHB from acetyl-CoA catalyzed by the *A. eutrophus* PHB biosynthetic enzymes.
Figure 2:
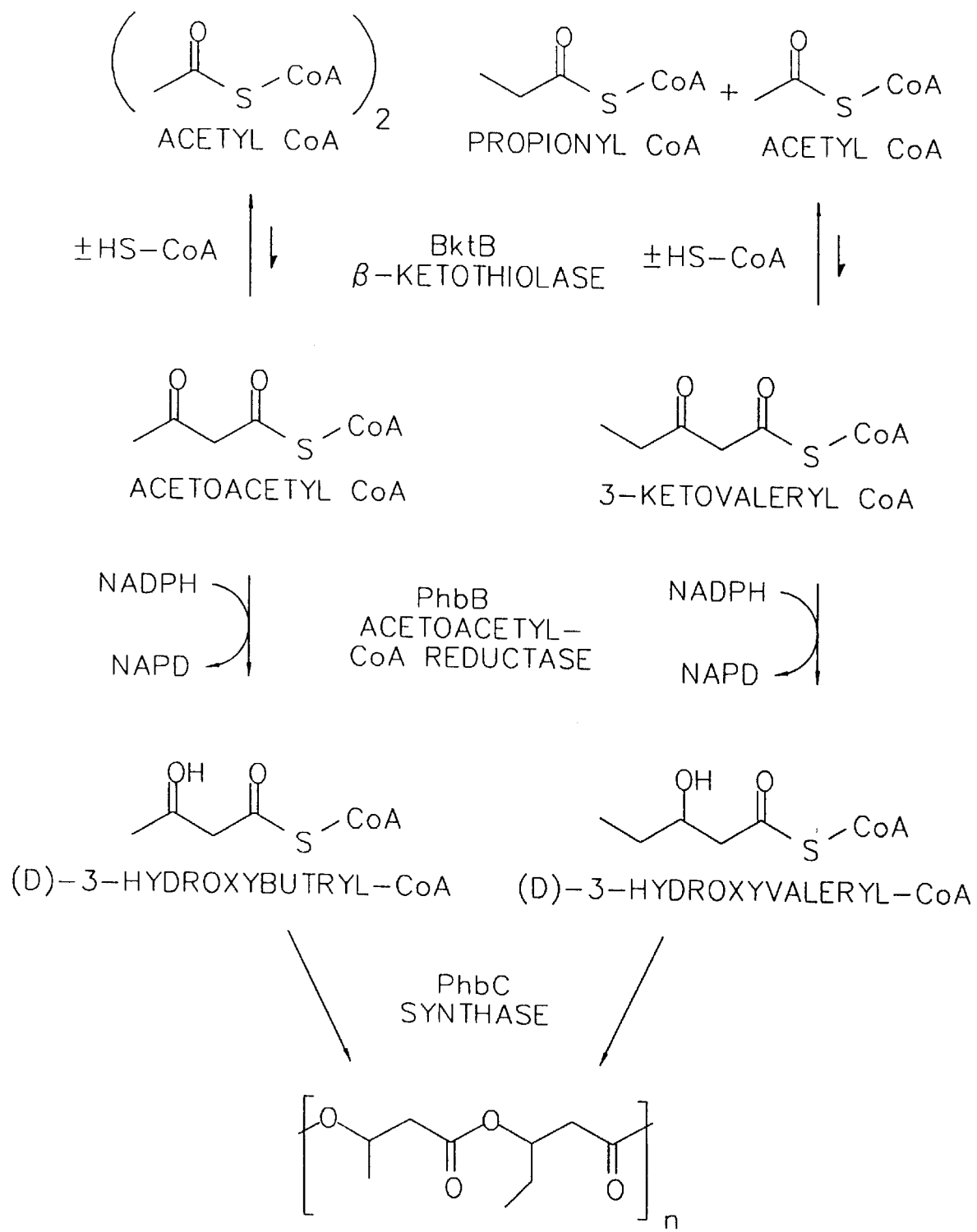
FIG. 2 shows the biochemical steps involved in the production of P(3HB-co-3HV) copolymer from acetyl-CoA and propionyl-CoA catalyzed by PHA biosynthetic enzymes of A. eutrophus.
Figure 3:
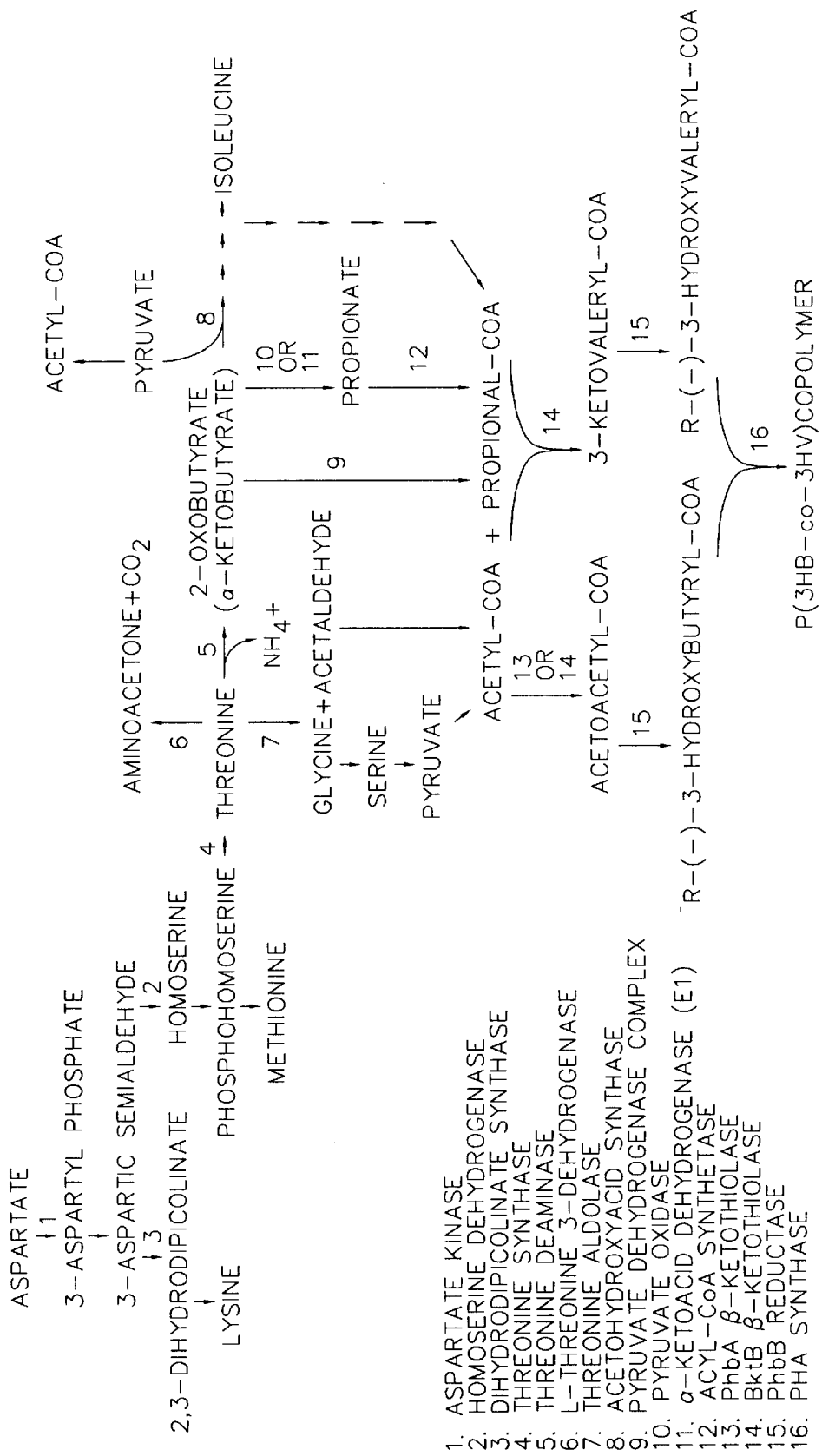
FIG. 3 summarizes the pathways discussed herein that are involved in the production of P(3HB-co-3HV) copolymer, including enzymes that can be used to enhance 2-oxobutyrate biosynthesis.

Gruys et al. (1998) discusses several ways in which 2-oxobutyrate can be provided in the plant. One way is through the manipulation of various wild-type and/or deregulated enzymes involved in the biosynthesis of aspartate family amino acids in order to increase threonine levels, thereby creating a larger substrate pool for threonine deaminase to convert to 2-oxobutyrate (FIG. 3), and wild-type or deregulated forms of enzymes, such as threonine deaminase, involved in the conversion of threonine to P(3HB-co-3HV) copolymer endproduct. Enzymes which can be manipulated to enhance the threonine pool include aspartate kinase, homoserine dehydrogenase, and threonine synthase. The threonine substrate pool can be enhanced by overexpression of these enzymes, or by the use of deregulated forms of these enzymes, such as lysine-deregulated aspartate kinase.

Threonine deaminase, which converts threonine to 2-oxobutyrate, is another enzyme which can be utilized in the production of 2-oxobutyrate. Deregulated mutants and natural deregulated forms of threonine deaminase can be used to increase 2-oxobutyrate pools at the site of copolymer biosynthesis.

Gruys et al. (1998), at Example 6, also discuss several ways in which the PDC and/or the BCOADC, or their substrate pools, can be manipulated to provide effective conversion of 2-oxobutyrate to propionyl-CoA. The native plastid PDC is able to perform this conversion at a low level. However, this complex can provide levels of propionyl-CoA sufficient for P(3HB-co-3HV) if the levels of 2-oxobutyrate are sufficient, or if portions of the BCOADC are employed to form a hybrid complex. The plastid PDC might also be genetically manipulated to be more effective in providing propionyl-CoA (Gruys et al., 1998).

The present invention provides nucleotide sequences that encode the E1α and E1β subunits, and the E2 component, of the plastid pyruvate dehydrogenase complex, and the E1α and E1β subunits, and the E2 component, of the branched chain oxoacid dehydrogenase complex of *Arabidopsis thaliana*. These nucleotide sequences and the enzymatic polypeptides encoded thereby can be introduced into plants in various combinations with coding sequences for the foregoing enzymes in order to enhance the conversion of threonine to 2-oxobutyrate, propionate, propionyl-CoA, β-ketovaleryl-CoA, and β-hydroxyvaleryl-CoA. Introduction into such plants of nucleic acid sequences encoding an appropriate β-keto-thiolase, a β-ketoacyl-CoA reductase, and a PHA synthase will permit such transgenic plants to utilize the increased β-hydroxyvaleryl-CoA substrate in the production of P(3HB-co-3HV) copolymer.

Definitions

The following definitions are provided to aid those skilled in the art in understanding the detailed description of the present invention.

"β-ketoacyl-CoA reductase" refers to a β-ketoacyl-CoA reducing enzyme that can convert a β-ketoacyl-CoA substrate to its corresponding β-hydroxyacyl-CoA product using, for example, NADH or NADPH as the reducing cosubstrate. An example is the PhbB acetoacetyl-CoA reductase of *A. eutrophus*.

"β-ketothiolase" refers to an enzyme that catalyzes the thiolytic cleavage of a β-ketoacyl-CoA, requiring free CoA, to form two acyl-CoA molecules. However, the term β-ketothiolase as used herein also refers to enzymes that catalyze the condensation of two acyl-CoA molecules to form β-ketoacyl-CoA and free CoA, i.e., the reverse of the thiolytic cleavage reaction.

"CoA" refers to coenzyme A.

"C-terminal" refers to the region of a peptide, polypeptide, or protein chain from the middle thereof to the end that carries the amino acid having a free α carboxyl group.

"Deregulated enzyme" refers to an enzyme that has been modified, for example by mutagenesis, wherein the extent of feedback inhibition of the catalytic activity of the enzyme by a metabolite is reduced such that the enzyme exhibits enhanced activity in the presence of said metabolite compared to the unmodified enzyme. Some organisms possess deregulated forms of such enzymes as the naturally occurring, wild-type form.

The term "DNA encoding" or "encoding DNA" refers to chromosomal DNA, plasmid DNA, cDNA, plastid DNA, or synthetic DNA which codes for expression for any of the enzymes discussed herein.

The term "genome" as it applies to bacteria encompasses both the chromosome and plasmids within a bacterial host cell. Unless specified, the term "genome" as it applies to plant cells encompasses not only chromosomal or nuclear DNA found within the nucleus, but organellar DNA found within subcellular components of the cell. DNAs of the present invention introduced into plant cells can therefore be either chromosomally-integrated or organelle-localized, unless specified (e.g. "plastid genome").

The term "mutein" refers to a mutant form of a peptide, polypeptide, or protein.

"N-terminal" refers to the region of a peptide, polypeptide, or protein chain from the amino acid having a free α-amino group to the middle of the chain.

"Operably linked" refers to two amino acid or nucleotide sequences wherein one of the sequences operates to affect a characteristic of the other sequence. In the case of nucleotide sequences, for example, a promoter "operably linked" to a structural coding sequence acts to drive expression of the latter.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the chloroplast genome, a circular DNA molecule that ranges in size from about 120 to about 217 kb, depending upon the plant species, and which usually contains an inverted repeat region (Fosket, 1994).

The term "polyhydroxyalkanoate (PHA) synthase" refers to enzymes that convert β-hydroxyacyl-CoAs to polyhydroxy-alkanoates and free CoA.

"Targeting sequence" refers to a nucleotide sequence which, when expressed (forming a "targeting peptide"), directs the export of an attached polypeptide to a particular cellular location, such as the chloroplast (e.g. "chloroplast targeting sequence"). The words "signal" or "transit" are equivalent to "targeting" in this context.

Production of Transgenic Plants Capable of Producing P(3HB-co-3HV) Copolymer

PHA synthesis in plants can be optimized in accordance with the present invention by expressing DNAs encoding β-ketothiolase, β-acyl-CoA reductase, and PHA synthase in conjunction with various portions and combinations of precursor-producing enzymes, including the sequences encoding portions of the plastid PDC and the BCOADC provided herein, as discussed in the Examples below.

Plant Vectors

In plants, transformation vectors capable of introducing encoding DNAs involved in PHA biosynthesis are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Plant transformation vectors also generally contain a selectable marker. Typical 5'–3' regulatory sequences include a transcription initiation start site, a ribosome binding site, an RNA processing signal, a transcription termination site, and/or a polyadenylation signal. Vectors for plant transformation have been reviewed in Rodriguez et al. (1988), Glick et al. (1993), and Croy (1993).

Plant Promoters

Plant promoter sequences can be constitutive or inducible, environmentally- or developmentally-regulated, or cell- or tissue-specific. Often-used constitutive promoters include the CaMV 35S promoter (Odell et al., 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter. Useful inducible promoters include heat-shock promoters (Ou-Lee et al., 1986; Ainley et al., 1990), a nitrate-inducible promoter derived from the spinach nitrite reductase gene (Back et al., 1991), hormone-inducible promoters (Yamaguchi-Shinozaki et al., 1990; Kares et al., 1990), and light-inducible promoters associated with the small subunit of RuBP carboxylase and LHCP gene families (Kuhlemeier et al., 1989; Feinbaum et al., 1991; Weisshaar et al., 1991; Lam and Chua, 1990; Castresana et al., 1988; Schulze-Lefert et al., 1989). Examples of useful tissue-specific, developmentally-regulated promoters include the β-conglycinin 7S promoter (Doyle et al., 1986; Slighton and Beachy, 1987), and seed-specific promoters (Knutzon et al., 1992; Bustos et al., 1991; Lam and Chua, 1991; Stayton et al., 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity.

A factor to be considered in the choice of promoters is the timing of availability of the necessary substrates during expression of the PHA biosynthetic enzymes. For example, if P(3HB-co-3HV) copolymer is produced in seeds from threonine, the timing of threonine biosynthesis and the amount of free threonine are important considerations. Karchi et al. (1994) have reported that threonine biosynthesis occurs rather late in seed development, similar to the timing of seed storage protein accumulation. For example, if enzymes involved in P(3HB-co-3HV) copolymer biosynthesis are expressed from the 7S seed-specific promoter, the timing of expression thereof will be concurrent with threonine accumulation.

Plant Transformation and Regeneration

A variety of different methods can be employed to introduce such vectors into plant protoplasts, cells, callus tissue, leaf discs, meristems, etc., to generate transgenic plants, including Agrobacterium-mediated transformation, particle gun delivery, microinjection, electroporation, polyethylene glycol-mediated protoplast transformation, liposome-mediated transformation, etc. (reviewed in Potrykus, 1991). In general, transgenic plants comprising cells containing and expressing DNAs encoding enzymes facilitating PHA biosynthesis can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the enzyme-encoding nucleotide sequence.

Constitutive overexpression of, for example, a deregulated threonine deaminase employing the CaMV 35S or FMV promoter might potentially starve plants of certain amino acids, especially those of the aspartate family. If such starvation occurs, the negative effects may be avoided by supplementing the growth and cultivation media employed in the transformation and regeneration procedures with appropriate amino acids. By supplementing the transformation/regeneration media with aspartate family amino acids (aspartate, threonine, lysine, and methionine), the uptake of these amino acids into the plant can reduce any potential starvation effect caused by an overexpressed threonine deaminase. Supplementation of the media with such amino acids might thereby prevent any negative selection, and therefore any adverse effect on transformation frequency, due to the overexpression of a deregulated threonine deaminase in the transformed plant.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the entire pathway into a single plant. Successful production of the PHA polyhydroxybutyrate in cells of Arabidopsis has been demonstrated by Poirier et al. (1992), and in plastids thereof by Nawrath et al. (1994).

Specific methods for transforming a wide variety of dicots and obtaining transgenic plants are well documented in the literature (Gasser and Fraley, 1989; Fisk and Dandekar, 1993; Christou, 1994; and the references cited therein).

Successful transformation and plant regeneration have been achieved in the monocots as follows: asparagus (*Asparagus officinalis*; Bytebier et al. 1987); barley (*Hordeum vulgarae*; Wan and Lemaux 1994); maize (*Zea mays*; Rhodes et al., 1988; Gordon-Kamm et al., 1990; Fromm et al., 1990; Koziel et al., 1993); oats (*Avena sativa*; Somers et al., 1992); orchardgrass (*Dactylis glomerata*; Horn et al., 1988); rice (*Oryza sativa*, including indica and japonica varieties; Toriyama et al., 1988; Zhang et al., 1988; Luo and Wu 1988; Zhang and Wu 1988; Christou et al., 1991); rye (*Secale cereale*; De la Pena et al., 1987); sorghum (*Sorghum bicolor*; Cassas et al. 1993); sugar cane (Saccharum spp.; Bower and Birch 1992); tall fescue (*Festuca arundinacea*; Wang et al. 1992); turfgrass (*Agrostis palustris*; Zhong et al., 1993); and wheat (*Triticum aestivum*; Vasil et al. 1992; Weeks et al. 1993; Becker et al. 1994).

Host Plants

Particularly useful plants for PHA copolymer production include those that produce carbon substrates which can be employed for PHA biosynthesis, including tobacco, wheat, potato, Arabidopsis, and high oil seed plants such as corn, soybean, canola, oil seed rape, sunflower, flax, and peanut. Polymers that can be produced in this manner include copolymers incorporating both short chain length and medium chain length monomers, such as P(3HB-co-3HV) copolymer.

If the host plant of choice does not produce the requisite fatty acid substrates in sufficient quantities, it can be modified, for example by mutagenesis or genetic transformation, to block or modulate the glycerol ester and fatty acid biosynthesis or degradation pathways so that it accumulates the appropriate substrates for PHA production.

Plastid Targeting of Expressed Enzymes for PHA Biosynthesis

PHA polymer can be produced in plants either by expression of the appropriate enzymes in the cytoplasm (Poirier et al., 1992) by the methods described above, or more preferably, in plastids, where higher levels of PHA production can be achieved (Nawrath et al., 1994). As demonstrated by the latter group, targeting of β-ketothiolase, acetoacetyl-CoA reductase, and PHB synthase to plastids of *Arabidopsis thaliana* results in the accumulation of high levels of PHB in the plastids without any readily apparent deleterious effects on plant growth and seed production. As branched-chain amino acid biosynthesis occurs in plant plastids (Bryan, 1980; Galili, 1995), overexpression therein of plastid-targeted enzymes, including a deregulated form of threonine deaminase, is expected to facilitate the production of elevated levels of 2-oxobutyrate and propionyl-CoA. The latter can be condensed with acetyl-CoA by β-ketothiolase to form 3-ketovaleryl-CoA, which can then be further metabolized by a β-keto-acyl-CoA reductase to 3-hydroxyvaleryl-CoA, the precursor of the C5 subunit of P(3HB-co-3HV) copolymer. As there is a high carbon flux through acetyl-CoA in plastids, especially in seeds of oil-accumulating plants such as oilseed rape (*Brassica napus*), canola (*Brassica rapa, Brassica campestris, Brassica carinata*, and *Brassica juncea*), soybean (*Glycine max*), flax (*Linum usitatissimum*), and sunflower (*Helianthus annuus*) for example, targeting of the gene products of desired encoding DNAs to leucoplasts of seeds, or transformation of seed leucoplasts and expression therein of these encoding DNAs, are attractive strategies for achieving high levels of PHA biosynthesis in plants.

All of the enzymes discussed herein can be modified for plastid targeting by employing plant cell nuclear transformation constructs wherein DNA coding sequences of interest are fused to any of the available transit peptide sequences capable of facilitating transport of the encoded enzymes into plant plastids (partially summarized in von Heijne et al., 1991), and driving expression by employing an appropriate promoter. The sequences that encode a transit peptide region can be obtained, for example, from plant nuclear-encoded plastid proteins, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present invention are not critical as long as delivery into a plastid is obtained. Proteolytic processing within the plastid then produces the mature enzyme. This technique has proven successful not only with enzymes involved in PHA synthesis (Nawrath et al., 1994), but also with neomycin phosphotransferase II (NPT-II) and CP4 EPSPS (Padgette et al., 1995), for example.

Of particular interest are transit peptide sequences derived from enzymes known to be imported into the leucoplasts of seeds. Examples of enzymes containing useful transit peptides include those related to lipid biosynthesis (e.g., subunits of the plastid-targeted dicot acetyl-CoA carboxylase, biotin carboxylase, biotin carboxyl carrier protein, α-carboxytransferase, plastid-targeted monocot multifunctional acetyl-CoA carboxylase (Mr, 220,000); plastidic subunits of the fatty acid synthase complex (e.g., acyl carrier protein (ACP), malonyl-ACP synthase, KASI, KASII, KASIII, etc.); steroyl-ACP desaturase; thioesterases (specific for short, medium, and long chain acyl ACP); plastid-targeted acyl transferases (e.g., glycerol-3-phosphate: acyl transferase); enzymes involved in the biosynthesis of aspartate family amino acids; phytoene synthase; gibberellic acid biosynthesis (e.g., ent-kaurene synthases 1 and 2); sterol biosynthesis (e.g., hydroxy methyl glutaryl-coA reductase); and carotenoid biosynthesis (e.g., lycopene synthase).

Exact translational fusions to the transit peptide of interest may not be optimal for protein import into the plastid. By creating translational fusions of any of the enzymes discussed herein to the precursor form of a naturally imported protein or C-terminal deletions thereof, one would expect that such translational fusions would aid in the uptake of the engineered precursor protein into the plastid. For example, Nawrath et al., (1994) used a similar approach to create the vectors employed to introduce the PHB biosynthesis genes of *A. eutrophus* into Arabidopsis.

It is therefore fully expected that targeting of the enzymes discussed herein to leaf chloroplasts or seed plastids such as leucoplasts by fusing transit peptide gene sequences thereto will further enhance in vivo conditions for the biosynthesis of PHAs, especially P(3HB-co-3HV) copolymer, in plants.

Plastid Transformation for Expression of Enzymes Involved in PHA Biosynthesis

Alternatively, enzymes facilitating the biosynthesis of metabolites such as threonine, 2-oxobutyrate, propionyl-CoA, 3-ketovaleryl-CoA, 3-hydroxy-valeryl-CoA, and PHAs discussed herein can be expressed in situ in plastids by direct transformation of these organelles with appropriate recombinant expression constructs. Constructs and methods for stably transforming plastids of higher plants are well known in the art (Svab et al., 1990; Svab et al., 1993; Staub et al., 1993; Maliga et al., U.S. Pat. No. 5,451,513; PCT International Publications WO 95/16783, WO 95/24492, and WO 95/24493). These methods generally rely on particle gun delivery of DNA containing a selectable marker in addition to introduced DNA sequences for expression, and targeting of the DNA to the plastid genome through homologous recombination. Transformation of a wide variety of different monocots and dicots by particle gun bombardment is routine in the art (Hinchee et al., 1994; Walden and Wingender, 1995).

DNA constructs for plastid transformation generally comprise a targeting segment comprising flanking DNA sequences substantially homologous to a predetermined sequence of a plastid genome, which targeting segment enables insertion of DNA coding sequences of interest into the plastid genome by homologous recombination with said predetermined sequence; a selectable marker sequence, such as a sequence encoding a form of plastid 16S ribosomal RNA that is resistant to spectinomycin or streptomycin, or that encodes a protein which inactivates spectinomycin or streptomycin (such as the aadA gene), disposed within said targeting segment, wherein said selectable marker sequence confers a selectable phenotype upon plant cells, substantially all the plastids of which have been transformed with said DNA construct; and one or more DNA coding sequences of interest disposed within said targeting segment relative to said selectable marker sequence so as not to interfere with conferring of said selectable phenotype. In addition, plastid expression constructs also generally include a plastid promoter region and a transcription termination region capable of terminating transcription in a plant plastid, wherein said regions are operatively linked to the DNA coding sequences of interest.

A further refinement in chloroplast transformation/expression technology that facilitates control over the timing and tissue pattern of expression of introduced DNA coding sequences in plant plastid genomes has been described in PCT International Publication WO 95/16783. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promoter specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase. The introduced DNA coding sequence can be a single encoding region, or may contain a number of consecutive encoding sequences to be expressed as an engineered or synthetic operon. The latter is especially attractive where, as in the present invention, it is desired to introduce multigene biochemical pathways into plastids. This approach is not practical using standard nuclear transformation techniques since each gene introduced therein must be engineered as a monocistron, including an encoded transit peptide and appropriate promoter and terminator signals. Individual gene expression levels may vary widely among different cistrons, thereby possibly adversely affecting the overall biosynthetic process. This can be avoided by the chloroplast transformation approach.

Production of Transgenic Plants Comprising Genes for PHA Biosynthesis

Plant transformation vectors capable of delivering DNAs (genomic DNAs, plasmid DNAs, cDNAs, or synthetic DNAs) encoding PHA biosynthetic enzymes and other enzymes for optimizing substrate pools for PHA biosynthesis as discussed in Examples 1–7 herein can be easily designed. Various strategies can be employed to introduce these encoding DNAs to produce transgenic plants capable of biosynthesizing high levels of PHAs, including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.

2. Sequentially transforming plants with plasmids containing each of the encoding DNAs of interest, respectively.

3. Simultaneously cotransforming plants with plasmids containing each of the encoding DNAs, respectively.

4. Transforming plants with a single plasmid containing two or more encoding DNAs of interest.

5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al., 1994; PCT International Publication WO 93/02187). Similar strategies can be employed to produce bacterial host cells engineered for optimal PHA production.

In methods 2 and 3, the use of vectors containing different selectable marker genes to facilitate selection of plants containing two or more different encoding DNAs is advantageous. Examples of useful selectable marker genes include those conferring resistance to kanamycin, hygromycin, sulphonamides, glyphosate, bialaphos, and phosphinothricin.

Stability of Transgene Expression

As several overexpressed enzymes may be required to produce optimal levels of substrates for copolymer formation, the phenomenon of co-suppression may influence transgene expression in transformed plants. Several strategies can be employed to avoid this potential problem (Finnegan and McElroy, 1994).

One commonly employed approach is to select and/or screen for transgenic plants that contain a single intact copy of the transgene or other encoding DNA (Assaad et al., 1993; Vaucheret, 1993; McElroy and Brettell, 1994). Agrobacterium-mediated transformation technologies are preferred in this regard.

Inclusion of nuclear scaffold or matrix attachment regions (MAR) flanking a transgene has been shown to increase the level and reduce the variability associated with transgene expression in plants (Stief et al., 1989; Breyne et al., 1992; Allen et al., 1993; Mlynarova et al., 1994; Spiker and Thompson, 1996). Flanking a transgene or other encoding DNA with MAR elements may overcome problems associated with differential base composition between such transgenes or encoding DNAs and integrations sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs (Register et al., 1994). Site-specific recombination in which the endogenous copy of a gene is replaced by the same gene, but with altered expression characteristics, should obviate this problem (Yoder and Goldsbrough, 1994).

Any of the foregoing methods, alone or in combination, can be employed in order to insure the stability of transgene expression in transgenic plants of the present invention.

Cloning of Plastid Pyruvate Dehydrogenase Complex and Branched Chain Oxoacid Dehydrogenase Complex Subunits and Components The present invention provides nucleotide sequences that encode the E1α and E1β subunits, and the E2 component, of the plastid pyruvate dehydrogenase complex, as well as the E1α and E1β subunits, and the E2 component, of the branched chain oxoacid dehydrogenase complex, of *Arabi-*

*dopsis thaliana*. These sequences can be cloned by any appropriate method known in the art. For example, cDNA clones of known components of similar enzymes from other species can be utilized to screen a cDNA library from which the cDNA for the enzyme component is desired. Sources from which the plastid PDC E1α and E1β cDNAs can be obtained include the analogous enzyme-encoding cDNAs from the red alga *Porphyra purpurea*; for the E2 component of the plastid pyruvate dehydrogenase, the analogous enzyme gene from the cyanobacterium Synechocystis sp. can be used. The cDNA for the E1α of a BCOADC can be isolated by identifying cDNAs which have significant homology to analogous tomato, human and bovine BCOADC E1α sequences. Similarly, the E1β and the E2 components of a BCOADC can be isolated by comparing the similarity of candidate sequences with the human and bovine BCOADC E1β and E2 components, respectively. A cDNA library for the isolation of these components can be an expressed sequence tag library, for example one comprising cDNA from *Arabidopsis thaliana*.

The cloned cDNAs for the plastid PDC and the BCOADC components can be sequenced in order to determine the nucleotide sequence and deduce the amino acid sequence for these enzymes. The sequences of these cDNAs can be determined by any method known in the art. Methods for the determination of various portions of the sequenced cDNA, such as a plastid targeting sequence, are also well known in the art.

Engineering Plants to Produce Propionyl-CoA in Plastids

The production of the P(3HB-co-3HV) precursor propionyl-CoA in plastids requires the presence of two elements which are not present, or which are present at very low levels, in the plastids of wild-type plants: 2-oxobutyrate, and enzymes which will convert 2-oxobutyrate into propionyl-CoA.

As noted above, Gruys et al. (1998) discusses several methods for the production of 2-oxobutyrate in plastids. These include:

Overexpression of threonine deaminase;

Overexpression of aspartate kinase and threonine deaminase; and

Overexpression of aspartate kinase, homoserine dehydrogenase, and threonine deaminase.

The overexpression of these enzymes can be accomplished through the transformation into plants of nucleotide sequences encoding these enzymes, operably linked to a plant promoter, such as the cauliflower mosaic virus (CaMV) 35s promoter, or any other promoter known in the art which causes overexpression of such enzymes in plants.

The expression of these and other enzymes in plastids can be achieved in at least two ways:

1. By transforming coding sequences for these enzymes directly into the plastid genome in such a way that they are incorporated into the plastid genome. Constructs and methods for stably transforming plastids of higher plants are well known in the art (for example, Svab et al., 1990; Svab et al., 1993; Staub et al., 1993; Maliga et al., U.S. Pat. No. 5,451,513; PCT International Publications WO 95/16783, WO 95/24492, and WO 95/24493). These methods generally rely on particle gun delivery of DNA containing a selectable marker in addition to introduced DNA sequences for expression, and targeting of the DNA to the plastid genome through homologous recombination.

2. By creating a plant transformation vector comprising a coding sequence for the enzyme operably linked to a plastid targeting sequence, then transforming this vector into the plant. All of the enzymes discussed herein can be modified for plastid targeting by employing plant cell nuclear transformation constructs wherein DNA coding sequences of interest are fused to any of the available targeting peptide sequences capable of facilitating transport of the encoded enzymes into plant plastids, and driving expression by employing an appropriate promoter. Examples of plastid targeting peptides are provided in Table 1 and in von Heijne et al. (1991). The sequences that encode a targeting peptide region can be obtained, for example, from plant nuclear-encoded plastid proteins, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a targeting peptide effective in transport to plastids can include all or a portion of the encoding sequence for a particular targeting peptide, and can also contain portions of the mature protein encoding sequence associated with a particular targeting peptide. Numerous examples of targeting peptides that can be used to deliver target proteins into plastids exist, and the particular targeting peptide encoding sequences useful in the present invention are not critical as long as delivery into a plastid is obtained. Proteolytic processing within the plastid then produces the mature enzyme. This technique has proven successful not only with enzymes involved in PHA synthesis (Nawrath et al., 1994), but also with neomycin phosphotransferase II (NPT-II) and CP4 EPSPS (Padgette et al., 1995), for example.

TABLE 1

Examples of plastid proteins from various species with known plastid targeting sequences that can be used to target proteins to plastids Chloroplast Targeting Peptides

*Arabidopsis thaliana*:

5-enolpyruvyl-shikimate-3-phosphate synthase
Rubisco activase
Rubisco small subunit
Tryptophan synthase

*Brassica napus*:

Acyl carrier protein
Plastid chaperonin-60

*Pisum sativum*:

Carbonic anhydrase
Chloroplast stromal HSP70
Glutamine synthetase
Rubisco small subunit Reference: von Heijne, G.; Hirai, T.; Klosgen, R. B.; Steppuhn, J.; Bruce, B.; Keegstra, K.; Herrmann, R. (1991) CHLPEP-A database of chloroplast transit peptides. *Plant Molecular Biology Reporter* 9:104–126.

Engineering Plants to Produce Poly(3-hydroxybutyrate-3-hydroxyvalerate) Copolymer Plants which produce P(3HB-co-3HV) can be created by engineering them to produce 2-oxobutyrate, to convert 2-oxobutyrate to propionyl-CoA, and to synthesize P(3HB-co-3HV) from propionyl-CoA and acetyl-CoA. Methods for producing plants which synthesize 2-oxobutyrate are discussed above. Such plants can be modified to convert 2-oxobutyrate to propionyl-CoA in the manner discussed below.

The nucleotide sequences of the BCOADC E1α and E1β subunits, and that of the E2 component, are provided herein as a means to effect the conversion of 2-oxobutyrate to propionyl-CoA in plastids containing the 2-oxobutyrate substrate. It is not necessary to provide the E3 component since the E3 components of all of the α-ketoacid dehydrogenase complexes are probably interchangeable. The E3 subunit already present in the plastid PDC thus almost certainly functions with plastid-targeted BCOADC subunits. The nucleotide sequences of the plastid PDC E1α and E1β subunits, and the E2 component, provide sources of plastid targeting sequences. These plastid PDC sequences can also be genetically manipulated to enhance their ability to convert 2-oxobutyrate to propionyl-CoA, as suggested by Gruys et al. (1998).

The nucleotide sequences encoding the BCOADC E1α and E1β subunits, and the E2 component, can be directly transformed into the plastid genome by the methods discussed above. Alternatively, the BCOADC E1 and E2 nucleotide sequences can be transformed into the plant nuclear genome, wherein the enzyme coding sequences are operably linked to a plastid targeting sequence by methods known in the art. See Example 7. Useful plastid targeting sequences include those from the plastid PDC. These targeting sequences from *Arabidopsis thaliana* are disclosed in Examples 1 and 2, below.

As another alternative for utilizing a BCOADC for the conversion of 2-oxobutyrate to propionyl-CoA in plastids, a nucleotide sequence encoding the BCOADC E1β subunit can be engineered to utilize the PDC E2 component which is already present in the plastids. The BCOADC E1β subunit can be modified such that the native E2 binding region thereof is replaced with the E2 binding region of the plastid PDC E1β subunit. The nucleotide sequences encoding the modified BCOADC E1β subunit and the BCOADC E1α subunit can also be operably linked to a plastid targeting sequence. The modified nucleotide sequences for these two subunits (α and β) of the BCOADC E1 component can then be inserted into plants by standard plant transformation methods, where they are translated in the cytoplasm. The enzymes are then transported to the plastid where they combine with the plastid PDC E2 and E3 components, and catalyze the conversion of 2-oxobutyrate to propionyl-CoA. See Example 6 below.

The conversion of propionyl-CoA and acetyl-CoA to P(3HB-co-3HV) requires a β-ketothiolase, a β-ketoacyl-CoA reductase, and a PHA synthase. Nucleotide sequences encoding these enzymes can be incorporated into the plastid genome directly, or into the nuclear genome, with operably linked plastid targeting sequences, utilizing the same well-known methods as previously discussed. Preferred β-ketothiolases are BktB and pAE65 from *A. eutrophus*, and *Zoogloea ramigera* β-ketothiolases "A" and "B", as disclosed in Gruys et al (1998). Preferred β-ketoacyl-CoA reductases and PHA synthases include those from *A. eutrophus*, encoded by the phbB and phbC genes, respectively. However, the use of other β-ketothiolases which are able to utilize propionyl-CoA, and the use of other β-ketoacyl-CoA reductases and PHA synthases are within the scope of this invention. Included are those enzymes from, for example, *Alcaligenes faecalis*, Aphanothece sp., *Azotobacter vinelandii, Bacillus cereus, Bacillus megaterium, Beijerinkia indica, Derxia gummosa*, Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum*, and *Thiocapsa pfennigii*.

P(3HB-co-3HV) Copolymer Composition

The P(3HB-co-3HV) copolymers of the present invention can comprise about 75–99% 3HB and about 1–25% 3HV based on the total weight of the polymer. More preferably, P(3HB-co-3HV) copolymers of the present invention comprise about 85–99% 3HB and about 1–15% 3HV. Even more preferably, such copolymers comprise about 90–99% 3HB and about 1–10% 3HV. P(3HB-co-3HV) copolymers comprising about 4%, about 8%, and about 12% 3HV on a weight basis possess properties that have made them commercially attractive for particular applications. One skilled in the art can modify P(3HB-co-3HV) copolymers of the present invention by physical or chemical means to produce copolymer derivatives having desirable properties different from those of the plant-produced copolymer.

Optimization of P(3HB-co-3HV) copolymer production by the methods discussed herein is expected to result in yields of copolymer in the range of from at least about 1% to at least about 20% of the fresh weight of the plant tissue, organ, or structure in which it is produced.

The following examples illustrate the invention, but are not to be taken as limiting the various aspects of the invention so illustrated.

Conventional methods of gene isolation, molecular cloning, vector construction, etc., are well known in the art and are summarized in Sambrook et al., 1989, and Ausubel et al., 1989 and 1994. One skilled in the art can readily repeat the methods and reproduce the compositions described herein without undue experimentation. The various DNA sequences, fragments, etc., necessary for this purpose can be readily obtained as components of commercially available plasmids, or synthesized by well known methods, or are otherwise well known in the art and publicly available.

EXAMPLE 1

Cloning and Sequencing cDNA Encoding the E1α and E1β Subunits of the *Arabidopsis thaliana* Plastid Pyruvate Dehydrogenase Complex Expressed sequence tag (EST) clones (Reith et al., 1995) from the Arabidopsis Biological Resource Center (ABRC) at Ohio State University were used to isolate full-length cDNAs for both the plastid E1α and E1β subunits from an *A. thaliana* cDNA library. Two clones (GenBank accessions T75600 and N65566) were identified as potentially encoding the plastid E1α and E1β subunits as follows.

Oligonucleotides were designed based on sequences common to *P. purpurea* odpA and odpB and the two Arabidopsis EST sequences and synthesized (all recited in the 5'–3' direction):

E1α: 5' primer, CGGTACtCAAGTCTGACTCT-GTCGTT (SEQ ID NO:7);

3' primer, CCTTCGAUAGGTTCCATCTCCGAAAAA (SEQ ID NO:8);

E1β: 5' primer, CGGTACtCTTCGAGGCTCTTCAG-GAA (SEQ ID NO:9);

3' primer, CCTTCGAuACGGGCCTTAGACCAGT (SEQ ID NO:10).

The symbols denote restriction sites (t: Kpn I, and u: Hind III) added for subcloning. Thermal cycling was used to amplify cDNA fragments from *A. thaliana* using first strand cDNA. Thermal cycling reactions (50 μl total volume) contained 10 mM Tris-HCl, pH 7.9, 1.25 mM MgCl$_2$, 25 μM dNTPs, 5 units Taq polymerase (Promega, Madison, Wis.), 2 μg A. thaliana first strand cDNA, and 10 ng of each primer. Thermal cycling was performed with a Perkin-Elmer model 480, with rapid ramp times set at 1° C./s. Cycling conditions were 94° C. for 20 s, 50° C. for 30 s, 72° C. for 2 min with 6 s extensions each cycle and 30 rounds of cycling. Under these conditions, products containing 288 base pairs (E1α) and 215 base pairs (E1β) were obtained. The products were subcloned into pGEMT (Promega, Madison, Wis.) and sequenced to confirm their identity. Thermal cycling was also used to generate probes radiolabelled with ($\alpha^{32}$P)-dCTP, using reaction mixtures identical to those previously described except for a 1000-fold reduction in the concentration of non-radioactive dCTP. Before use, the probes were desalted using Sephadex G-50 columns to remove unincorporated nucleotides. An Arabidopsis cDNA library (λ-PRL2, obtained from the ABRC) was plated at a density of 2.25× $10^4$ plaques per plate for a total of 2.25×$10^5$ plaques. BioTrace NT nylon filters (Gelman, Ann Arbor, Mich.) were used for plaque-lifts and were processed according to the manufacturer's specifications. Hybridizations were performed according to *Current Protocols in Molecular Biology* (Ausubel et al., 1994). After three rounds of screening, 7 potential E1α and 12 potential E1β cDNA clones were isolated, ranging in size from 1100 to 1550 base pairs. Plaque-purified λ phage were treated according to the manufacturer's instructions (Gibco BRL, Gaithersburg, Md.) in order to excise the pZL-1 recombinant clones.

DNA sequencing was performed using an ABI prism Model 377 sequencer, and analyzed using IntelliGenetics GeneWorks DNA analysis program version 2.5 on a Macintosh computer. Dye-deoxy terminating cycle sequencing reactions were carried out on both strands of full-length cDNA inserts and deletion fragments derived therefrom.

DNA isolation and Northern and Southern blotting were carried out according to *Current Protocols in Molecular Biology* (Sections 2.9.1, 4.3.1 and 4.9.1; Ausubel et al., 1994). RNA isolation was accomplished with the RNAgents total RNA isolation kit (Promega, Madison, Wis.). Northern blot prehybridization (3 h), hybridization (12 h), and 4 washes were done with 2.5×SSPE (1×=0.15 mM NaCl, 0.02 mM $Na_2PO_4$, 2 μM EDTA, pH 7.4), 1% SDS, 1% non-fat dry milk, and 250 μg/ml salmon sperm DNA at 68° C. Blots were exposed on Kodak X-OMAT/AR film (Rochester, N.Y.) at −70° C. with an intensifying screen.

Among the genes present in the *P. purpurea* plastome are two open reading frames, odpA and odpB, encoding proteins 32% identical to the Arabidopsis mitochondrial E1α and E1β subunits (Grof et al., 1995; Leuthy et al., 1994; Leuthy et al., 1995). Attempts to use cloned mitochondrial PDC cDNAs as probes to identify plastid sequences have been unsuccessful. Based upon the odpA and odpB sequences, two EST clones (accessions T75600 and N65566) which appear to encode proteins more highly related to the *P. purpurea* odpA and odpB sequences than to the Arabidopsis mitochondrial sequences were used to isolate two cDNAs as potential E1α and E1β clones.

The nucleotide sequence of the Arabidopsis plastid PDC E1α cDNA (Genbank Accession No. U80185) is shown in FIG. 11 and as SEQ ID NO:1. E1α cDNA (1530 bp) has a 106 bp 5' untranslated region, a 1284 bp open reading frame encoding a polypeptide of 428 amino acids (FIG. 12 and SEQ ID NO:2), and a 140 bp 3' untranslated region. The nucleotide sequence of the Arabidopsis plastid PDH E1β cDNA (Genbank Accession No. U80186) is shown in FIG. 13 and as SEQ ID NO:3. The E1β cDNA (1441 bp) has a 6 bp 5' untranslated region, a 1218 bp open reading frame encoding a polypeptide of 406 amino acids (Appendix D and SEQ ID NO:4), and a 217 bp 3' untranslated region. The calculated molecular weight and isoelectric point values for the E1α and E1β polypeptides encoded by the open reading frames are 47,120 with a pI of 7.25, and 44,208 with a pI of 5.89, respectively. The deduced amino acid sequence for E1α has 61%, and E1β 68%, identity with *P. purpurea* odpA and odpB, respectively.

The first 68 residues of E1α and the first 73 residues of E1β exhibit characteristics of chloroplast targeting peptides but not those of mitochondrial targeting sequences (Gavel et al., 1990; von Heijne et al., 1989). To determine structural motifs of the targeting peptides, we used the GeneWorks (IntelliGenetics, Mountain View, Calif.) protein algorithm to identify possible α-helix and β-strands. Both plastid E1α and E1β have the potential to form amphiphilic β-strands consistent with plastid targeting sequences, but did not fit the amphiphilic α-helix which is characteristic of mitochondrial targeting sequences.

Tables 2 and 3 show the alignment of the deduced amino acid sequences of PDH E1α and E1β. Abbreviations are the same as in FIG. 7. * indicates conserved, • non-conserved phosphorylation sites. ° indicates the conserved Cys 62 of the mature *H.s.* E1α sequence.

Overall, there is 28% sequence identity between Arabidopsis plastid PDC E1α and its mammalian counterparts. However, in specific regions, the degree of sequence conservation is much higher. The PDH component of PDC requires thiamine pyrophosphate (TPP) as a cofactor for decarboxylation of pyruvate (Patel et al., 1990). It has been reported that TPP binds to the E1α subunit of mammalian PDH at a site containing a structural motif common to pyrophosphate-binding enzymes (Reed, 1974). A similar motif (50% identity with the bovine E1α TPP-binding domain) is found in the *A. thaliana* plastid E1α sequence at residues 160–213 (Table 2).

A highly conserved Cys residue (Cys 62 of mature human E1α, Table 2) has been identified in eukaryotic PDH E1α sequences, and it has been proposed that this Cys is an essential component of the enzyme's active site (Ali et al., 1993). The *A. thaliana* plastid E1α sequence contains a similar motif, i.e. the same immediate flanking residues at 112–116, but the otherwise conserved Cys is replaced with a Val (Table 2).

Mitochondrial PDCs are regulated in part by reversible phosphorylation of three conserved Ser residues in the E1α sequence by a specific, complex-associated PDH-kinase (Reed, 1974). The Ser residues phosphorylated in mammalian mitochondrial PDH are also conserved in the plant mitochondrial (Luethy et al., 1995), yeast (Behal et al., 1989), and nematode (Johnson et al., 1992) amino acid sequences. However, while the plant mitochondria PDC is reversibly phosphorylated (Randall et al., 1989; Randall et al., 1996), all evidence to date indicates that plastid PDC activity is not regulated by phosphorylation (Camp et al., 1985). Despite this difference, the regulatory Ser residues and their flanking sequences are present in the plastid E1α sequence (Table 2). Korotchkina and Patel (1995) have reported the results from mutagenesis of these phosphorylation sites, and concluded that site one is closer to the active site or lies on the pathway to the main catalytic conformational change. This might explain why this region is so highly conserved. The amino acid-motif corresponding to phosphorylation site one in mitochondrial PDH sequences is present in the plastid polypeptide (Tyr 320-Pro 330 or Tyr 287-Pro 297 in the *H. s.* sequence, Table 2). Two of the four substitutions are by residues with conserved properties. The sequence of the plastid E1α corresponding to phosphorylation site two lacks a Ser and the region is dominated by five acidic and two basic residues (Asp 329-Asp 339). The Arabidopsis plastid E1α sequence contains a Ser at site 3 (Ala 259-Ala 267), but the flanking residues are dissimilar to the mammalian site 3 (Table 2). While two of the three Ser are in the appropriate positions, it is most likely then that plastid PDC is not regulated by phosphorylation due to the lack of plastid PDH-kinase (Camp et al., 1985).

Wexler et al. (1991) compared alignments of three PDH and three branched-chain α-keto acid dehydrogenase sequences. Among E1β sequences, four regions of sequence conservation were observed. Region one, the proposed E2 interaction site, is present in the Arabidopsis plastid PDH E1β sequence (Table 3). Conserved regions two and three share high homology with other decarboxylating enzymes, suggesting a role in decarboxylation of pyruvate (Wexler et al., 1991). A functional role has not yet been attributed to region four (Table 3). Eswaran et al. (1995) have described Arg 239 as being an essential residue near or at the active site of the bovine E1β. This residue is conserved throughout the eukaryotic PDH sequences (e.g., Arg 269 of *H. s.* sequence in Table 3), and is present in the *A. thaliana* plastid E1β sequence at position 318.

Figure 4:
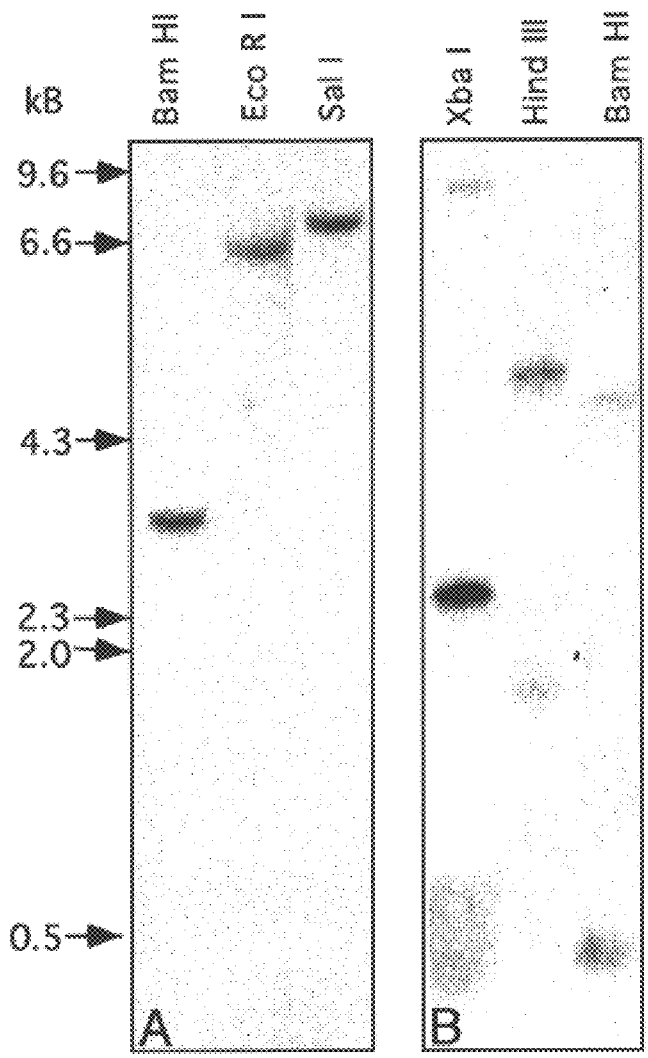
FIG. 4 shows Southern analyses of genomic DNA isolated from mature A. thaliana leaves. Each lane was loaded with 10 μg of DNA digested with BamHI, Hind III, Sal I, Eco RI or Xba I as indicated.

The genomic organization of Arabidopsis E1α and E1β was determined by Southern blot analysis. An E1α cDNA probe hybridized to a single restriction fragment in each lane, suggesting one gene (FIG. 4A). An E1β cDNA probe, on the other hand, hybridized to multiple fragments in a pattern consistent with the restriction digest of E1β cDNA (data not shown). The Xba I lane contained multiple hybridizing bands which could be due to a second gene or an intron containing an Xba I restriction site (FIG. 4B).

Figure 5:
FIG. 5 shows Northern blot analyses of A. thaliana RNA. Total RNA was isolated from young leaves of A. thaliana plants. 10 μg of total RNA was run on formaldehyde gels then transferred to nylon membranes. Probes were prepared as described in the legend for FIG. 5. RNA markers were used to determine the sizes of the hybridizing bands.

In order to evaluate expression of the *A. thaliana* plastid PDH genes, 10 μg total RNA obtained from young leaves were resolved by formaldehyde gel electrophoresis. Northern blot analyses confirmed the expression of a single mRNA species of 1.65 kb for E1α and 1.5 kb for E1β (FIGS. 5A and 5B).

The two cDNAs reported here have been identified as encoding plastid rather than mitochondrial proteins based on their high homology with the *P. purpurea* chloroplast genes, the presence of N-terminal sequences characteristic of plastid targeting peptides, and their relatively low homology with plant mitochondrial E1 subunits (Grof et al., 1995; Leuthy et al., 1994; Leuthy et al., 1995). Assessments of the mature N-terminal sequences were based on homology with the mature odp and mitochondrial E1 sequences.

The mature *A. thaliana* plastid E1α and E1β amino acid sequence have the highest homology (68%) with the *P. purpurea* chloroplast odpA and odpB sequences, respectively, but only 31 and 32% identity with the respective *A. thaliana* mitochondrial E1 sequences (Tables 2 and 3). The homology with other eukaryotic mitochondrial E1 sequences is lower yet. Additionally, a monoclonal antibody prepared against mitochondrial E1α does not recognize chloroplastic E1α (Luethy et al., 1995) nor does the monoclonal antibody recognize the recombinant plastid E1α on immunoblots.

Figure 6A:
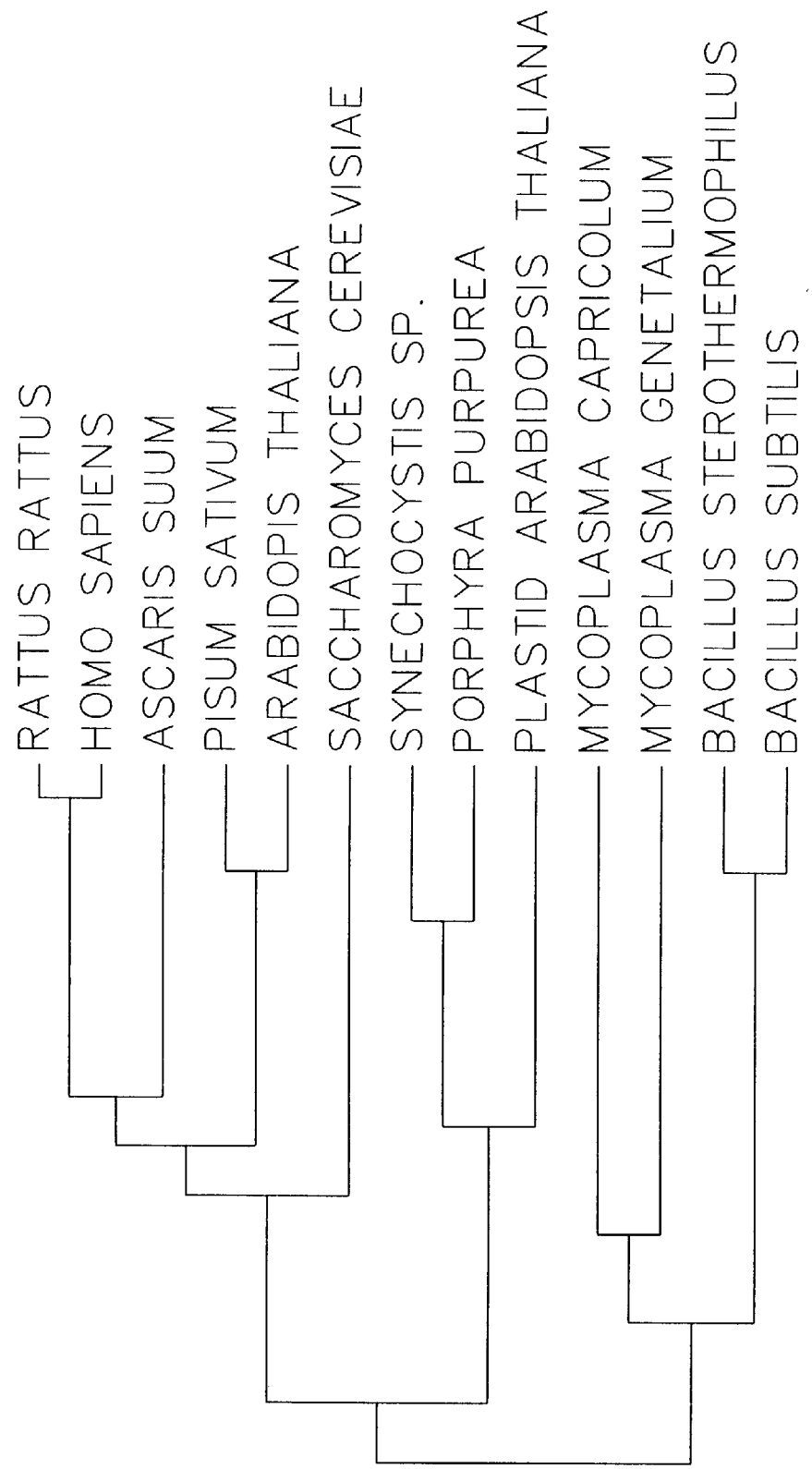
FIGS. 6A–6B show dendrogram analyses of the deduced amino acid sequence of PDH E1α and E1β subunits, respectively. Abbreviations and accession numbers to the sequences are: P. p., Porphyra purpurea odp (U38804); S. sp., Synechocystis sp. (D90915); A. t., Arabidopsis thaliana (U21214, U09137); P. s., Pisum sativum (U51918, U56697); H. s., Homo sapiens (L13318, D90086); R. r., Rattus rattus (Z12158, P49432); S. c., Saccharomyces cerevisiae (P16387, M98476); A. s., Ascaris suum (M76554, M38017); M. gen., Mycoplasma genetalium (U39706); M. c., Mycoplasma capricolum (U62057); B. su., Bacillus subtilis (M57435); and B. s., Bacillus stearothermophilus (X53560). Dendrogram analyses was accomplished with GeneWorks CLUSTAL V method (IntelliGenetics, Mountain View, Calif.). CLUSTAL V parameters were as follows: cost to open gap=5, cost to lengthen gap=25, gap penalty=3, number of top diagonals=5, window size=5, PAM matrix=PAM250, K-tuple=1, and consensus cutoff=50%.
Figure 6B:
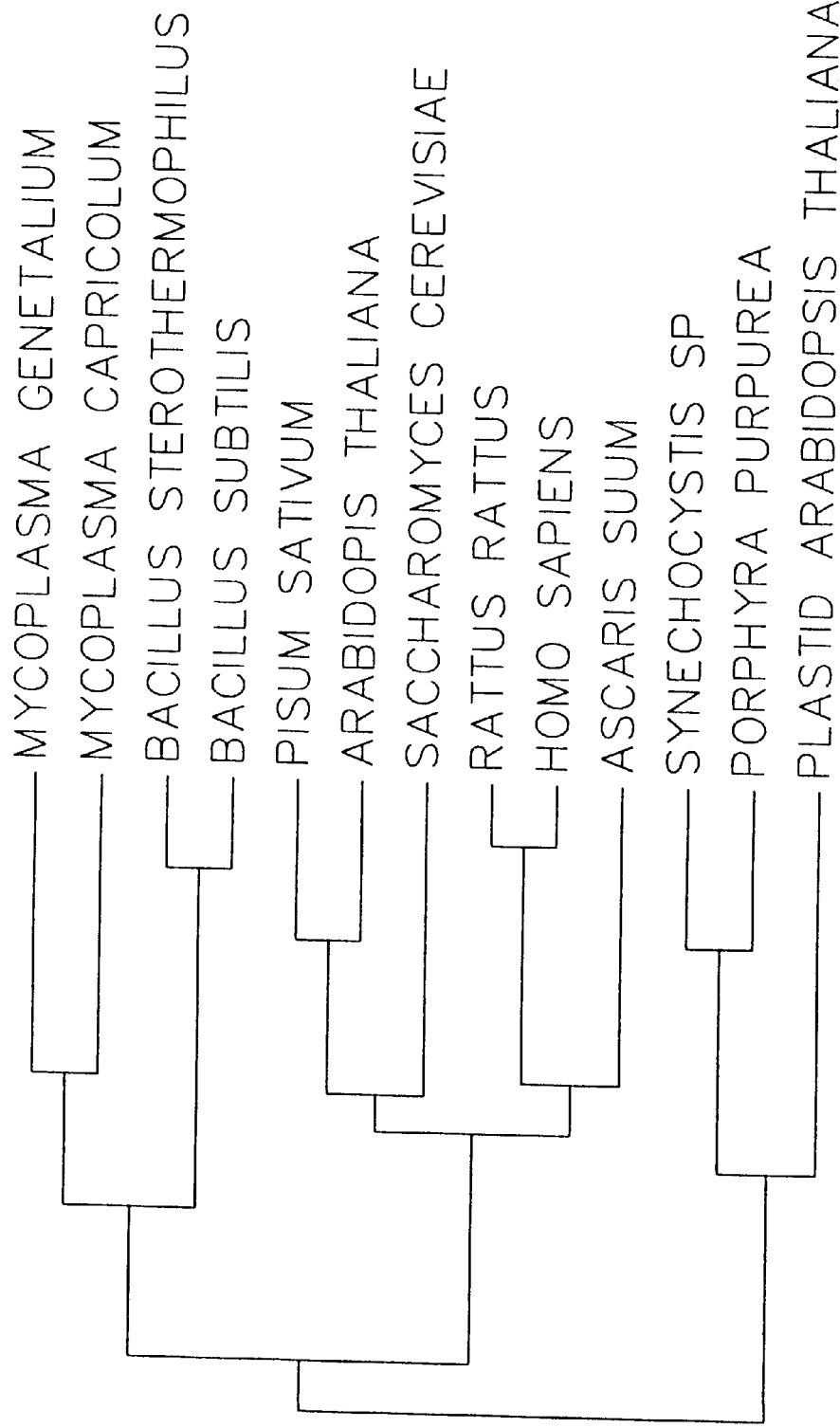

Dendrogram analyses show that *A. thaliana* plastid E1, *P. purpurea* chloroplast odp, and Synechocystis sp. (a cyanobacterium) pdh sequences segregate as a family distinct from mitochondrial and bacterial sequences (FIGS. 6A and 6B). A similar separation has also been shown for plastid and mitochondrial ribosomal RNA sequences (Palmer, 1992). The *A. thaliana* plastid cDNAs and *P. purpurea* odp genes are the only sequences reported thus far for plastid forms of PDH.

As additional cDNAs and genes for plastid and mitochondrial specific isozymes are determined, insight as to the lineage of plastid genes will be gained. Mitochondrial rRNA genes show convincing similarity to purple-photosynthetic bacterial rRNA sequences. In contrast, plastid rRNA has similarity with cyanobacterial rRNA. This relationship between plastids and cyanobacteria has also been noted for genes encoding the transcriptional and translational apparatus (Palmer, 1992). The new sequences reported here should contribute to understanding if the emergence of mitochondria and plastids was the result of single or multiple primary (i.e., eubacteria/eukaryotic) endosymbioses, or if secondary (i.e., eukaryotic/eukaryotic) endosymbioses led to the establishment of these organelles (Palmer, 1992).

Antibodies to the E1α subunit of the plastid pyruvate dehydrogenase complex were generated by inserting the gel purified BamHI to HindIII fragment of the cDNA for E1 at the BamHI (5') to HindIII (3') cloning site of pET28a (Novagen). The recombinant clone was expressed, and the 5' end sequenced to ensure the correct reading frame. The recombinant protein was expressed using the above construct in *E. coli* strain BL21 (DE3) (Novagen). Growth conditions were as follows: A single colony was picked and cultured in 5 mL LB+150 micrograms ampicillin overnight at 37 C shaking at 200 rpm. The 5 ml culture was used to inoculate 500 mL LB+150 microgram ampicillin and was allowed to grow for 4 h. The culture was then induced using 0.1 mM IPTG and allowed to shake at 37 C for an additional 5 h. The culture was then centrifuged in a GSA rotor at 7,000 rpm to pellet cells. Cells were lysed in 6 M guanidinium HCl, 10 mM Tris pH 8.0 at room temperature. Cell debris was pelleted at 12,000 rpm in an SS-34 rotor for 20 min, and the recombinant protein was purified using Ni-NTA agarose. Rabbits were injected with 150 microgram of recombinant protein mixed 1:1 with complete adjuvant. A 30 day boost was given with the same protein preparation, at the same concentration. Ten days after the boost, the antibody titer was determined to be 1:80,000 against pea chloroplast stromal extract by immunoblot procedures.

It should be noted that the present invention encompasses not only the specific DNA sequences disclosed herein and the polypeptides encoded thereby, but also biologically functional equivalent nucleotide and amino acid sequences. The phrase "biologically functional equivalent nucleotide sequences" denotes DNAs and RNAs, including chromosomal DNA, plasmid DNA, cDNA, synthetic DNA, and mRNA nucleotide sequences, that encode polypeptides exhibiting the same or similar enzymatic activity as that of the enzyme polypeptides encoded by the sequences disclosed herein when assayed by standard enzymatic methods, or by complementation. Such biologically functional equivalent nucleotide sequences can encode polypeptides that contain a region or moiety exhibiting sequence similarity to the corresponding region or moiety of the present disclosed polypeptides.

One can isolate polypeptides useful in the present invention from various organisms based on homology or sequence identity. Although particular embodiments of nucleotide sequences encoding the polypeptides disclosed herein are shown in the various SEQ IDs presented, it should be understood that other biologically functional equivalent forms of such polypeptide-encoding nucleic acids can be readily isolated using conventional DNA-DNA or DNA-RNA hybridization techniques. Thus, the present invention also includes nucleotide sequences that hybridize to any of the nucleic acid SEQ IDs and their complementary sequences presented herein, and that code on expression for polypeptides exhibiting the same or similar enzymatic activity as that of the presently disclosed polypeptides. Such nucleotide sequences preferably hybridize to the nucleic acid sequences presented herein or their complementary sequences under moderate to high stringency (see Sambrook et al., 1989). Exemplary conditions include initial hybridization in 6×SSC, 5×Denhardt's solution, 100 μg/ml fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5–1×SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The present invention also encompasses nucleotide sequences that hybridize under salt and temperature conditions equivalent to those described above to genomic DNA, plasmid DNA, cDNA, or synthetic DNA molecules that encode the same amino acid sequences as these nucleotide sequences, and genetically degenerate forms thereof due to the degeneracy of the genetic code, and that code on expression for a polypeptide that has the same or similar enzymatic activity as that of the polypeptides disclosed herein.

Biologically functional equivalent nucleotide sequences of the present invention also include nucleotide sequences that encode conservative amino acid changes within the amino acid sequences of the present polypeptides, producing silent changes therein. Such nucleotide sequences thus contain corresponding base substitutions based upon the genetic code compared to the nucleotide sequences encoding the present polypeptides. Substitutes for an amino acid within the fundamental polypeptide amino acid sequences discussed herein can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; and (4) neutral nonpolar (hydrophobic) amino acids such as alanine, leucine, isoleucine, valine, praline, phenylalanine, tryptophan, and methionine.

Conservative amino acid changes within the present polypeptide sequences can be made by substituting one amino acid within one of these groups with another amino acid within the same group. The encoding nucleotide sequences (gene, plasmid DNA, cDNA, synthetic DNA, or mRNA) will thus have corresponding base substitutions, permitting them to code on expression for the biologically functional equivalent forms of the present polypeptides.

Useful biologically functional equivalent forms of the DNA sequences disclosed herein include DNAs comprising nucleotide sequences that exhibit a level of sequence identity to corresponding regions or moieties of these DNA sequences from 40% sequence identity, or from 60% sequence identity, or from 80% sequence identity, to 100% sequence identity to the DNAs encoding the presently disclosed polypeptides. However, regardless of the percent sequence identity of these nucleotide sequences, the encoded proteins would possess the same or similar enzymatic activity as the present polypeptides. Thus, biologically functional equivalent nucleotide sequences encompassed by the present invention include sequences having less than 40% sequence identity to any of the nucleic acid sequences presented herein, so long as they encode polypeptides having the same or similar enzymatic activity as the polypeptides disclosed herein.

Sequence identity can be determined using the "BestFit" or "Gap" programs of the Sequence Analysis Software Package, Genetics Computer Group, Inc., University of Wisconsin Biotechnology Center, Madison, Wis. 53711.

Due to the degeneracy of the genetic code, i.e., the existence of more than one codon for most of the amino acids naturally occuring in proteins, genetically degenerate DNA (and RNA) sequences that contain the same essential genetic information as the DNA sequences disclosed herein, and which encode the same amino acid sequences as these DNA sequences, are encompassed by the present invention. Genetically degenerate forms of any of the other nucleic acid sequences discussed herein are encompassed by the present invention as well.

The alternative nucleotide sequences described above are considered to possess a biological function substantially equivalent to that of the polypeptide-encoding DNAs of the present invention if they encode polypeptides having enzymatic activity differing from that of any of the present polypeptides by about 30% or less, preferably by about 20% or less, and more preferably by about 10% or less when assayed in vivo by complementation or in vitro by the standard enzymatic assays.

EXAMPLE 2

Cloning and Sequencing of a cDNA Encoding the Arabidopsis thaliana Dihydrolipoamide S-acetyltransferase (E2) Component of the Plastid Pyruvate Dehydrogenase Complex A search of the Arabidopsis expressed sequence tagged (EST) database identified one Arabidopsis thaliana EST clone which has significant homology to the (cyanobacterial) Synechocystis sp. dihydrolipoamide acetyltransferase subunit, GenBank accession D90915. The Arabidopsis EST clone (GenBank accession W43179) was obtained from the Arabidopsis Biological Resource Center (ABRC) at Ohio State University, then used to screen an Arabidopsis λPRL2 cDNA library (ABRC) for a full length clone as in Example 1. Two (approximately 1700 bp) clones assessed as full length, were identified and sequenced as in Example 1.

The plastid PDC E2 clone is 1709 bp in length (SEQ ID NO:5; GenBank accession AF066079) with a continuous open reading frame of 1440 bp encoding a protein of 480 amino acids (SEQ ID NO:6), with a deduced molecular mass of 52,400 daltons. The mature portion of the E2 component, without the chloroplast targeting peptide (see below), has a deduced molecular mass of 44,900 daltons. When subjected to SDS-PAGE electrophoresis, the full length and the mature plastid PDC E2 proteins ran slower than a globular protein of the same mass. These proteins appeared on SDS-PAGE to have molecular masses of 69,000 and 62,000, respectively. This slow migration on SDS-PAGE electrophoresis is consistent with the electrophoretic behavior of mitochondrial E2 components (Guest et al., 1985).

The mature part of the cDNA clone (coding for the catalytic region of the protein) was expressed in E. coli using the pET28c expression vector (Novagen, Madison, Wis.).

The recombinant protein (which includes a C-terminal six histidine tag) was purified under denaturing conditions by Ni-NTA affinity chromatography according to the manufacturer's instructions (Qiagen Inc., Chatsworth, Calif.). Polyclonal antibodies were raised to the recombinant protein in New Zealand White rabbits. These antibodies recognize the recombinant protein at a high dilution (1:100,000). In a analysis of an extract of purified pea chloroplasts, these antibodies recognized two proteins. One protein electrophoretically migrated at an apparent mass of 62,000, identical to the electrophoretic behavior of the mature plastid PDC E2 component. The other protein which was recognized by the anti-E2 antibodies had an electrophoretic mobility with an apparent mass of 76,000 daltons. This larger protein is likely due to mitochondrial contamination, since its apparent mass is equivalent to the mitochondrial E2 component.

The cDNAs for the *Arabidopsis thaliana* plastid E1α, E1β, and E2 were transcribed and translated in vitro using the TnT™ transcription/translation system (Promega, Madison, Wis.) with the plasmid pZL1 (Life Technologies, Inc.) and the T7 promoter. Presenting the product to isolated pea chloroplasts resulted in ATP-dependent import into the plastid in a manner that protects it from protease action. This establishes that the cDNA sequences encode plastid targeting sequences. These targeting sequences are assessed to be the first 68 amino acids of the E1α subunit (FIG. 12 and SEQ ID NO:2), the first 73 amino acids of the E1β subunit (FIG. 14 and SEQ ID NO:4), and the first 54 amino acids of the E2 component (SEQ ID NO:6).

EXAMPLE 3

Cloning and Sequencing of cDNA Encoding the *Arabidopsis thaliana* E1α Subunit of the Branched-Chain Oxoacid Dehydrogenase Complex Selection of an *A. thaliana* expressed sequence tagged (EST) cDNA clone (Newman et al., 1994) was accomplished by searching the Arabidopsis EST database using the BLASTP program of the National Center for Biotechnology Information. One EST cDNA clone (GenBank accession N96041) was found to have significant homology to the tomato, human, and bovine BCOADC E1α subunits, making it a candidate for the *A. thaliana* E1α. This cDNA clone was obtained from the Arabidopsis Biological Resource Center at the Ohio State University. The clone was sequenced completely on both strands by subcloning restriction enzyme fragments of the clone and using two specific oligonucleotide primers designed from previously sequenced stretches. Sequencing was conducted by the DNA core facility at the University of Missouri, Columbia, Mo. on an ABI 377 instrument. The BCOADC E1α cDNA clone is 1587 bp, with a 3' untranslated region of 165 bp (FIG. 15 and SEQ ID NO:11). The open reading frame encodes a protein of 472 amino acids (FIG. 16 and SEQ ID NO:12) with a deduced molecular mass of 53,363 daltons. We have not identified an initiating methionine/start codon, but alignment with the tomato, bovine, human and mouse sequences shows the clone is considerably longer than the mature coding region of these proteins.

The deduced amino acid sequence of the clone has significant homology to BCOADC E1α sequences in the database: 56.8% identity with the tomato, 42% with the human, 40.7% with the bovine, and 41.6% with the mouse E1α amino acid sequences. Though an initiating methionine was not identified, the N-terminus has properties similar to a mitochondrial targeting peptide. The PSORT program (prediction of protein intracellular localization sites) suggests the mitochondrial matrix as the most probable destination of the *A. thaliana* E1α protein. However, the amino acid sequence also contains an SKL motif close to the C-terminus which is indicative of peroxisomal localization, and this is the second most probable localization site determined by the PSORT program.

$Ser_{366}$ of the *A. thaliana* amino acid sequence is at a position which is conserved in all the above sequences. This site is a designated phosphorylation site for the mouse and bovine sequences. However, the second conserved Ser phosphorylation site in the animal sequences is replaced by a Pro in the tomato sequence and an Ala in the *A. thaliana* sequence (FIG. 16 and SEQ ID NO:12).

EXAMPLE 4

Cloning and Sequencing of cDNA Encoding the *Arabidopsis thaliana* E1β Subunit of the Branched-Chain Oxoacid Dehydrogenase Complex Selection of *Arabidopsis thaliana* expressed sequence tagged (EST) clones (Newman et al., 1994) was accomplished by searching the Arabidopsis EST database using the BLASTP PROGRAM of the National Center for Biotechnology Information. Two EST clones were found to have significant homology to the human and bovine branched-chain oxoacid dehydrogenase (BCOADC) E1β subunit. These two clones (GenBank accessions T04217 and H37020) were identified as potentially encoding the *Arabidopsis thaliana* BCOADC E1β subunits. We obtained these partial EST clones from the Arabidopsis Biological Resource Center (ABRC) at Ohio State University. One of these clones, GenBank accession T04217, was used to screen an Arabidopsis cDNA library for full length clones. The EST cDNAs were gel purified from low-melting agarose and probes prepared by labeling with $[\alpha^{32}P]dATP$ using a random prime oligonucleotide labeling kit (Pharmacia, Piscataway, N.J.). Probes were desalted using Sephadex G-50 chromatography to remove unincorporated nucleotides. An Arabidopsis cDNA library (λ-PRL2, obtained from the ABRC) was plated at a density of $2.9 \times 10^4$ plaques per plate for a total of $2.03 \times 10^5$ plaques. Biotrace NT nylon filters (Gelman, Ann Arbor, Mich.) were used for plaque-lifts and were processed according to the manufacturer's specifications. Prehybridization and hybridizations were performed according to *Current Protocols in Molecular Biology*, (Ausubel, et al., 1994). After three successive rounds of screening, 5 independent potential E1β cDNA clones were isolated, ranging in size from 500 to 1400 bp. Two of the five cDNA clones were selected for sequencing. Plaque-purified λ phage were treated according to the manufacturer's instructions (GibcoBRL, Gaithersburg, Md.) in order to excise the pZL-1 recombinant clones. The cDNA sequences were obtained by sequencing both strands of the cDNA clone (and deletion fragments derived therefrom) using the Dye-deoxy terminating cycle sequencing reactions and an ABI prism Model 377 sequencer, according to the manufacuturer's instructions. Results from sequencing reactions were analyzed using IntelliGenetics GeneWorks DNA analysis program version 2.5 for Macintosh computers. Both cDNAs were identical. The BCOADC E1β cDNA is 1319 bp (FIG. 17 and SEQ ID NO:13) and contains a 133 bp 5' untranslated region, an open reading frame of 1056 bp followed by 130 bp 3' untranslated region. The open reading frame encodes a protein with 352 deduced amino acids (FIG. 18 and SEQ ID NO:14) with a calculated mass of 37,810 Daltons.

Table 4 shows the alignment of the deduced amino acid sequences of various BCOADC E1β subunits. "•" indicates conserved amino acids; "−" indicates a gap inserted to maximize homology. The deduced amino acid sequence is 59% identical to the mammalian BCOADC E1β subunit (Table 4). The primary sequence contains no obvious organellar targeting information.

The cDNA was expressed in *E. coli* after insertion into the plasmid vector pMal (New England Biolabs). The purified protein was used to prepare polyclonal antibodies which recognize the recombinant protein.

EXAMPLE 5

Cloning and Sequencing of cDNA Encoding the *Arabidopsis thaliana* Dihydrolipoamide S-acyltransferase (E2) Component of the Branched-Chain Oxoacid Dehydrogenase Complex A search of the Arabidopsis expressed sequence tagged (EST) database identified two *Arabidopsis thaliana* EST clones which have significant homology to the bovine and human branched-chain dihydrolipoamide acyltransferase subunit. These clones (GenBank accessions T42996 and N37840) were obtained from the Arabidopsis Biological Resource Center (ABRC) at Ohio State University. Sequencing of the 5' ends of the two clones showed only one to be a branched-chain E2 sequence (the other contained vector sequence only). The branched-chain EST clone (GenBank accession T42996) was sequenced completely on both strands by subcloning of restriction enzyme derived fragments and by primer walking. Sequencing reactions and analysis were performed as in Example 1.

The clone (SEQ ID NO:15) is 1618 bp in length and contains an open reading frame of 1449 bp encoding a protein of 483 amino acids (SEQ ID NO:16) with a predicted molecular mass of 52,729 daltons. Part of the cDNA clone (coding for the lipoyl and subunit-binding domains, and part of the catalytic domain) was expressed in *E. coli* using the pET28a expression vector (Novagen, Madison, Wis.). The recombinant protein (which includes a C-terminal six histidine tag) was purified under denaturing conditions by Ni-NTA affinity chromatography according to the manufacturer's instructions (Qiagen Inc., Chatsworth, Calif.). Polyclonal antibodies were raised to the recombinant protein in New Zealand White rabbits. These antibodies recognize the recombinant protein at a high dilution (>1:100,000).

EXAMPLE 6

Engineering Chimeric Branched Chain Oxoacid Dehydrogenase Complex E1α and E1β Subunits to Utilize the Plastid Pyruvate Dehydrogenase Complex E2 and E3 Components to Form a Hybrid Complex The cDNA (or other encoding DNA) of the BCOADC E1β subunit can be used to form a chimeric protein targeted to the plastid to utilize the plastid pyruvate dehydrogenase complex (PDC) E2 component to produce propionyl-CoA. The chimeric BCOADC E1β subunit can be modified to comprise the E2 binding region of the plastid PDC E1β subunit and a plastid targeting sequence. The thus modified BCOADC E1β subunit can then be imported into the chloroplast, where it binds to the plastid PDC E2 component and, in conjunction with the plastid PDC E3 component, catalyzes the production of propionyl-CoA from 2-oxybutyrate. This leads to the production of the PHA precursor 3-hydroxyvaleryl-CoA, and consequently to biosynthesis of the PHA co-polymer poly(3HB-co-3HV) in plants that have been engineered to contain other enzymes necessary for biosynthesis of this copolymer, as discussed above.

The nucleotide sequence that encodes the BCOADC E1β region 1 (the region or domain of the E1β protein that binds the BCOADC E1β component to the E2 core of the BCOADC complex [Wexler et al., 1991]) can be excised and replaced with the nucleotide sequence corresponding to the PDC E2 binding region from the plastid PDC E1β subunit (Johnston et al., 1997; Luethy et al., 1994). The construct can be further engineered to comprise a plastid targeting sequence of another plastid protein such as the Rubisco small subunit (Table 1) (von Heijne et al., 1991), or to comprise the plastid targeting sequence of the plastid PDC E1β subunit described by Johnston et al. (1997). See FIG. 7B.

Chimeric fusions of plastid targeting sequences and the BCOADC E1α and E1β subunits can be generated by amplifying fragments of DNA coding for the regions involved. Chloroplast targeting peptides from each of the plastid PDC E1 subunits (PDC E1α and E1β) (Johnston et al., 1997) can be amplified from the original cDNAs (SEQ ID NOs 1 and 3). Similarly, the mature portions of the BCOADC E1α and E1β subunits can be amplified from their cDNAs (SEQ ID NOs 11 and 13). A unique restriction site can be included in the primer design to permit ligation of the chloroplast targeting peptides in-frame with the mature portions of the BCOADC E1α and E1β subunits.

To produce a BCOADC E1β chimera that can associate with the PDC E2 subunit, one can modify the BCOADC E1β subunit to include the plastid PDC E1β targeting peptide along with the plastid PDC E1β E2 binding region. In the final construct, the sequence for the E2 binding region follows (i.e., is 3' to) the sequence for the targeting peptide, so that the chimeric BCOADC E1β protein contains approximately one-third plastid PDC E1β presequence (for example, amino acid residues 1 through 146 of SEQ ID NO:4) and the remainder consists of the BCOADC E1β subunit (for example, amino acid residues 94 through 352 of SEQ ID NO:14). The PDC E1β chloroplast targeting peptide and plastid PDC E2 binding region of the PDC E1β subunit can be amplified from the plastid PDC E1β cDNA (SEQ ID NO:4) using the following gene specific primer (SEQ ID NO:28) and a commercially available primer (e.g. M13/pUC forward primer, available from e.g. Stratagene, La Jolla, Calif.).

Forward oligonucleotide: 5' GGGCCC CATATG TCTTC-GATAATC 3' (SEQ ID NO:28). Nucleotides 7 through 21 are preceded by an Nde1 enzyme site.

The mature part of the BCOADC E1β sequence (excluding the native BCOADC E2 binding site) can be amplified from the cDNA of SEQ ID NO:13 using the following gene specific primers:

Forward oligonucleotide: 5' GGGCCC ACCGGT TTTG-GCATTGGTCTA 3' (SEQ ID NO:24). Nucleotides 406 through 423 are preceded by an Age1 enzyme site.

Reverse oligonucleotide: 5' GGGCCC GAATTC TCAT-TACTAGTAATTCAC AGT 3' (SEQ ID NO:25). Nucleotides 1177 through 1191 are preceded by an EcoR1 enzyme site.

Figure 7A:
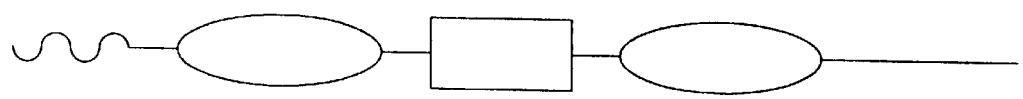
FIGS. 7A–7E show schematics (Constructs 1–5) for engineering the BCOADC subunits to be targeted to the plastid and to form a hybrid complex, as described in Examples 6 and 7.
Figure 7A:
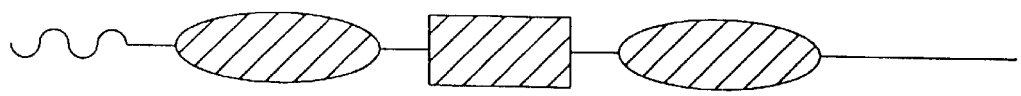
Figure 7A:
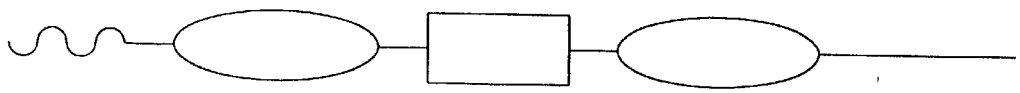
Figure 7B:
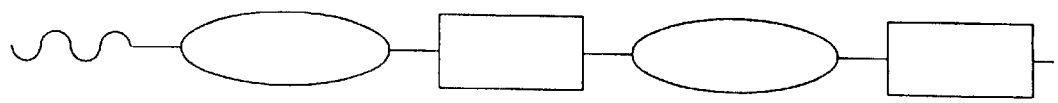
Figure 7B:
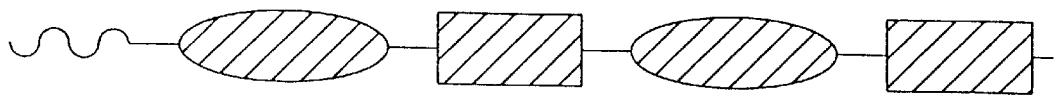
Figure 7B:
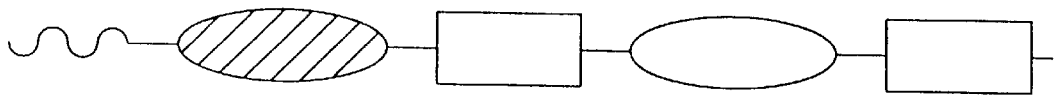

The resulting truncated BCOADC E1β sequence can be ligated to the plastid PDC E1β sequence using the Age1 enzyme site already present in the plastid PDC sequence at a convenient position (amino acid residue 146). The above primers can be utilized to produce DNA fragments useful in joining the noted regions of the plastid PDC and BCOADC E1β sequences without any introduced or substituted amino acids (FIG. 7B).

To produce a BCOADC E1α chimera that can be targeted to a plastid, a chloroplast targeting peptide, for example the chloroplast targeting peptide from the plastid PDC E1α subunit (Johnston et al., 1997) (corresponding to amino acid residues 1 through 68) can be attached 5' to the mature portion of the BCOADC E1α subunit. A DNA fragment corresponding to the plastid targeting peptide can be amplified from the original PDC E1α cDNA (SEQ ID NO:1) using the following gene specific primers (SEQ ID NO:29 and SEQ ID NO:30):

Forward primer: 5' GGGCCC CCATGG CGACG-GCTTTCGCT 3' (SEQ ID NO:29). Nucleotides 107 to 124 are preceded by an NcoI enzyme site.

Reverse primer: 5' GGGCCC TGATCA TATTATTG-GTGGATTGCTT 3' (SEQ ID NO:30). Nucleotides 311 to 328 are preceded by a BclI enzyme site.

The entire mature coding region of the BCOADC E1α subunit can then be excised from the cDNA (SEQ ID NO:11) using convenient restriction enzyme sites, BclI at nucleotides 195 through 200, and XbaI at nucleotides 1424 through 1429. This includes the 3' stop codon.

The restriction enzyme fragments generated from both the plastid PDC and BCOADC E1α sequences can then be ligated together and subcloned into an appropriate vector (e.g. pZL1, Life Technologies Inc., Gaithersberg, Md.). The BclI site used to ligate the two sequences introduces a single His residue between the plastid PDC E1β targeting peptide and the BCOADC E1α mature region.

The consequence of this addition can be determined experimentally to assess its impact, if any, on import and processing of the BCOADC E1α subunit, and on assembly of the hybrid BCOADC E1 complex.

An alternative approach to ligating the plastid PDC and BCOADC E1α sequences using the BclI site is to use a NotI site in its place in the design of the reverse oligonucleotide for the plastid targeting peptide, as follows (SEQ ID NO:19):

Plastid PDC E1α reverse primer: 5' GGGCCC GCGGC-CGC ATTATTGGTGGATTGCTT 3' (SEQ ID NO:19). Nucleotides 311 through 328 are preceded by a NotI enzyme site.

The coding region for the mature BCOADC E1α protein (FIG. 16 and SEQ ID NO:12) can then be amplified from the cDNA (SEQ ID NO:11) using the following gene-specific primers:

Forward primer: 5' GGGCCC GCGGCCGC TGAT-CATTTGGTTCAGCAG 3' (SEQ ID NO:20). Nucleotides 195 through 213 are preceded by a NotI enzyme site.

Reverse primer: 5' GGGCCC GTCGAC TCAAACAT-GAAAGCCAGG 3' (SEQ ID NO:21). Nucleotides 1405 through 1422 are preceded by a SalI enzyme site and includes the stop codon.

Ligation of the two resulting sequences using the NotI enzyme site will introduce three Ala residues between them, which would overcome the introduction of a charged residue (His) using the BclI site described above.

To confirm the ability of the chimeric BCOADC E1α and E1β proteins to be imported into chloroplasts, the DNA encoding these chimeric proteins can be subcloned into a transcription vector such as pZL1 (Life Technologies Inc., Gaithersberg, Md.) with the T7 promoter. The chimeric proteins are then transcribed/translated in vitro, for example using the TnT™ transcription/translation system (Life Technologies Inc.), and import assays with isolated chloroplasts can be performed. This is a reliable assay to test the import and assembly of the chimeric proteins.

Experimental results have established that in vitro imported plastid PDC E1α and E1β subunit proteins associate to form the plastid pyruvate dehydrogenase heterotetramer within the chloroplast matrix, and that this heterotetramer associates with imported PDC E2 subunits (Randall et al., unpublished).

To obtain constitutive expression of the chimeric proteins in plants, their coding regions are preferably fused to the CaMV 35S promoter sequence. For dicotyledonous plants, the use of the pZP200 binary vector, for Agrobacterium transformation, is preferred.

The chimeric nucleic acids disclosed above are used to transform *Arabidopsis thaliana* or other plants by various methods well known in the art. As one alternative, the BCOADC E1α-chimeric construct comprising the plastid PDC E1α targeting sequence is used to produce transformed plants that are then crossed with plants that have been transformed with the BCOADC E1β-chimeric construct containing the plastid PDC E1β subunit targeting sequence and E2 component binding region.

Figure 7C:
Figure 7C:
Figure 7C:
Figure 7D:
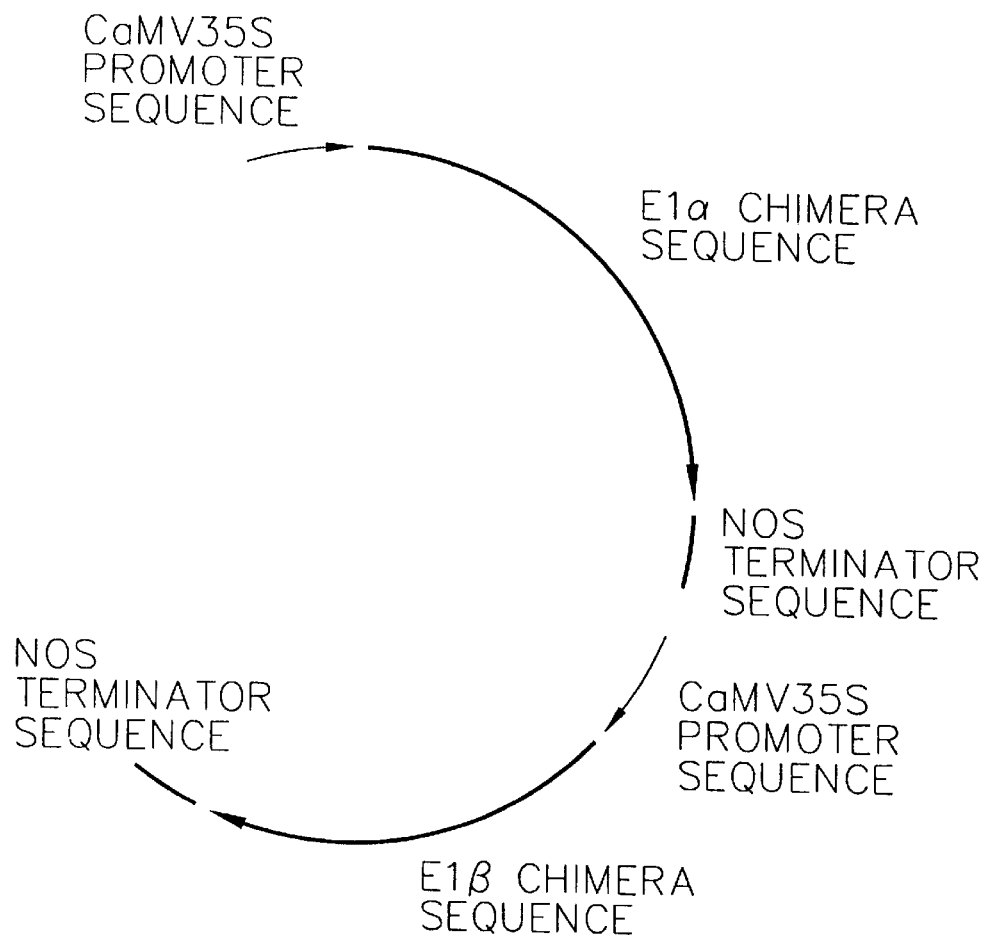

As another alternative, a compound construct containing both the plastid-targeted BCOADC E1α-chimera and the plastid-targeted BCOADC E1β-chimera containing the PDC E1β E2 binding region is constructed in the form of a mega plasmid and used to transform plants by standard protocols for expression of both subunit chimeras simultaneously (FIG. 7D). This can be achieved by including a stop signal at the 3' end of the BCOADC E1α chimeric sequence and a NOS transcription termination sequence. In order to obtain co-expression of the two chimeric sequences, a second CaMV 35S promoter sequence can be placed 3' to the transcription termination sequence of the plastid-targeted BCOADC E1α chimeric coding sequence. This second promoter sequence can in turn be followed by the sequence coding for the BCOADC E1β chimera. This creates a mega plasmid or compound construct coding for both the BCOADC E1α and β subunit chimeras (FIG. 7D).

The BCOADC E1α and β subunit chimeras thus targeted to the plastid bind to the plastid PDC E2 component (E2 components form the core of the complexes to which the E1 and E3 components bind). Since the chimeric BCOADC E1β subunit comprises the plastid PDC E1β E2 binding domain, a hybrid complex is formed. This hybrid complex is designed to have an enhanced ability to utilize 2-oxobutyrate as substrate in order to produce propionyl-CoA for 3-HV biosynthesis. Transgenic plants containing this hybrid complex can then be crossed by standard protocols with plants having enhanced ability to generate 2-oxobutyrate in the plastid compartment produced as described, for example, in Gruys et al. (1998).

EXAMPLE 7

Figure 7E:
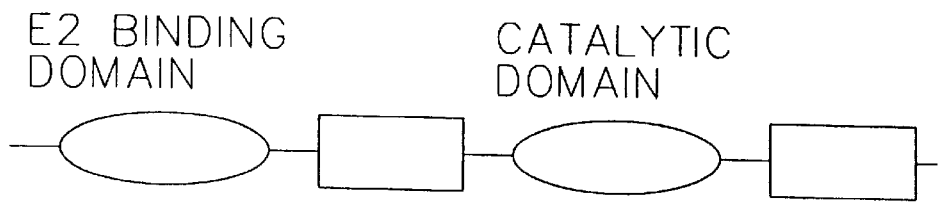
Figure 7E:
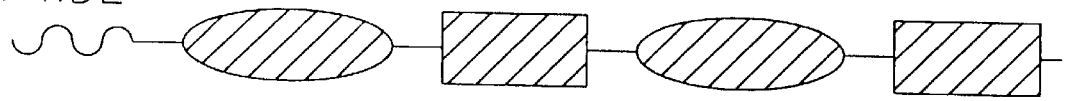
Figure 7E:
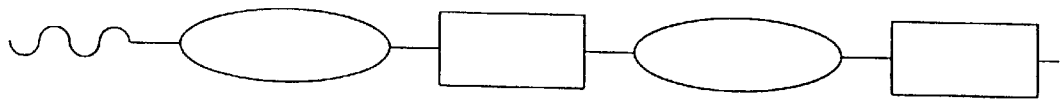

Targeting the BCOADC E1α, E1β, and E2 Components to the Plastid to Form a Hybrid Complex with the Plastid PDC E3 Component DNAs encoding the BCOADC E1α and β subunits and E2 component can be fused with plastid targeting sequences to direct importation of these proteins into the plastid to enhance propionyl-CoA production from 2-oxobutyrate. In this method, constructs of the BCOADC E1α and β subunits, the BCOADC E2 component, and, if desired, the BCOADC E3 subunit, can be made with plastid targeting sequences, for example with plastid targeting sequences of the plastid pyruvate dehydrogenase complex (PDC) E1α and β subunits (Johnston et al., 1997) or the plastid PDC E2 component. See FIGS. 7A, 7C, and 7E. These constructs can be used to transform plants individually (followed by genetic crossing to combine the necessary components from each plant) or together to direct the desired BCOADC components to the plastid. The BCOADC E1α-chimera is as described above in Example 6. The BCOADC E1β-chimera containing the PDC E1β E2 binding region is also described in Example 6. When the plastid-targeted BCOADC E2 chimera is also employed (see below), the E2 binding region of the BCOADC E1β subunit need not be replaced with the plastid PDC E1β subunit E2 binding region. Instead, only the plastid PDC E1β targeting peptide is attached to the mature portion of the BCOADC E1β subunit (still retaining the native binding site for the BCOADC E2 component) (FIG. 7E). This can be achieved by amplifying the appropriate regions of the PDC and BCOADC E1β cDNA sequences or other functionally equivalent DNA sequences. That portion of the cDNA coding for the plastid targeting peptide of the PDC E1β (amino acids 1 through 97) can be amplified from the cDNA (SEQ ID NO.:3) using the following gene specific primers. This amplified fragment includes a portion of the linker region between the targeting peptide and the E2-binding region.

Forward oligonucleotide: 5' GGGCCC CATATG TCTTC-GATAATC 3' (SEQ ID NO:22). Nucleotides 7 through 21 are preceded by an Nde1 enzyme site.

Reverse oligonucleotide: 5' GGGCCC CTCGAG ACCT-TCCTGAAGAGC 3' (SEQ ID NO:23). Nucleotides 277 through 297 are preceded by an Xho1 enzyme site.

The mature portion of the BCOADC E1β sequence (including the native BCOADC E2 binding region), i.e., amino acid residues 45 through 349, can be amplified from the cDNA of SEQ ID NO:13 using the following gene specific primers:

Forward oligonucleotide: 5' GGGCCC CTCGAG ATCGCTTTGGACACC 3' (SEQ ID NO:31). Nucleotides 262 through 277 are preceded by an Xho1 enzyme site.

Reverse oligonucleotide: 5' GGGCCC GAATTC TCAT-TACTAGTAATTCAC AGT 3' (SEQ ID NO:25). Nucleotides 1177 through 1191 are preceded by an EcoR1 enzyme site.

Use of the foregoing oligonucleotide primers allows the joining of the appropriate plastid PDC and BCOADC E1β sequences without any introduced or substituted amino acids (FIG. 7E). As disclosed in Example 6, the resulting DNA can be subcloned into a transcription vector to test import and assembly prior to transformation of Arabidopsis or other plants (or prior to the construction of a mega plasmid for co-expression, cf. FIG. 7D).

Further to the above, a chimera comprising the plastid targeting sequence (nucleotides 59–232) of the plastid PDC E2 (dihydrolipoamide acetyltransferase) component and the sequence for the mature BCOADC dihydrolipoamide acyltransferase (E2) subunit can be constructed. The N-terminus of the BCOADC E2 subunit can be replaced with the chloroplast targeting peptide from the plastid PDC E2 subunit. In this case, the native E2 binding domain of the BCOADC E1β subunit need not be replaced with the E2 binding domain of the plastid PDC E1β subunit as described in Example 6. Only the plastid PDC E2 targeting peptide is needed because the BCOADC E2 component which is imported into the plastid will naturally associate with the BCOADC E1β subunit.

The plastid targeting sequence can be amplified from the plastid PDC E2 cDNA of SEQ ID NO:5 using the following gene-specific primers:

Forward primer: 5' GGGCCC CATATG GCGGTTTCT-TCT 3' (SEQ ID NO:26). Nucleotides 59 through 73 are preceded by an Nde1 enzyme site.

Reverse primer; 5' GGGCCC CCATGGC AATTTCAG-GATTCTT 3' (SEQ ID NO:27). Nucleotides 218 through 232 are preceded by an Nco1 enzyme site.

The region coding for the mature portion of the BCOADC E2 protein can be excised from the cDNA (SEQ ID NO.:15) using convenient restriction enzymes (Nco1 and Not1). This DNA fragment is then ligated in-frame with the PDC E2 plastid targeting peptide using the common Nco1 enzyme site (FIG. 7C). As described in Example 6, the import and assembly of this chimeric E2 subunit can be examined by in vitro import assays. Efficient import of the BCOADC E2 protein into isolated pea chloroplasts and formation of a complex with both the endogenous PDC heterotetramer and imported BCOADC E1α-E1β heterotetramer can be determined.

The plastid-targeted branched-chain oxoacid dehydrogenase complex components utilize any 2-oxobutyrate (α-ketobutyrate) produced in the plastid to make propionyl CoA, which in turn is a substrate for the enzymes producing polyhydroxyalkanoic acids (PHAs).

As previously indicated, it appears to be unnecessary to prepare a plastid-targeted construct for the BCOADC E3 component since the E3 components of all of the mitochondrial α-ketoacid dehydrogenase complexes appear to be interchangeable. The PDC E3 component already present in the plastid should function with the plastid-targeted BCOADC E1α, E1β, and E2 subunits. If desired, one can, for example, place a plastid targeting sequence on the mitochondrial E3 component in place of the first 31 amino acids of the mitochondrial PDC E3 reported by Turner et al. (1992) (GenBank accession number X2995), corresponding to the first 72 nucleotides of that particular cDNA. This is done by standard protocols well known to those skilled in the art.

As discussed above, the plastid is capable of PHA biosynthesis when the appropriate enzymes are present in the plant (Poirier et al., 1992; Nawrath et al., 1994). Targeting BCOADC subunits and components to this organelle as described in Examples 6 and 7 herein further enhances ability of plants to biosynthesize the 3HB-co-3HV copolymer.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

References Cited

Ainley et al., (1990) Plant Mol. Biol. 14: 949.

Ali et al., (1993) J. Biol. Chem. 268: 22353.

Ausubel et al., (1989) *Current Protocols in Molecular Biology*, John Wiley & Sons, Inc.

Ausubel et al., (1994) *Current Protocols in Molecular Biology*, John Wiley & Sons, Inc.

Back et al., (1991) Plant Mol. Biol. 17: 9.

Becker et al., (1994) Plant J. 5: 299.

Behal et al., (1989) Biochem. Biophys. Res. Commun. 164: 941.

Bower and Birch, (1992) Plant J. 2: 409.
Brandl et al., (1990) Adv. Biochem. Eng. Biotech. 41: 77.
Budde et al., (1991) Plant Physiol. 95: 131.
Bustos et al., (1991) EMBO J. 10: 1469.
Byrom, (1987) Trends Biotechnol. 5: 246.
Bytebier et al., (1987) Proc. Natl. Acad. Sci. USA 84: 5345.
Camp and Randall, (1985) Plant Physiol. 77: 571.
Camp et al., (1988) Biochim. Biophys. Acta 933: 269.
Cassas et al., (1993) Proc. Natl. Acad. Sci. USA 90: 11212.
Castresana et al., (1988) EMBO J. 7: 1929.
Christou (March/April, 1994) Agro Food Industry Hi Tech, p.17.
Christou et al., (1991) Bio/Technology 9: 957.
Dawes and Senior, (1973) Adv. Microb. Physiol. 14: 135.
De la Pena et al., (1987) Nature 325: 274.
Doi, (1990) *Bacterial Polyesters*, VCH Publishers, Inc., New York.
Doyle et al., (1986) J. Biol. Chem. 261: 9228.
Eswaran et al., (1995) Biochim. Biophys. Acta 1252: 203.
Feinbaum et al., (1991) Mol. Gen. Genet. 226: 449.
Fisk and Dandekar, (1993) Scientia Horticulturae 55: 5.
Fosket, (1994) *Plant Growth and Development*, Academic Press, Inc., San Diego, p. 132.
Fromm et al., (1990) Bio/Technology 8: 833.
Gasser and Fraley, (1989) Science 244: 1293.
Gavel and von Heijne, (1990) FEBS 261: 455.
Gerbling and Gerhardt, (1988) Plant Physiol. 88: 13.
Gerbling and Gerhardt, (1989) Plant Physiol. 91: 1387.
Gopalakrishnan et al., (1989) Biochem. Biophys. Res. Commun. 160: 715.
Gordon-Kamm et al., (1990) Plant Cell 2: 603.
Grof et al., (1995) Plant Physiol. 108: 1623.
Gruys et al., (1998) PCT International Publication WO 98/00557.
Guan et al., (1995) J. Biol. Chem. 270: 5412.
Guest et al., (1985) J. Molec. Biol. 185:743.
Hoffman, U.S. Pat. No. 5,106,739.
Horn et al., (1988) Plant Cell Rep. 7: 469.
Johnson et al., (1992) Molec. Biochem. Parasitol. 51: 37.
Johnston et al., (1997) Biochim. Biophys. Acta. 1321: 200.
Jones and Yeaman, (1986) Biochem. J. 237: 621.
Kang and Rawsthorne, (1994) Plant J. 6: 795.
Kaneko et al., (1996) DNA Research 3: 109.
Karchi et al., (1993) Plant J. 3: 721.
Kares et al., (1990) Plant Mol. Biol. 15: 905.
Knutzon et al., (1992) Proc. Natl. Acad. Sci USA 89: 2624.
Korotchkina and Patel, (1995) J. Biol. Chem. 270: 14397.
Koziel et al., (1993) Bio/Technology 11: 194.
Kridl et al., (1991) Seed Sci. Res. 1: 209.
Kuhlemeier et al., (1989) Plant Cell 1: 471.
Layman, (Oct. 31, 1994) Chem. & Eng. News, p. 10.
Lam and Chua, (1990) Science 248: 471.
Lemoigne, (1926) Bull. Soc. Chim. Biol. (Paris) 8: 770.
Lindsay, (1992) Modern Plastics 2: 62.
Luethy et al., (1994) Biochim. Biophys. Acta 1187: 95.
Luethy et al., (1995) Gene 164: 251.
Luethy et al., (1995) J. Plant Physiol. 145: 443.
Maliga et al., U.S. Pat. No. 5,451,513.
Maliga et al., PCT International Publication WO 95/16783.
Maliga et al., PCT International Publication WO 95/24492.
Maliga et al., PCT International Publication WO 95/24493.
Miernyk and Dennis, (1983) J. Exp. Bot. 34: 712.
Minsky et al., (1997) Abst. 5th Int. Cong. Plant Molec. Biol., Abstract No. 302.
Nakamura et al., (1992) Int. J. Biol. Macromol. 14: 321.
Nawrath et al., (1994) Proc. Natl. Acad. Sci USA 91: 12760.
Newman et al., (1994) Plant Physiol. 106: 1241.
Odell et al., (1985) Nature 313: 810.
Ohlrogge et al., (1979) Proc. Natl. Acad. Sci. USA 76: 1194.
Ou-Lee et al., (1986) Proc. Natl. Acad. Sci USA 83: 6815.
Padgette et al., (1995) Crop Sci. 35: 1451.
Palmer, (1992) in *Plant Gene Research: Cell Organelles* (Herrmann, R. G., ed.), Vol. 7, pp. 99–133, Springer-Verlag/Wien, Wurzburg.
Patel, M. S. and Roche, T. E. (1990) FASEB J. 4: 3224.
Paxton et al., (1986) Biochem. J. 234: 295.
Peoples and Sinskey, (1989a) J. Biol. Chem. 264: 15293.
Peoples and Sinskey, (1989b) J. Biol. Chem. 264: 15298.
Pettit et al., (1978) Proc. Natl. Acad. Sci. USA 75: 1881.
Poirier et al., (1992) Science 256: 520.
Poirier et al., (1995) Bio/Technology 13: 142.
Potrykus, (1991) Annu. Rev. Plant Physiol. Plant Mol. Biol. 42: 205.
Randall et al., (1977) Arch. Biochem. Biophys. 178: 342.
Randall et al., (1989) Ann. N.Y. Acad. Sci. 573: 192.
Randall et al., (1996) Proc. Phytochem. Soc. Europe 39: 87.
Reed, L. J. (1974) Acc. Chem. Res. 7: 40.
Reid et al., (1975) Biochem. Biophys. Res. Commun. 62: 42.
Reid et al., (1977) Plant Physiol. 59: 842.
Reith and Munholland, (1995) Plant Molec. Biol. Rep. 13: 333.
Rhodes et al., (1988) Science 240: 204.
Richins et al., (1987) NAR 20: 8451.
Sambrook et al., (1989) *Molecular Cloning: A Laboratory Manual*, Second Edition, Cold Spring Harbor Laboratory Press, Cold Spring Harbor, N.Y.
Schubert et al., (1988) J. Bacteriol. 170: 5837.
Schulze-Lefert et al., (1989) EMBO J. 8: 651.
Slater et al., (1988). J. Bacteriol. 170: 4431.
Slighton and Beachy, (1987) Planta 172: 356.
Smith et al., (1992) Plant Physiol. 98: 1233.
Somers et al., (1992) Bio/Technology 10: 1589.
Staub and Maliga, (1993) EMBO J. 12: 601.
Stayton et al., (1991) Aust. J. Plant. Physiol. 18: 507.
Steinbüchel, (1991) In: *Biomaterials*, D. Byrom (Ed.), MacMillan, Basingstoke, pp. 123–213.

Steinbüchel and Pieper, (1992) Appl. Microbiol. Biotechnol. 37: 1.
Svab et al., (1990) Proc. Natl. Acad. Sci. USA 87: 8526.
Svab and Maliga, (1993) Proc. Natl. Acad. Sci. USA 90: 913.
Taylor et al., (1992) Planta 188: 255.
Thompson et al., (1977a) Plant Physiol. 59: 849.
Thompson et al., (1977b) Plant Physiol. 59: 854.
Toriyama et al., (1988) Bio/Technology 6: 10.
Turner et al., (1992) J. Biol. Chem. 267: 7745.
Vasil et al., (1992) Bio/Technology 10: 667.
Von Heijne et al., (1989) Eur. J. Biochem. 180: 535.
Von Heijne et al., (1991) Plant Mol. Biol. Rep. 9: 104.
Wan and Lemaux, (1994) Plant Physiol. 104: 37.
Wang et al., (1992) Bio/Technology 10: 691.
Weeks et al., (1993) Plant Physiol. 102: 1077.
Weisshaar et al., (1991) EMBO J. 10: 1777.
Wexler et al., (1991) FEBS Lett. 282: 209.
Williams et al., (1979) Plant Physiol. 64: 1099.
Wynn et al., (1996) In: *Alpha-Keto Acid Dehydrogenase Complexes*. M. S. Patel, T. E. Roche and R. A. Harris (eds). Birkhäuser Verlag, Basel, Switzerland. pp. 101–117.
Yamaguchi-Shinozaki et al., (1990) Plant Mol. Biol. 15: 905.
Yeaman, (1989) Biochem. J. 257: 625.
Yoon et al., (1995) J. Ferment. Bioeng. 80: 350.
Zhang and Wu, (1988) Theor. Appl. Genet. 76: 835.
Zhong et al., (1993) Plant Cell Rep. 13: 1.
Zilkey and Canvin, (1969) Biochem. Biophys. Res. Commun. 34: 646.

What is claimed is:

1. An isolated DNA molecule, comprising a nuclcotide sequence selected from the group consisting of:
   (a) the nuclcotide sequence shown in SEQ ID NO:1, or the complement thereof;
   (b) a nucleotide sequence that hybridizes to said nuccotide sequence of (a) under a wash stringency equivalent to 0.1×SSC, 0.1% SDS, at 55° C., and which encodes a polypeptide having enzymatic activity differing from that of *Arabidopsis thaliana* plastid pyruvate dehydrogenase complex E1α subunit by about 30% or less;
   (c) a nucleotide sequence encoding the same amino acid sequence as said nucleotide sequence of (a), but which is degenerate in accordance with the degeneracy of the genetic code; and
   (d) a nucleotide sequence encoding the same amino acid sequence as said nucleotide sequence of (b), but which is degenerate in accordance with the degeneracy of the genetic code.

2. A recombinant vector, comprising said isolated DNA molecule of claim 1.

3. A host cell transformed with said recombinant vector of claim 2.

4. An isolated DNA molecule, comprising a nucleotide sequence selected from the group consisting of:
   (a) the nucleotide sequence shown in SEQ ID NO:3, or the complement thereof;
   (b) a nucleotide sequence that hybridizes to said nucleotide sequence of (a) under a wash stringency equivalent to 0.1×SSC, 0.1% SDS, at 55° C., and which encodes a polypeptide having enzymatic activity differing from that of *Arabidopsis thaliana* plastid pyruvate dehydrogenase complex E1β submit by about 30% or less;
   (c) a nucleotide sequence encoding the same amino acid sequence as said nucleotide sequence of (a), but which is degenerate in accordance with the degeneracy of the genetic code; and
   (d) a nucleotide sequence encoding the same amino acid sequence as said nucleotide sequence of (b), but which is degenerate in accordance with the degeneracy of the genetic code.

5. A recombinant vector, comprising said isolated DNA molecule of claim 4.

6. A host cell transformed with said recombinant vector of claim 5.

7. An isolated DNA molecule, comprising a nucleotide sequence selected from the group consisting of:
   (a) the nucleotide sequence shown in SEQ ID NO:5, or the complement thereof;
   (b) a nucleotide sequence that hybridizes to said nucleotide sequence of (a) under a wash stringency equivalent to 0.1×SSC, 0.1% SDS, at 55° C., and which encodes a polypeptidc having enzymatic activity differing from of *Arabidopsis thaliana* plastid pyruvate dehydrogenase complex E2 component by about 30% or less;
   (c) a nucleotide sequence encoding the same amino acid sequence as said nucleotide sequence of (a), but which is degenerate in accordance with the degeneracy of the genetic code; and
   (d) a nucleotide sequence encoding the same amino acid sequence as said nucleotide sequence of (b), but which is degenerate in accordance with the degeneracy of the genetic code.

8. A recombinant vector, comprising said isolated DNA molecule of claim 7.

9. A host cell transformed with said recombinant vector of claim 8.

10. An isolated DNA molecule, comprising a nucleotide sequence selected from the group consisting of:
    (a) the nucleotide sequence shown in SEQ ID NO:11, or the complement thereof;
    (b) a nucleotide sequence that hybridizes to said nucleotide sequence of (a) under a wash stringency equivalent to 0.1×SSC, 0.1% SDS, at 55° C., and which encodes a polypeptide having enzymatic activity differing from that of *Arabidopsis thaliana* branched chain 2-oxoacid dehydrogenase complex E1α subunit by about 30% or less;

(c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code.

11. A recombinant vector, comprising said isolated DNA molecule of claim 10.

12. A host cell transformed with said recombinant vector of claim 11.

13. An isolated DNA molecule, comprising a nucleotide sequence selected from the group consisting of:

(a) the nucleotide sequence shown in SEQ ID NO:13, or the complement thereof;

(b) a nucleotide sequence that hybridizes to said nucleotide sequence of (a) under a wash stringency equivalent to 0.1×SSC, 0.1% SDS, at 55° C., and which encodes a polypeptide having enzymatic activity differing from that of *Arabidopsis thaliana* branched chain 2-oxoacid dehydrogenase complex E1β subunit by about 30% or less;

(c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code.

14. A recombinant vector, comprising said isolated DNA molecule of claim 13.

15. A host cell transformed with said recombinant vector of claim 14.

16. An isolated DNA molecule, comprising a nucleotide sequence selected from the group consisting of:

(a) the nucleotide sequence shown in SEQ ID NO:15, or the complement thereof;

(b) a nucleotide sequence that hybridizes to said nucleotide sequence of (a) under a wash stringency equivalent to 0.1×SSC, 0.1% SDS, at 55° C., and which encodes a polypeptide having enzymatic activity differing from that of *Arabidopsis thaliana* branched chain 2-oxoacid dehydrogenase complex E2 component by about 30% or less;

(c) a nuclcotide sequence encoding the same amino acid sequence as said nuclcotide sequence of (a), but which is degenerate in accordance with the degeneracy of the genetic code; and (d) a nuelcotide sequence encoding the same amino acid sequence as said nucleotide sequence of (b), but which is degenerate in accordance with the degeneracy of the genetic code.

17. A recombinant vector, comprising said isolated DNA molecule of claim 16.

18. A host cell transformed with said recombinant vector of claim 17.

* * * * *

UNITED STATES PATENT AND TRADEMARK OFFICE
CERTIFICATE OF CORRECTION

PATENT NO. : 6,143,561
DATED : November 7, 2000
INVENTOR(S) : Douglas D. Randall et al.

It is certified that error appears in the above-identified patent and that said Letters Patent is hereby corrected as shown below:

Column 1,
Line 11, add -- This invention was made with U.S. Government support under National Science Foundation Grant No. IBN 9419489. The U.S. Government has certain rights in the invention. --

Signed and Sealed this

Twenty-sixth Day of July, 2005

JON W. DUDAS
*Director of the United States Patent and Trademark Office*

SEQUENCE LISTING

<160> NUMBER OF SEQ ID NOS: 54

<210> SEQ ID NO 1
<211> LENGTH: 1541
<212> TYPE: DNA
<213> ORGANISM: Arabidopsis thaliana

<400> SEQUENCE: 1

```
ccacgcgtcc gcatctcttg ttctctccgc ccatctctgc tctcttttat tttcccagaa      60
agttttttt  tttttttccg aattccgtta atctcattgg ggtttccatt gatagcaatg     120
gcgacggctt tcgctcccac taagctcact gccacggttc ctctgcatgg atcccatgag     180
aatcgtctct tgctcccgat ccgattggct cctccttctt ctttcctcgg atccacccgt     240
tccctctccc ttcgcagact caatcactcc aacgccaccc gtcgatctcc cgtcgtctct     300
gtccaggaag ttgtcaagga gaagcaatcc accaataata ccagcctgtt gataaccaaa     360
gaggaaggat tggagttgta tgaagatatg atactaggta gatctttcga agacatgtgt     420
gctcaaatgt attaccgagg caagatgttt ggttttgttc acttgtacaa tggccaagag     480
gctgtttcta ctggctttat caagctcctt accaagtctg actctgtcgt tagtacctac     540
cgtgaccatg tccatgccct cagcaaaggt gtctctgctc gtgctgttat gagcgagctc     600
ttcggcaagg ttactggatg ctgcagaggc caagtggat ccatgcacat gttctccaaa      660
gaacacaaca tgcttggtgg ctttgctttt attggtgaag gcattcctgt cgccactggt     720
gctgcctta gctccaagta caggagggaa gtcttgaaac aggattgtga tgatgtcact      780
gtcgccttt tcggagatgg aacttgtaac aacggacagt tcttcgagtg tctcaacatg     840
gctgctctct ataaactgcc tattatcttt gttgtcgaga taacttgtg ggccattggg      900
atgtctcact tgagagccac ttctgacccc gagatttgga agaaaggtcc tgcatttggg     960
atgcctggtg ttcatgttga cggtatggat gtcttgaagg tcagggaagt cgctaaagaa    1020
gctgtcacta gagctagaag aggagaaggt ccaaccttgg ttgaatgtga gacttataga    1080
ttcagaggac actccttggc tgatcccgat gagctccgtg atgctgctga gaaagccaaa    1140
tacgcggcta gagacccaat cgcagcattg aagaagtatt tgatagagaa caagcttgca    1200
aaggaagcag agctaaagtc aatagagaaa aagatagacg agttggtgga ggaagcggtt    1260
gagtttgcag acgctagtcc acagcccggt cgcagtcagt tgctagagaa tgtgtttgct    1320
```

-continued

```
gatccaaaag gatttggaat tggacctgat ggacggtaca gatgtgagga ccccaagttt    1380
accgaaggca cagctcaagt ctgagaagac aagtttaacc ataagctgtc tactgtctct    1440
tcgatgtttc tatatatctt attaagttaa atgctacaga gaatcagttt gaatcatttg    1500
cactttttgc ttaaaaaaaa aaaaaaaaaa aaaaaaaaa a                         1541
```

<210> SEQ ID NO 2
<211> LENGTH: 428
<212> TYPE: PRT
<213> ORGANISM: Arabidopsis thaliana

<400> SEQUENCE: 2

```
Met Ala Thr Ala Phe Ala Pro Thr Lys Leu Thr Ala Thr Val Pro Leu
 1               5                  10                  15

His Gly Ser His Glu Asn Arg Leu Leu Leu Pro Ile Arg Leu Ala Pro
             20                  25                  30

Pro Ser Ser Phe Leu Gly Ser Thr Arg Ser Leu Ser Leu Arg Arg Leu
         35                  40                  45

Asn His Ser Asn Ala Thr Arg Arg Ser Pro Val Val Ser Val Gln Glu
     50                  55                  60

Val Val Lys Glu Lys Gln Ser Thr Asn Asn Thr Ser Leu Leu Ile Thr
 65                  70                  75                  80

Lys Glu Glu Gly Leu Glu Leu Tyr Glu Asp Met Ile Leu Gly Arg Ser
                 85                  90                  95

Phe Glu Asp Met Cys Ala Gln Met Tyr Tyr Arg Gly Lys Met Phe Gly
            100                 105                 110

Phe Val His Leu Tyr Asn Gly Gln Glu Ala Val Ser Thr Gly Phe Ile
        115                 120                 125

Lys Leu Leu Thr Lys Ser Asp Ser Val Val Ser Thr Tyr Arg Asp His
    130                 135                 140

Val His Ala Leu Ser Lys Gly Val Ser Ala Arg Ala Val Met Ser Glu
145                 150                 155                 160

Leu Phe Gly Lys Val Thr Gly Cys Cys Arg Gly Gln Gly Gly Ser Met
                165                 170                 175

His Met Phe Ser Lys Glu His Asn Met Leu Gly Gly Phe Ala Phe Ile
            180                 185                 190

Gly Glu Gly Ile Pro Val Ala Thr Gly Ala Ala Phe Ser Ser Lys Tyr
        195                 200                 205

Arg Arg Glu Val Leu Lys Gln Asp Cys Asp Val Thr Val Ala Phe
    210                 215                 220

Phe Gly Asp Gly Thr Cys Asn Asn Gly Gln Phe Phe Glu Cys Leu Asn
225                 230                 235                 240

Met Ala Ala Leu Tyr Lys Leu Pro Ile Ile Phe Val Val Glu Asn Asn
                245                 250                 255

Leu Trp Ala Ile Gly Met Ser His Leu Arg Ala Thr Ser Asp Pro Glu
            260                 265                 270

Ile Trp Lys Lys Gly Pro Ala Phe Gly Met Pro Gly Val His Val Asp
        275                 280                 285

Gly Met Asp Val Leu Lys Val Arg Glu Val Ala Lys Glu Ala Val Thr
    290                 295                 300

Arg Ala Arg Arg Gly Glu Gly Pro Thr Leu Val Glu Cys Glu Thr Tyr
305                 310                 315                 320

Arg Phe Arg Gly His Ser Leu Ala Asp Pro Asp Glu Leu Arg Asp Ala
                325                 330                 335
```

```
Ala Glu Lys Ala Lys Tyr Ala Ala Arg Asp Pro Ile Ala Ala Leu Lys
        340                 345                 350

Lys Tyr Leu Ile Glu Asn Lys Leu Ala Lys Glu Ala Glu Leu Lys Ser
        355                 360                 365

Ile Glu Lys Lys Ile Asp Glu Leu Val Glu Glu Ala Val Glu Phe Ala
        370                 375                 380

Asp Ala Ser Pro Gln Pro Gly Arg Ser Gln Leu Leu Glu Asn Val Phe
385                 390                 395                 400

Ala Asp Pro Lys Gly Phe Gly Ile Gly Pro Asp Gly Arg Tyr Arg Cys
                405                 410                 415

Glu Asp Pro Lys Phe Thr Glu Gly Thr Ala Gln Val
        420                 425

<210> SEQ ID NO 3
<211> LENGTH: 1441
<212> TYPE: DNA
<213> ORGANISM: Arabidopsis thaliana

<400> SEQUENCE: 3
gaaaaaatgt cttcgataat ccatggagct ggagctgcta cgacgacgtt atcgacgttt     60
aattccgtcg attccaagaa actcttcgtt gctccttctc gcacaaatct ttcagtgagg    120
agccagagat atatagtggc tggatctgat gcgagtaaga gagctttgg ttctggactt     180 agagttcgtc actctcagaa attgattcca aatgctgttg cgacgaagga ggcggatacg    240
tctgcgagca ctggacatga actattgctt ttcgaggctc ttcaggaagg tctggaagaa    300
gagatggaca gagatccaca tgtatgtgtt atgggtgaag atgttggcca ttacggaggt    360
tcctacaagg taaccaaagg ccttgctgat aaatttggtg acctcagggt ctcgacact     420 cctatttgtg aaaatgcatt caccggtatg gcattggag ctgccatgac tggtctaaga     480
cccgttattg aaggtatgaa catgggtttc ctcctcctcg ccttcaacca aatctccaac    540
aactgtggaa tgcttcacta cacatccggt ggtcagttta cgatcccggt tgtcatccgt    600
ggacctggtg gagtgggacg ccagcttggt gctgagcatt cacagaggtt agaatcttac    660
tttcagtcca tccctgggat ccagatggtt gcttgctcaa ctccttacaa cgccaaaggg    720
ttgatgaaag ccgcaataag aagcgagaac cctgtgattc tgttcgaaca cgtgctgctt    780
tacaatctca aggagaaaat cccggatgaa gattacatct gtaaccttga gaagctgag     840 atggtcagac ctggcgagca cattaccatc ctcacttact cgcgaatgag gtaccatgtg    900
atgcaggcag caaaaactct ggtgaacaaa gggtatgacc ccgaggttat cgacatcagg    960
tcactgaaac cgttcgacct tcacacaatt ggaaactcgg tgaagaaaac acatcgggtt   1020
ttgatcgtgg aggagtgtat gagaaccggt gggattgggg caagtcttac agctgccatc   1080
aacgagaact tcatgactta cttagatgct ccggtgatgt gttatcttc tcaagacgtt    1140 cctacacctt acgctggtac actggaggag tggaccgtgg ttcaaccggc tcagatcgtg   1200
accgctgtcg agcagctttg ccagtaaatt catatttatc cgatgaacca ttatttatca   1260
tttacctctc catttccttt ctctgtagct tagttcttaa agaatttgtc taagatggtt   1320
tgtttttgtt aaagtttgtc tcctttgttg tgtcttttaa tatggtttgt aactcagaat   1380
gtttgtttgt taatttttatc tcccactttc ttttaaaaaa aaaaaaaaaa aaaaaaaaaa   1440
a                                                                   1441

<210> SEQ ID NO 4
<211> LENGTH: 406
```

<212> TYPE: PRT
<213> ORGANISM: Arabidopsis thaliana

<400> SEQUENCE: 4

Met Ser Ser Ile Ile His Gly Ala Gly Ala Thr Thr Thr Leu Ser
1               5                   10                  15

Thr Phe Asn Ser Val Asp Ser Lys Lys Leu Phe Val Ala Pro Ser Arg
            20                  25                  30

Thr Asn Leu Ser Val Arg Ser Gln Arg Tyr Ile Val Ala Gly Ser Asp
        35                  40                  45

Ala Ser Lys Lys Ser Phe Gly Ser Gly Leu Arg Val Arg His Ser Gln
    50                  55                  60

Lys Leu Ile Pro Asn Ala Val Ala Thr Lys Glu Ala Asp Thr Ser Ala
65                  70                  75                  80

Ser Thr Gly His Glu Leu Leu Leu Phe Glu Ala Leu Gln Glu Gly Leu
                85                  90                  95

Glu Glu Glu Met Asp Arg Asp Pro His Val Cys Val Met Gly Glu Asp
            100                 105                 110

Val Gly His Tyr Gly Gly Ser Tyr Lys Val Thr Lys Gly Leu Ala Asp
        115                 120                 125

Lys Phe Gly Asp Leu Arg Val Leu Asp Thr Pro Ile Cys Glu Asn Ala
    130                 135                 140

Phe Thr Gly Met Gly Ile Gly Ala Ala Met Thr Gly Leu Arg Pro Val
145                 150                 155                 160

Ile Glu Gly Met Asn Met Gly Phe Leu Leu Leu Ala Phe Asn Gln Ile
                165                 170                 175

Ser Asn Asn Cys Gly Met Leu His Tyr Thr Ser Gly Gly Gln Phe Thr
            180                 185                 190

Ile Pro Val Val Ile Arg Gly Pro Gly Gly Val Gly Arg Gln Leu Gly
        195                 200                 205

Ala Glu His Ser Gln Arg Leu Glu Ser Tyr Phe Gln Ser Ile Pro Gly
    210                 215                 220

Ile Gln Met Val Ala Cys Ser Thr Pro Tyr Asn Ala Lys Gly Leu Met
225                 230                 235                 240

Lys Ala Ala Ile Arg Ser Glu Asn Pro Val Ile Leu Phe Glu His Val
                245                 250                 255

Leu Leu Tyr Asn Leu Lys Glu Lys Ile Pro Asp Glu Asp Tyr Ile Cys
            260                 265                 270

Asn Leu Glu Glu Ala Glu Met Val Arg Pro Gly Glu His Ile Thr Ile
        275                 280                 285

Leu Thr Tyr Ser Arg Met Arg Tyr His Val Met Gln Ala Ala Lys Thr
    290                 295                 300

Leu Val Asn Lys Gly Tyr Asp Pro Glu Val Ile Asp Ile Arg Ser Leu
305                 310                 315                 320

Lys Pro Phe Asp Leu His Thr Ile Gly Asn Ser Val Lys Lys Thr His
                325                 330                 335

Arg Val Leu Ile Val Glu Glu Cys Met Arg Thr Gly Gly Ile Gly Ala
            340                 345                 350

Ser Leu Thr Ala Ala Ile Asn Glu Asn Phe His Asp Tyr Leu Asp Ala
        355                 360                 365

Pro Val Met Cys Leu Ser Ser Gln Asp Val Pro Thr Pro Tyr Ala Gly
    370                 375                 380

Thr Leu Glu Glu Trp Thr Val Val Gln Pro Ala Gln Ile Val Thr Ala
385                 390                 395                 400

-continued

Val Glu Gln Leu Cys Gln
                405

<210> SEQ ID NO 5
<211> LENGTH: 1708
<212> TYPE: DNA
<213> ORGANISM: Arabidopsis thaliana

<400> SEQUENCE: 5

```
cgtccacttc actctctcta aactctctct cagatctctc tctctctgtg attcaacaat      60
ggcggtttct tcttcttcgt ttctatcgac agcttcacta accaattcca aatccaacat     120
ttcattcgct tcctcagtat ccccatccct ccgcagcgtc gttttccgct ccacgactcc     180
ggcgacttct caccgtcgtt caatgacggt ccgatctaag attcgtgaaa ttttcatgcc     240
ggcgttatca tcaaccatga cggaaggcaa atcgtgtca tggatcaaaa cagaaggcga     300
gaaactcgcc aagggagaga gtgttgtggt tgttgaatct gataaagccg atatggatgt     360
agaaacgttt tacgatggtt atcttgctgc gattgtcgtc ggagaaggtg aaacagctcc     420
ggttggtgct gcgattggat tgttagctga gactgaagct gagatcgaag aagctaagag     480
taaagccgct tcgaaatctt cttcttctgt ggctgaggct gtcgttccat ctcctcctcc     540
ggttacttct tctcctgctc cggcgattgc tcaaccggct ccggtgacgg cagtatcaga     600
tggtccgagg aagactgttg cgacgccgta tgctaagaag cttgctaaac aacacaaggt     660
tgatattgaa tccgttgctg aactggacc attcggtagg attacggctt ctgatgtgga     720
gacggcggct ggaattgctc cgtccaaatc ctccatcgca ccaccgcctc ctcctccacc     780
tccggtgacg gctaaagcaa ccaccactaa tttgcctcct ctgttacctg attcaagcat     840
tgttcctttc acagcaatgc aatctgcagt atctaagaac atgattgaga gtctctctgt     900
tcctacattc cgtgttggtt atcctgtgaa cactgacgct cttgatgcac tttacgagaa     960
ggtgaagcca aagggtgtaa caatgacagc tttattagct aaagctgcag ggatggcctt    1020
ggctcagcat cctgtggtga acgctagctg caaagacggg aagagtttta gttacaatag    1080
tagcattaac attgcagtgg cggttgctat caatggtggc ctgattacgc ctgttctaca    1140
agatgcagat aagttggatt tgtacttgtt atctcaaaaa tggaaagagc tggtggggaa    1200
agctagaagc aagcaacttc aaccccatga atacaactct ggaacttta ctttatcgaa    1260
tctcggtatg tttggagtgg atagatttga cgctattctt ccgccaggac agggtgctat    1320
tatggctgtt ggagcgtcaa agccaactgt agttgctgat aaggatggat tcttcagtgt    1380
aaaaaacaca atgctggtga atgtgactgc agatcatcgc attgtgtatg agctgactt    1440
ggctgctttt ctccaaacct ttgcaaagat cattgagaat ccagatagtt tgaccttata    1500
agacgccaag cgaagacgag aagtcaaaaa cagtttccaa aattcctgag ccaaatttt    1560
cccaagtaaa tttttaacc tcaatgttct tgggcttgcc caacttcttt tgcatctttt    1620
cctcacttgg gttgtaccgg tatttggttt caagaatcac cattttgggg ttttaacaaa    1680
taatttccaa ccaaaaaaaa aaaaaaaa                                      1708
```

<210> SEQ ID NO 6
<211> LENGTH: 480
<212> TYPE: PRT
<213> ORGANISM: Arabidopsis thaliana

<400> SEQUENCE: 6

Met Ala Val Ser Ser Ser Ser Phe Leu Ser Thr Ala Ser Leu Thr Asn

-continued

```
  1               5                  10                 15
Ser Lys Ser Asn Ile Ser Phe Ala Ser Ser Val Ser Pro Ser Leu Arg
                20                  25                 30

Ser Val Val Phe Arg Ser Thr Thr Pro Ala Thr Ser His Arg Arg Ser
            35                  40              45

Met Thr Val Arg Ser Lys Ile Arg Glu Ile Phe Met Pro Ala Leu Ser
        50                  55                  60

Ser Thr Met Thr Glu Gly Lys Ile Val Ser Trp Ile Lys Thr Glu Gly
 65                  70                  75                  80

Glu Lys Leu Ala Lys Gly Ser Val Val Val Glu Ser Asp Lys
                 85                  90                  95

Ala Asp Met Asp Val Glu Thr Phe Tyr Asp Gly Tyr Leu Ala Ile
             100                 105                 110

Val Val Gly Glu Gly Glu Thr Ala Pro Val Gly Ala Ala Ile Gly Leu
             115                 120                 125

Leu Ala Glu Thr Glu Ala Glu Ile Glu Glu Ala Lys Ser Lys Ala Ala
 130                 135                 140

Ser Lys Ser Ser Ser Val Ala Glu Ala Val Val Pro Ser Pro Pro
 145             150                 155                 160

Pro Val Thr Ser Ser Pro Ala Pro Ala Ile Ala Gln Pro Ala Pro Val
             165                 170                 175

Thr Ala Val Ser Asp Gly Pro Arg Lys Thr Val Ala Thr Pro Tyr Ala
             180                 185                 190

Lys Lys Leu Ala Lys Gln His Lys Val Asp Ile Glu Ser Val Ala Gly
             195                 200                 205

Thr Gly Pro Phe Gly Arg Ile Thr Ala Ser Asp Val Glu Thr Ala Ala
 210                 215                 220

Gly Ile Ala Pro Ser Lys Ser Ser Ile Ala Pro Pro Pro Pro Pro
 225             230                 235                 240

Pro Pro Val Thr Ala Lys Ala Thr Thr Thr Asn Leu Pro Pro Leu Leu
             245                 250                 255

Pro Asp Ser Ser Ile Val Pro Phe Thr Ala Met Gln Ser Ala Val Ser
             260                 265                 270

Lys Asn Met Ile Glu Ser Leu Ser Val Pro Thr Phe Arg Val Gly Tyr
             275                 280                 285

Pro Val Asn Thr Asp Ala Leu Asp Ala Leu Tyr Glu Lys Val Lys Pro
 290                 295                 300

Lys Gly Val Thr Met Thr Ala Leu Leu Ala Lys Ala Ala Gly Met Ala
 305                 310                 315                 320

Leu Ala Gln His Pro Val Val Asn Ala Ser Cys Lys Asp Gly Lys Ser
             325                 330                 335

Phe Ser Tyr Asn Ser Ser Ile Asn Ile Ala Val Ala Val Ala Ile Asn
             340                 345                 350

Gly Gly Leu Ile Thr Pro Val Leu Gln Asp Ala Asp Lys Leu Asp Leu
             355                 360                 365

Tyr Leu Leu Ser Gln Lys Trp Lys Glu Leu Val Gly Lys Ala Arg Ser
 370                 375                 380

Lys Gln Leu Gln Pro His Glu Tyr Asn Ser Gly Thr Phe Thr Leu Ser
 385                 390                 395                 400

Asn Leu Gly Met Phe Gly Val Asp Arg Phe Asp Ala Ile Leu Pro Pro
                 405                 410                 415

Gly Gln Gly Ala Ile Met Ala Val Gly Ala Ser Lys Pro Thr Val Val
                 420                 425                 430
```

```
Ala Asp Lys Asp Gly Phe Phe Ser Val Lys Asn Thr Met Leu Val Asn
        435                 440                 445

Val Thr Ala Asp His Arg Ile Val Tyr Gly Ala Asp Leu Ala Ala Phe
    450                 455                 460

Leu Gln Thr Phe Ala Lys Ile Ile Glu Asn Pro Asp Ser Leu Thr Leu
465                 470                 475                 480

<210> SEQ ID NO 7
<211> LENGTH: 25
<212> TYPE: DNA
<213> ORGANISM: Arabidopsis thaliana

<400> SEQUENCE: 7
cggtaccaag tctgactctg tcgtt                                              25

<210> SEQ ID NO 8
<211> LENGTH: 26
<212> TYPE: DNA
<213> ORGANISM: Arabidopsis thaliana

<400> SEQUENCE: 8
ccttcgaagg ttccatctcc gaaaaa                                             26

<210> SEQ ID NO 9
<211> LENGTH: 25
<212> TYPE: DNA
<213> ORGANISM: Arabidopsis thaliana

<400> SEQUENCE: 9
cggtaccttc gaggctcttc aggaa                                              25

<210> SEQ ID NO 10
<211> LENGTH: 24
<212> TYPE: DNA
<213> ORGANISM: Arabidopsis thaliana

<400> SEQUENCE: 10
ccttcgaacg ggccttagac cagt                                               24

<210> SEQ ID NO 11
<211> LENGTH: 1587
<212> TYPE: DNA
<213> ORGANISM: Arabidopsis thaliana

<400> SEQUENCE: 11
gggcgatctg gtttgctaga tccaaaaccc ttgtttctag cttgagacat aatctaaatt        60
tgtcgacaat tctcataaaa cgtgattact ctcatcgtcc catcttctat acaacttctc       120
agttatcttc aacggcgtat ttgagtccct tcggtagcct ccgtcatgag tctacggccg       180
tggagacaca ggctgatcat ttggttcagc agattgatga agtcgatgcc caggaactgg       240
atttcccagg aggcaaagtc ggttacacat cggagatgaa attcataccg gaatcatctt       300
caaggaggat tccatgttac cgggttcttg acgaagacgg acgaatcatc cccgatagcg       360
attttattcc ggtgagtgag aaactcgctg ttagaatgta cgaacaaatg gcgacgctac       420
aagtaatgga tcacatcttc tacgaagctc aacgtcaagg aagaatatct ttttatctta       480
cttccgtcgg agaagaagcc attaacatcg cttcagcagc tgctctcagt cctgacgacg       540
tcgttttacc tcagtaccga gaacctggag ttcttttgtg gcgtggcttc acgttggagg       600
agtttgctaa tcagtgtttt gggaacaaag ctgattatgg caaaggcaga caaatgccaa       660
```

-continued

```
ttcattacgg ttccaatcgt cttaattact tcactatctc ctctccaatt gccacgcaac    720
ttcctcaagc tgctggagtt ggttattctt tgaaaatgga caagaagaat gcttgtactg    780
ttacattcat cggagatggt ggcacaagcg agggagattt tcacgccgga ttgaattttg    840
cggccgtaat ggaagctccg gttgtgttta tatgtcggaa caacggttgg gcgattagta    900
ctcatatctc agaacagttt agaagtgatg gaatagttgt gaaggtcaa gcttacggta     960 tcccgaagca tcccgtgtgg gacggtaccg atgcacttgc ggtttatagt gctgtacgct   1020
cagctcgaga aatggctgta acagaacaaa gacctgttct cattgagatg atgacatata   1080
gagtaggaca tcattctaca tcagatgatt caactaagta cagggcggcg gatgaaatcc   1140
agtactggaa aatgtcgaga aaccctgtga atagatttcg gaaatgggtc gaagataacg   1200
gatggtggag tgaggaagat gaatccaagc taagatctaa cgcaagaaaa cagcttctgc   1260
aagcgattca ggctgcggag aagtgggaga acaaccatt gacagagttg tttaacgatg    1320
tatatgatgt taaaccgaag aacctagaag agcaagaact tggtttgaag gaattagtaa   1380
agaaacaacc tcaagattat cctcctggct ttcatgtttg aatctagagg aactgtgtgg   1440
ttaaaatacc tcgcggaccg cgaattcgat atcaagcttc tcattgcaga ctatttatat   1500
tgtccacgta tcgaatagta atcaagtatc aatgtagaga ccagcatttg gagcatcaaa   1560
aaaaaaaaaa aaaaaaaaa aaaaaaa                                         1587
```

<210> SEQ ID NO 12
<211> LENGTH: 472
<212> TYPE: PRT
<213> ORGANISM: Arabidopsis thaliana

<400> SEQUENCE: 12

```
Ala Ile Trp Phe Ala Arg Ser Lys Thr Leu Val Ser Ser Leu Arg His
 1               5                  10                  15

Asn Leu Asn Leu Ser Thr Ile Leu Ile Lys Arg Asp Tyr Ser His Arg
             20                  25                  30

Pro Ile Phe Tyr Thr Thr Ser Gln Leu Ser Ser Thr Ala Tyr Leu Ser
         35                  40                  45

Pro Phe Gly Ser Leu Arg His Glu Ser Thr Ala Val Glu Thr Gln Ala
     50                  55                  60

Asp His Leu Val Gln Gln Ile Asp Glu Val Asp Ala Gln Glu Leu Asp
 65                  70                  75                  80

Phe Pro Gly Gly Lys Val Gly Tyr Thr Ser Glu Met Lys Phe Ile Pro
                 85                  90                  95

Glu Ser Ser Arg Arg Ile Pro Cys Tyr Arg Val Leu Asp Glu Asp
            100                 105                 110

Gly Arg Ile Ile Pro Asp Ser Asp Phe Ile Pro Val Ser Glu Lys Leu
        115                 120                 125

Ala Val Arg Met Tyr Glu Gln Met Ala Thr Leu Gln Val Met Asp His
    130                 135                 140

Ile Phe Tyr Glu Ala Gln Arg Gln Gly Arg Ile Ser Phe Tyr Leu Thr
145                 150                 155                 160

Ser Val Gly Glu Glu Ala Ile Asn Ile Ala Ser Ala Ala Ala Leu Ser
                165                 170                 175

Pro Asp Asp Val Val Leu Pro Gln Tyr Arg Glu Pro Gly Val Leu Leu
            180                 185                 190

Trp Arg Gly Phe Thr Leu Glu Glu Phe Ala Asn Gln Cys Phe Gly Asn
        195                 200                 205
```

```
Lys Ala Asp Tyr Gly Lys Gly Arg Gln Met Pro Ile His Tyr Gly Ser
    210                 215                 220
Asn Arg Leu Asn Tyr Phe Thr Ile Ser Ser Pro Ile Ala Thr Gln Leu
225                 230                 235                 240
Pro Gln Ala Ala Gly Val Gly Tyr Ser Leu Lys Met Asp Lys Lys Asn
                245                 250                 255
Ala Cys Thr Val Thr Phe Ile Gly Asp Gly Gly Thr Ser Glu Gly Asp
                260                 265                 270
Phe His Ala Gly Leu Asn Phe Ala Ala Val Met Glu Ala Pro Val Val
            275                 280                 285
Phe Ile Cys Arg Asn Asn Gly Trp Ala Ile Ser Thr His Ile Ser Glu
        290                 295                 300
Gln Phe Arg Ser Asp Gly Ile Val Val Lys Gly Gln Ala Tyr Gly Ile
305                 310                 315                 320
Pro Lys His Pro Val Trp Asp Gly Thr Asp Ala Leu Ala Val Tyr Ser
                325                 330                 335
Ala Val Arg Ser Ala Arg Glu Met Ala Val Thr Glu Gln Arg Pro Val
                340                 345                 350
Leu Ile Glu Met Met Thr Tyr Arg Val Gly His His Ser Thr Ser Asp
            355                 360                 365
Asp Ser Thr Lys Tyr Arg Ala Ala Asp Glu Ile Gln Tyr Trp Lys Met
        370                 375                 380
Ser Arg Asn Pro Val Asn Arg Phe Arg Lys Trp Val Glu Asp Asn Gly
385                 390                 395                 400
Trp Trp Ser Glu Glu Asp Glu Ser Lys Leu Arg Ser Asn Ala Arg Lys
                405                 410                 415
Gln Leu Leu Gln Ala Ile Gln Ala Ala Glu Lys Trp Glu Lys Gln Pro
                420                 425                 430
Leu Thr Glu Leu Phe Asn Asp Val Tyr Asp Val Lys Pro Lys Asn Leu
            435                 440                 445
Glu Glu Gln Glu Leu Gly Leu Lys Glu Leu Val Lys Lys Gln Pro Gln
        450                 455                 460
Asp Tyr Pro Pro Gly Phe His Val
465                 470

<210> SEQ ID NO 13
<211> LENGTH: 1319
<212> TYPE: DNA
<213> ORGANISM: Arabidopsis thaliana

<400> SEQUENCE: 13
ttcttcaccc accaaaagta gcaaaccttt gccacctaaa aatcttacca gttgggtgaa      60
agttgccaaa atagagcttg cttttgtcgc aatcctatat ttttcagatt gattgttggt     120
gggtttgtgt aaatggcggc tcttttaggc agatcctgcc ggaaactgag ttttccgagc     180
ttgactcacg gagctaggag ggtatcgacg gaaactggaa aaccattgaa tctatactct     240
gctattaatc aagcgcttca catcgctttg gacaccgatc ctcggtctta tgtctttggg     300
gaagacgttg gctttggtgg agtctttcgc tgtacaactg gtttagctga acgattcggg     360
aaaaaccgtg tcttcaatac tcctcttgtt gagcaggca ttgttggatt tggcattggt     420
ctagcagcaa tgggtaatcg agcaattgta gagattcagt ttgcagatta tatatatcct     480
gcttttgatc agattgttaa tgaagctgca aagttcagat accgaagtgg taaccaattc     540
aactgtggag gacttacgat aagagcacca tatggagcag ttggtcatgg tggacattac     600
```

-continued

```
cattcacaat cccctgaagc tttcttttgc catgtccctg gtattaaggt tgttatccct    660
cggagtccac gagaagcaaa gggactgttg ttgtcatgta tccgtgatcc aaatcccgtt    720
gttttcttcg aaccaaagtg gctgtatcgt caagcagtag aagaagtccc tgagcatgac    780
tatatgatac ctttatcaga agcagaggtt ataagagaag gcaatgacat tacactggtt    840
ggatggggag ctcagcttac cgttatggaa caagcttgtc tggacgcgga aaaggaagga    900
atatcatgtg aactgataga tctcaagaca ctgcttcctt gggacaaaga accgttgag     960 gcttcagtta aaaagactgg cagacttctt ataagccatg aagctcctgt aacaggaggt    1020
tttggagcag agatctctgc aacaattctg gaacgttgct ttttgaagtt agaagctcca    1080
gtaagcagag tttgtggtct ggatactcca tttcctcttg tgtttgaacc attctacatg    1140
cccaccaaga acaagatatt ggatgcaatc aaatcgactg tgaattacta gccgtactat    1200
ctgtagttta ctgtttacac taggactaat gtaatcgcat gtctttgtta tcaattcgtc    1260
taatgtaaca ctaccgatta actttaatga atttcaagat aacgaaaaaa aaaaaaaaa    1319
```

<210> SEQ ID NO 14
<211> LENGTH: 352
<212> TYPE: PRT
<213> ORGANISM: Arabidopsis thaliana

<400> SEQUENCE: 14

```
Met Ala Ala Leu Leu Gly Arg Ser Cys Arg Lys Leu Ser Phe Pro Ser
  1               5                  10                  15

Leu Thr His Gly Ala Arg Arg Val Ser Thr Glu Thr Gly Lys Pro Leu
                 20                  25                  30

Asn Leu Tyr Ser Ala Ile Asn Gln Ala Leu His Ile Ala Leu Asp Thr
             35                  40                  45

Asp Pro Arg Ser Tyr Val Phe Gly Glu Asp Val Gly Phe Gly Gly Val
         50                  55                  60

Phe Arg Cys Thr Thr Gly Leu Ala Glu Arg Phe Gly Lys Asn Arg Val
 65                  70                  75                  80

Phe Asn Thr Pro Leu Cys Glu Gln Gly Ile Val Gly Phe Gly Ile Gly
                 85                  90                  95

Leu Ala Ala Met Gly Asn Arg Ala Ile Val Glu Ile Gln Phe Ala Asp
            100                 105                 110

Tyr Ile Tyr Pro Ala Phe Asp Gln Ile Val Asn Glu Ala Ala Lys Phe
        115                 120                 125

Arg Tyr Arg Ser Gly Asn Gln Phe Asn Cys Gly Gly Leu Thr Ile Arg
    130                 135                 140

Ala Pro Tyr Gly Ala Val Gly His Gly Gly His Tyr His Ser Gln Ser
145                 150                 155                 160

Pro Glu Ala Phe Phe Cys His Val Pro Gly Ile Lys Val Val Ile Pro
                165                 170                 175

Arg Ser Pro Arg Glu Ala Lys Gly Leu Leu Leu Ser Cys Ile Arg Asp
            180                 185                 190

Pro Asn Pro Val Val Phe Phe Glu Pro Lys Trp Leu Tyr Arg Gln Ala
        195                 200                 205

Val Glu Glu Val Pro Glu His Asp Tyr Met Ile Pro Leu Ser Glu Ala
    210                 215                 220

Glu Val Ile Arg Glu Gly Asn Asp Ile Thr Leu Val Gly Trp Gly Ala
225                 230                 235                 240

Gln Leu Thr Val Met Glu Gln Ala Cys Leu Asp Ala Glu Lys Glu Gly
```

|     |     |     |     |     |     |     |     |     |     |     |     |
| --- | --- | --- | --- | --- | --- | --- | --- | --- | --- | --- | --- |
|     |     |     | 245 |     |     |     | 250 |     |     |     | 255 |

Ile Ser Cys Glu Leu Ile Asp Leu Lys Thr Leu Leu Pro Trp Asp Lys
           260                    265               270

Glu Thr Val Glu Ala Ser Val Lys Lys Thr Gly Arg Leu Leu Ile Ser
    275                    280                    285

His Glu Ala Pro Val Thr Gly Gly Phe Gly Ala Glu Ile Ser Ala Thr
          290                    295                    300

Ile Leu Glu Arg Cys Phe Leu Lys Leu Glu Ala Pro Val Ser Arg Val
305                    310                    315                    320

Cys Gly Leu Asp Thr Pro Phe Pro Leu Val Phe Glu Pro Phe Tyr Met
               325                    330                    335

Pro Thr Lys Asn Lys Ile Leu Asp Ala Ile Lys Ser Thr Val Asn Tyr
          340                    345                    350

<210> SEQ ID NO 15
<211> LENGTH: 1450
<212> TYPE: DNA
<213> ORGANISM: Arabidopsis thaliana

<400> SEQUENCE: 15

| | |
|---|---|
| agaaacaaac acacggacca accgttcata acaatgatcg cgcgacggat ctggcgaagc | 60 |
| caccggtttc tccgcccatt cagctcgtca tctgtttgct ctccgccgtt ccgggtaccg | 120 |
| gagtatcttt ctcagtcgtc ttcctctccg gcgtcgcgcc cattctttgt tcaccctccc | 180 |
| actttgatga aatggggtgg aggaagtaga agctggtttt cgaacgaagc catggccact | 240 |
| gattcaaatt cagggttaat tgatgtgcca ctagctcaaa ctggggaagg tattgctgaa | 300 |
| tgtgagcttc tcaagtggtt tgtcaaagag ggagattctg tggaagagtt tcagccactc | 360 |
| tgtgaagttc agagcgataa agcaactata gagatcacaa gtcgttttaa agggaaagtg | 420 |
| gctctgattt cacattctcc aggtgacatt attaaggttg gagagactct ggttaggttg | 480 |
| gcggttgaag actcgcagga ttcgcttcta accactgata gttcagaaat tgtaactctg | 540 |
| ggaggttcaa gcagggaac agaaaatctt cttggagctc tctcaacgcc tgcggttcgt | 600 |
| aaccttgcaa aagaccttgg catagatatc aatgttataa ctggaactgg taaagatggt | 660 |
| agagttttga aagaggatgt tctccggttt agtgaccaga aaggatttgt aacagattca | 720 |
| gtttcttctg agcatgctgt tataggagga gactcggttt ccactaaagc tagtagtaac | 780 |
| tttgaagata aaacagttcc tctaagggga ttcagccgag caatggtcaa gacaatgact | 840 |
| atggctacaa gtgtaccgca ttttcatttt gttgaagaga taaactgcga ctcacttgtg | 900 |
| gagctcaagc agttcttcaa agagaacaat acagattcca ccatcaaaca cttttctt | 960 |
| cctactttaa tcaagtctct gtcaatggct ctaaccaaat atcccttcgt gaatagttgc | 1020 |
| ttcaacgcgg aatctctcga gatcattctc aaaggttcac ataatattgg agttgcaatg | 1080 |
| gccactgaac atggccttgt cgttcctaat ataaagaatg ttcagtcatt atctctgcta | 1140 |
| gagataacca aagagctgtc ccggttacaa catttggcag caaacaacaa acttaacccc | 1200 |
| gaggatgtga ctggtggaac cataactctg agtaacattg gagcaattgg tggtaaattc | 1260 |
| ggatcccttc ttttaaactt accggaagtt gcaatcatcg ttcttggaag aatcgagaaa | 1320 |
| gttccaaaat tctcaaaaga aggaactgtc tatcctgcat cgataatgat ggttaacatt | 1380 |
| gctgcggatc atagagttct agatggggca acggtagctc ggttttgctg ccagtggaaa | 1440 |
| gagtatgtcg | 1450 |

-continued

```
<210> SEQ ID NO 16
<211> LENGTH: 483
<212> TYPE: PRT
<213> ORGANISM: Arabidopsis thaliana

<400> SEQUENCE: 16
```

Met Ile Ala Arg Arg Ile Trp Arg Ser His Arg Phe Leu Arg Pro Phe
 1               5                  10                  15

Ser Ser Ser Ser Val Cys Ser Pro Pro Phe Arg Val Pro Glu Tyr Leu
                20                  25                  30

Ser Gln Ser Ser Ser Ser Pro Ala Ser Arg Pro Phe Phe Val His Pro
            35                  40                  45

Pro Thr Leu Met Lys Trp Gly Gly Gly Ser Arg Ser Trp Phe Ser Asn
        50                  55                  60

Glu Ala Met Ala Thr Asp Ser Asn Ser Gly Leu Ile Asp Val Pro Leu
 65                 70                  75                  80

Ala Gln Thr Gly Glu Gly Ile Ala Glu Cys Glu Leu Leu Lys Trp Phe
                85                  90                  95

Val Lys Glu Gly Asp Ser Val Glu Glu Phe Gln Pro Leu Cys Glu Val
            100                 105                 110

Gln Ser Asp Lys Ala Thr Ile Glu Ile Thr Ser Arg Phe Lys Gly Lys
        115                 120                 125

Val Ala Leu Ile Ser His Ser Pro Gly Asp Ile Ile Lys Val Gly Glu
130                 135                 140

Thr Leu Val Arg Leu Ala Val Glu Asp Ser Gln Asp Ser Leu Leu Thr
145                 150                 155                 160

Thr Asp Ser Ser Glu Ile Val Thr Leu Gly Gly Ser Lys Gln Gly Thr
                165                 170                 175

Glu Asn Leu Leu Gly Ala Leu Ser Thr Pro Ala Val Arg Asn Leu Ala
            180                 185                 190

Lys Asp Leu Gly Ile Asp Ile Asn Val Ile Thr Gly Thr Gly Lys Asp
        195                 200                 205

Gly Arg Val Leu Lys Glu Asp Val Leu Arg Phe Ser Asp Gln Lys Gly
    210                 215                 220

Phe Val Thr Asp Ser Val Ser Ser Glu His Ala Val Ile Gly Gly Asp
225                 230                 235                 240

Ser Val Ser Thr Lys Ala Ser Ser Asn Phe Glu Asp Lys Thr Val Pro
                245                 250                 255

Leu Arg Gly Phe Ser Arg Ala Met Val Lys Thr Met Thr Met Ala Thr
            260                 265                 270

Ser Val Pro His Phe His Phe Val Glu Glu Ile Asn Cys Asp Ser Leu
        275                 280                 285

Val Glu Leu Lys Gln Phe Phe Lys Glu Asn Asn Thr Asp Ser Thr Ile
    290                 295                 300

Lys His Thr Phe Leu Pro Thr Leu Ile Lys Ser Leu Ser Met Ala Leu
305                 310                 315                 320

Thr Lys Tyr Pro Phe Val Asn Ser Cys Phe Asn Ala Glu Ser Leu Glu
                325                 330                 335

Ile Ile Leu Lys Gly Ser His Asn Ile Gly Val Ala Met Ala Thr Glu
            340                 345                 350

His Gly Leu Val Val Pro Asn Ile Lys Asn Val Gln Ser Leu Ser Leu
        355                 360                 365

Leu Glu Ile Thr Lys Glu Leu Ser Arg Leu Gln His Leu Ala Ala Asn
    370                 375                 380

```
Asn Lys Leu Asn Pro Glu Asp Val Thr Gly Thr Ile Thr Leu Ser
385                 390                 395                 400

Asn Ile Gly Ala Ile Gly Gly Lys Phe Gly Ser Leu Leu Asn Leu
            405                 410                 415

Pro Glu Val Ala Ile Ile Val Leu Gly Arg Ile Glu Lys Val Pro Lys
            420                 425                 430

Phe Ser Lys Glu Gly Thr Val Tyr Pro Ala Ser Ile Met Met Val Asn
            435                 440                 445

Ile Ala Ala Asp His Arg Val Leu Asp Gly Ala Thr Val Ala Arg Phe
            450                 455                 460

Cys Cys Gln Trp Lys Glu Tyr Val Glu Lys Pro Glu Leu Leu Met Leu
465                 470                 475                 480

Gln Met Arg

<210> SEQ ID NO 17
<211> LENGTH: 24
<212> TYPE: DNA
<213> ORGANISM: Arabidopsis thaliana

<400> SEQUENCE: 17 gggcccccata tggcgacggc tttc                                            24

<210> SEQ ID NO 18
<211> LENGTH: 26
<212> TYPE: DNA
<213> ORGANISM: Arabidopsis thaliana

<400> SEQUENCE: 18
ggggcggccg ctaataacca cctaac                                           26

<210> SEQ ID NO 19
<211> LENGTH: 33
<212> TYPE: DNA
<213> ORGANISM: Arabidopsis thaliana

<400> SEQUENCE: 19
gggcccgcgg ccgctgatca tttggttcag cag                                   33

<210> SEQ ID NO 20
<211> LENGTH: 33
<212> TYPE: DNA
<213> ORGANISM: Arabidopsis thaliana

<400> SEQUENCE: 20
gggcccgcgg ccgctgatca tttggttcag cag                                   33

<210> SEQ ID NO 21
<211> LENGTH: 30
<212> TYPE: DNA
<213> ORGANISM: Arabidopsis thaliana

<400> SEQUENCE: 21
gggcccgtcg actcaaacat gaaagccagg                                       30

<210> SEQ ID NO 22
<211> LENGTH: 24
<212> TYPE: DNA
<213> ORGANISM: Arabidopsis thaliana

<400> SEQUENCE: 22 gggcccccata tgtcttcgat aatc                                            24
```

<210> SEQ ID NO 23
<211> LENGTH: 27
<212> TYPE: DNA
<213> ORGANISM: Arabidopsis thaliana

<400> SEQUENCE: 23
gggcccctcg agaccttcct gaagagc                                              27

<210> SEQ ID NO 24
<211> LENGTH: 27
<212> TYPE: DNA
<213> ORGANISM: Arabidopsis thaliana

<400> SEQUENCE: 24
gggcccctcg agaccttcct gaagagc                                              27

<210> SEQ ID NO 25
<211> LENGTH: 33
<212> TYPE: DNA
<213> ORGANISM: Arabidopsis thaliana

<400> SEQUENCE: 25
gggcccgaat tctcattact agtaattcac agt                                       33

<210> SEQ ID NO 26
<211> LENGTH: 24
<212> TYPE: DNA
<213> ORGANISM: Arabidopsis thaliana

<400> SEQUENCE: 26 gggcccccata tggcggtttc ttct                                                24

<210> SEQ ID NO 27
<211> LENGTH: 28
<212> TYPE: DNA
<213> ORGANISM: Arabidopsis thaliana

<400> SEQUENCE: 27
gggcccccat ggcaatttca ggattctt                                             28

<210> SEQ ID NO 28
<211> LENGTH: 24
<212> TYPE: DNA
<213> ORGANISM: Arabidopsis thaliana

<400> SEQUENCE: 28 gggcccccata tgtcttcgat aatc                                                24

<210> SEQ ID NO 29
<211> LENGTH: 26
<212> TYPE: DNA
<213> ORGANISM: Arabidopsis thaliana

<400> SEQUENCE: 29
gggcccccat ggcgacggct ttcgct                                               26

<210> SEQ ID NO 30
<211> LENGTH: 31
<212> TYPE: DNA
<213> ORGANISM: Arabidopsis thaliana

<400> SEQUENCE: 30
gggccctgat catattattg gtggattgct t    31

<210> SEQ ID NO 31
<211> LENGTH: 27
<212> TYPE: DNA
<213> ORGANISM: Arabidopsis thaliana

<400> SEQUENCE: 31
gggcccctcg agatcgcttt ggacacc    27

<210> SEQ ID NO 32
<211> LENGTH: 32
<212> TYPE: DNA
<213> ORGANISM: Arabidopsis thaliana

<400> SEQUENCE: 32
gggcccgcgg ccgcattatt ggtggattgc tt    32

<210> SEQ ID NO 33
<211> LENGTH: 428
<212> TYPE: PRT
<213> ORGANISM: Arabidopsis thaliana

<400> SEQUENCE: 33

Met Ala Thr Ala Phe Ala Pro Thr Lys Leu Thr Ala Thr Val Pro Leu
 1               5                  10                  15

His Gly Ser His Glu Asn Arg Leu Leu Leu Pro Ile Arg Leu Ala Pro
            20                  25                  30

Pro Ser Ser Phe Leu Gly Ser Thr Arg Ser Leu Ser Leu Arg Arg Leu
        35                  40                  45

Asn His Ser Asn Ala Thr Arg Arg Ser Pro Val Val Ser Val Gln Glu
    50                  55                  60

Val Val Lys Glu Lys Gln Ser Thr Asn Thr Ser Leu Leu Ile Thr
 65                  70                  75                  80

Lys Glu Glu Gly Leu Glu Leu Tyr Glu Asp Met Ile Leu Gly Arg Ser
                85                  90                  95

Phe Glu Asp Met Cys Ala Gln Met Tyr Tyr Arg Gly Lys Met Phe Gly
            100                 105                 110

Phe Val His Leu Tyr Asn Gly Gln Glu Ala Val Ser Thr Gly Phe Ile
        115                 120                 125

Lys Leu Leu Thr Lys Ser Asp Ser Val Val Ser Thr Tyr Arg Asp His
    130                 135                 140

Val His Ala Leu Ser Lys Gly Val Ser Ala Arg Ala Val Met Ser Glu
145                 150                 155                 160

Leu Phe Gly Lys Val Thr Gly Cys Cys Arg Gly Gln Gly Gly Ser Met
                165                 170                 175

His Met Phe Ser Lys Glu His Asn Met Leu Gly Gly Phe Ala Phe Ile
            180                 185                 190

Gly Glu Gly Ile Pro Val Ala Thr Gly Ala Ala Phe Ser Ser Lys Tyr
        195                 200                 205

Arg Arg Glu Val Leu Lys Gln Asp Cys Asp Asp Val Thr Val Ala Phe
    210                 215                 220

Phe Gly Asp Gly Thr Cys Asn Asn Gly Gln Phe Phe Glu Cys Leu Asn
225                 230                 235                 240

Met Ala Ala Leu Tyr Lys Leu Pro Ile Ile Phe Val Val Glu Asn Asn
                245                 250                 255

Leu Trp Ala Ile Gly Met Ser His Leu Arg Ala Thr Ser Asp Pro Glu

```
                260                 265                 270
Ile Trp Lys Lys Gly Pro Ala Phe Gly Met Pro Gly Val His Val Asp
        275                 280                 285

Gly Met Asp Val Leu Lys Val Arg Glu Val Ala Lys Glu Ala Val Thr
        290                 295                 300

Arg Ala Arg Arg Gly Glu Gly Pro Thr Leu Val Glu Cys Glu Thr Tyr
305                 310                 315                 320

Arg Phe Arg Gly His Ser Leu Ala Asp Pro Asp Glu Leu Arg Asp Ala
                325                 330                 335

Ala Glu Lys Ala Lys Tyr Ala Ala Arg Asp Pro Ile Ala Ala Leu Lys
                340                 345                 350

Lys Tyr Leu Ile Glu Asn Lys Leu Ala Lys Glu Ala Glu Leu Lys Ser
        355                 360                 365

Ile Glu Lys Lys Ile Asp Glu Leu Val Glu Glu Ala Val Glu Phe Ala
        370                 375                 380

Asp Ala Ser Pro Gln Pro Gly Arg Ser Gln Leu Leu Glu Asn Val Phe
385                 390                 395                 400

Ala Asp Pro Lys Gly Phe Gly Ile Gly Pro Asp Gly Arg Tyr Arg Cys
                405                 410                 415

Glu Asp Pro Lys Phe Thr Glu Gly Thr Ala Gln Val
                420                 425

<210> SEQ ID NO 34
<211> LENGTH: 344
<212> TYPE: PRT
<213> ORGANISM: P. purpurea

<400> SEQUENCE: 34

Met Ser Tyr Pro Lys Lys Val Glu Leu Pro Leu Thr Asn Cys Asn Gln
  1               5                  10                  15

Ile Asn Leu Thr Lys His Lys Leu Leu Val Leu Tyr Glu Asp Met Leu
             20                  25                  30

Leu Gly Arg Asn Phe Glu Asp Met Cys Ala Gln Met Tyr Tyr Lys Gly
         35                  40                  45

Lys Met Phe Gly Phe Val His Leu Tyr Asn Gly Gln Glu Ala Val Ser
     50                  55                  60

Thr Gly Val Ile Lys Leu Leu Asp Ser Lys Asp Tyr Val Cys Ser Thr
 65                  70                  75                  80

Tyr Arg Asp His Val His Ala Leu Ser Lys Gly Val Pro Ser Gln Asn
                 85                  90                  95

Val Met Ala Glu Leu Phe Gly Lys Glu Thr Gly Cys Ser Arg Gly Arg
            100                 105                 110

Gly Gly Ser Met His Ile Phe Ser Ala Pro His Asn Phe Leu Gly Gly
        115                 120                 125

Phe Ala Phe Ile Ala Glu Gly Ile Pro Val Ala Thr Gly Ala Ala Phe
    130                 135                 140

Gln Ser Ile Tyr Arg Gln Gln Val Leu Lys Glu Pro Gly Glu Leu Arg
145                 150                 155                 160

Val Thr Ala Cys Phe Phe Gly Asp Gly Thr Thr Asn Asn Gly Gln Phe
                165                 170                 175

Phe Glu Cys Leu Asn Met Ala Val Leu Trp Lys Leu Pro Ile Ile Phe
            180                 185                 190

Val Val Glu Asn Asn Gln Trp Ala Ile Gly Met Ala His His Arg Ser
        195                 200                 205
```

```
Ser Ser Ile Pro Glu Ile His Lys Lys Ala Glu Ala Phe Gly Leu Pro
        210                 215                 220

Gly Ile Glu Val Asp Gly Met Asp Val Leu Ala Val Arg Gln Val Ala
225                 230                 235                 240

Glu Lys Ala Val Glu Arg Ala Arg Gln Gly Gln Gly Pro Thr Leu Ile
                245                 250                 255

Glu Ala Leu Thr Tyr Arg Phe Arg Gly His Ser Leu Ala Asp Pro Asp
            260                 265                 270

Glu Leu Arg Ser Arg Gln Glu Lys Glu Ala Trp Val Ala Arg Asp Pro
        275                 280                 285

Ile Lys Lys Leu Lys Lys His Ile Leu Asp Asn Gln Ile Ala Ser Ser
    290                 295                 300

Asp Glu Leu Asn Asp Ile Gln Ser Ser Val Lys Ile Asp Leu Glu Gln
305                 310                 315                 320

Ser Val Glu Phe Ala Met Ser Ser Pro Glu Pro Asn Ile Ser Glu Leu
                325                 330                 335

Lys Arg Tyr Leu Phe Ala Asp Asn
            340

<210> SEQ ID NO 35
<211> LENGTH: 389
<212> TYPE: PRT
<213> ORGANISM: Arabidopsis thaliana

<400> SEQUENCE: 35

Met Ala Leu Ser Arg Leu Ser Ser Arg Ser Asn Ile Ile Thr Arg Pro
1               5                   10                  15

Phe Ser Ala Ala Phe Ser Arg Leu Ile Ser Thr Asp Thr Thr Pro Ile
            20                  25                  30

Thr Ile Glu Thr Ser Leu Pro Phe Thr Ala His Leu Cys Asp Pro Pro
        35                  40                  45

Ser Arg Ser Val Glu Ser Ser Gln Glu Leu Leu Asp Phe Phe Arg
    50                  55                  60

Thr Met Ala Leu Met Arg Arg Met Glu Ile Ala Ala Asp Ser Leu Tyr
65                  70                  75                  80

Lys Ala Asn Val Ile Arg Gly Phe Cys His Leu Tyr Asp Gly Gln Glu
                85                  90                  95

Ala Val Ala Ile Gly Met Glu Ala Ala Ile Thr Lys Lys Asp Ala Ile
            100                 105                 110

Ile Thr Ala Tyr Arg Asp His Cys Ile Phe Leu Gly Arg Gly Gly Ser
        115                 120                 125

Leu His Glu Val Phe Ser Glu Leu Met Gly Arg Gln Ala Gly Cys Ser
    130                 135                 140

Lys Gly Lys Gly Gly Ser Met His Phe Tyr Lys Lys Glu Ser Ser Phe
145                 150                 155                 160

Tyr Gly Gly His Gly Ile Val Gly Ala Gln Val Pro Leu Gly Cys Gly
                165                 170                 175

Ile Ala Phe Ala Gln Lys Tyr Asn Lys Glu Ala Val Thr Phe Ala
            180                 185                 190

Leu Tyr Gly Asp Gly Ala Ala Asn Gln Gly Gln Leu Phe Glu Ala Leu
        195                 200                 205

Asn Ile Ser Ala Leu Trp Asp Leu Pro Ala Ile Leu Val Cys Glu Asn
    210                 215                 220

Asn His Tyr Gly Met Gly Thr Ala Glu Trp Arg Ala Ala Lys Ser Pro
225                 230                 235                 240
```

-continued

```
Ser Tyr Tyr Lys Arg Gly Asp Tyr Val Pro Gly Leu Lys Val Asp Gly
            245                 250                 255

Met Asp Ala Phe Ala Val Lys Gln Ala Cys Lys Phe Ala Lys Gln His
        260                 265                 270

Ala Leu Glu Lys Gly Pro Ile Ile Leu Glu Met Asp Thr Tyr Arg Tyr
    275                 280                 285

His Gly His Ser Met Ser Asp Pro Gly Ser Thr Tyr Arg Thr Arg Asp
290                 295                 300

Glu Ile Ser Gly Val Arg Gln Glu Arg Asp Pro Ile Glu Arg Ile Lys
305                 310                 315                 320

Lys Leu Val Leu Ser His Asp Leu Ala Thr Glu Lys Glu Leu Lys Asp
                325                 330                 335

Met Glu Lys Glu Ile Arg Lys Glu Val Asp Asp Ala Ile Ala Lys Ala
            340                 345                 350

Lys Asp Cys Pro Met Pro Glu Pro Ser Glu Leu Phe Thr Asn Val Tyr
        355                 360                 365

Val Lys Gly Phe Gly Thr Glu Ser Phe Gly Pro Asp Arg Lys Glu Val
    370                 375                 380

Lys Ala Ser Leu Pro
385

<210> SEQ ID NO 36
<211> LENGTH: 390
<212> TYPE: PRT
<213> ORGANISM: H. sapiens II

<400> SEQUENCE: 36

Met Arg Lys Met Leu Ala Ala Val Ser Arg Val Leu Ser Gly Ala Ser
  1               5                  10                  15

Gln Lys Pro Ala Ser Arg Val Leu Val Ala Ser Arg Asn Phe Ala Asn
            20                  25                  30

Asp Ala Thr Phe Glu Ile Lys Lys Cys Asp Leu His Arg Leu Glu Glu
        35                  40                  45

Gly Pro Pro Val Thr Thr Val Leu Thr Arg Glu Asp Gly Leu Lys Tyr
    50                  55                  60

Tyr Arg Met Met Gln Thr Val Arg Arg Met Glu Leu Lys Ala Asp Gln
65                  70                  75                  80

Leu Tyr Lys Gln Lys Ile Ile Arg Gly Phe Cys His Leu Cys Asp Gly
                85                  90                  95

Gln Glu Ala Cys Cys Val Gly Leu Glu Ala Gly Ile Asn Pro Thr Asp
            100                 105                 110

His Leu Ile Thr Ala Tyr Arg Ala His Gly Phe Thr Phe Thr Arg Gly
        115                 120                 125

Leu Ser Val Arg Glu Ile Leu Ala Glu Leu Thr Gly Arg Lys Gly Gly
    130                 135                 140

Cys Ala Lys Gly Lys Gly Gly Ser Met His Met Tyr Ala Lys Asn Phe
145                 150                 155                 160

Tyr Gly Gly Asn Gly Ile Val Gly Ala Gln Val Pro Leu Gly Ala Gly
                165                 170                 175

Ile Ala Leu Ala Cys Lys Tyr Asn Gly Lys Asp Glu Val Cys Leu Thr
            180                 185                 190

Leu Tyr Gly Asp Gly Ala Ala Asn Gln Gly Gln Ile Phe Glu Ala Tyr
        195                 200                 205

Asn Met Ala Ala Leu Trp Lys Leu Pro Cys Ile Phe Ile Cys Glu Asn
```

```
            210                 215                 220
Asn Arg Tyr Gly Met Gly Thr Ser Val Glu Arg Ala Ala Ser Thr
225                 230                 235                 240

Asp Tyr Tyr Lys Arg Gly Asp Phe Ile Pro Gly Leu Arg Val Asp Gly
                245                 250                 255

Met Asp Ile Leu Cys Val Arg Glu Ala Thr Arg Phe Ala Ala Ala Tyr
                260                 265                 270

Cys Arg Ser Gly Lys Gly Pro Ile Leu Met Glu Leu Gln Thr Tyr Arg
                275                 280                 285

Tyr His Gly His Ser Met Ser Asp Pro Gly Val Ser Tyr Arg Thr Arg
                290                 295                 300

Glu Glu Ile Gln Glu Val Arg Ser Lys Ser Asp Pro Ile Met Leu Leu
305                 310                 315                 320

Lys Asp Arg Met Val Asn Ser Asn Leu Ala Ser Val Glu Glu Leu Lys
                325                 330                 335

Glu Ile Asp Val Glu Val Arg Lys Glu Ile Glu Asp Ala Ala Gln Phe
                340                 345                 350

Ala Thr Ala Asp Pro Glu Pro Pro Leu Glu Glu Leu Gly Tyr His Ile
                355                 360                 365

Tyr Ser Ser Asp Pro Pro Phe Glu Val Arg Gly Ala Asn Gln Trp Ile
                370                 375                 380

Lys Phe Lys Ser Val Ser
385                 390

<210> SEQ ID NO 37
<211> LENGTH: 420
<212> TYPE: PRT
<213> ORGANISM: S. cerevisiae

<400> SEQUENCE: 37

Met Leu Ala Ala Ser Phe Lys Arg Gln Pro Ser Gln Leu Val Arg Gly
  1               5                  10                  15

Leu Gly Ala Val Leu Arg Thr Pro Thr Arg Ile Gly His Val Arg Thr
                 20                  25                  30

Met Ala Thr Leu Lys Thr Thr Asp Lys Lys Ala Pro Glu Asp Ile Glu
                 35                  40                  45

Gly Ser Asp Thr Val Gln Ile Glu Leu Pro Glu Ser Ser Phe Glu Ser
         50                  55                  60

Tyr Met Leu Glu Pro Pro Asp Leu Ser Tyr Glu Thr Ser Lys Ala Thr
 65                  70                  75                  80

Leu Leu Gln Met Tyr Lys Asp Met Val Ile Ile Arg Arg Met Glu Met
                 85                  90                  95

Ala Cys Asp Ala Leu Tyr Lys Ala Lys Lys Ile Arg Gly Phe Cys His
                100                 105                 110

Leu Ser Val Gly Gln Glu Ala Ile Ala Val Gly Ile Glu Asn Ala Ile
                115                 120                 125

Thr Lys Leu Asp Ser Ile Ile Thr Ser Tyr Arg Cys His Gly Phe Thr
                130                 135                 140

Phe Met Arg Gly Ala Ser Val Lys Ala Val Leu Ala Glu Leu Met Gly
145                 150                 155                 160

Arg Arg Ala Gly Val Ser Tyr Gly Lys Gly Gly Ser Met His Leu Tyr
                165                 170                 175

Ala Pro Gly Phe Tyr Gly Gly Asn Gly Ile Val Gly Ala Gln Val Pro
                180                 185                 190
```

```
Leu Gly Ala Gly Leu Ala Phe Ala His Gln Tyr Lys Asn Glu Asp Ala
        195                 200                 205

Cys Ser Phe Thr Leu Tyr Gly Asp Gly Ala Ser Asn Gln Gly Gln Val
        210                 215                 220

Phe Glu Ser Phe Asn Met Ala Lys Leu Trp Asn Leu Pro Val Val Phe
225                 230                 235                 240

Cys Cys Glu Asn Asn Lys Tyr Gly Met Gly Thr Ala Ala Ser Arg Ser
                245                 250                 255

Ser Ala Met Thr Glu Tyr Phe Lys Arg Gly Gln Tyr Ile Pro Gly Leu
        260                 265                 270

Lys Val Asn Gly Met Asp Ile Leu Ala Val Tyr Gln Ala Ser Lys Phe
        275                 280                 285

Ala Lys Asp Trp Cys Leu Ser Gly Lys Gly Pro Leu Val Leu Glu Tyr
        290                 295                 300

Glu Thr Tyr Arg Tyr Gly Gly His Ser Met Ser Asp Pro Gly Thr Thr
305                 310                 315                 320

Tyr Arg Thr Arg Asp Glu Ile Gln His Met Arg Ser Lys Asn Asp Pro
                325                 330                 335

Ile Ala Gly Leu Lys Met His Leu Ile Asp Leu Gly Ile Ala Thr Glu
        340                 345                 350

Ala Glu Val Lys Ala Tyr Asp Lys Ser Ala Arg Lys Tyr Val Asp Glu
        355                 360                 365

Gln Val Glu Leu Ala Asp Ala Ala Pro Pro Glu Ala Lys Leu Ser
        370                 375                 380

Ile Leu Phe Glu Asp Val Tyr Val Lys Gly Thr Glu Thr Pro Thr Leu
385                 390                 395                 400

Arg Gly Arg Ile Pro Glu Asp Thr Trp Asp Phe Lys Lys Gln Gly Phe
                405                 410                 415

Ala Ser Arg Asp
        420

<210> SEQ ID NO 38
<211> LENGTH: 396
<212> TYPE: PRT
<213> ORGANISM: A. suum I

<400> SEQUENCE: 38

Met Ile Phe Val Phe Ala Asn Ile Phe Lys Val Pro Thr Val Ser Pro
1               5                   10                  15

Ser Val Met Ala Ile Ser Val Arg Leu Ala Ser Thr Glu Ala Thr Phe
                20                  25                  30

Gln Thr Lys Pro Phe Lys Leu His Lys Leu Asp Ser Gly Pro Asp Ile
            35                  40                  45

Asn Val His Val Thr Lys Glu Asp Ala Val His Tyr Tyr Thr Gln Met
        50                  55                  60

Leu Thr Ile Arg Arg Met Glu Ser Ala Ala Gly Asn Leu Tyr Lys Glu
65                  70                  75                  80

Lys Lys Val Arg Gly Phe Cys His Leu Tyr Ser Gly Gln Glu Ala Cys
                85                  90                  95

Ala Val Gly Thr Lys Ala Ala Met Asp Ala Gly Asp Ala Ala Val Thr
            100                 105                 110

Ala Tyr Arg Cys His Gly Trp Thr Tyr Leu Ser Gly Ser Ser Val Ala
        115                 120                 125

Lys Val Leu Cys Glu Leu Thr Gly Arg Ile Thr Gly Asn Val Tyr Gly
        130                 135                 140
```

-continued

```
Lys Gly Gly Ser Met His Met Tyr Gly Glu Asn Phe Tyr Gly Gly Asn
145                 150                 155                 160

Gly Ile Val Gly Ala Gln Gln Pro Leu Gly Thr Gly Ile Ala Phe Ala
                165                 170                 175

Met Lys Tyr Arg Lys Glu Lys Asn Val Cys Ile Thr Met Phe Gly Asp
            180                 185                 190

Gly Ala Thr Asn Gln Gly Gln Leu Phe Glu Ser Met Asn Met Ala Lys
        195                 200                 205

Leu Trp Asp Leu Pro Val Leu Tyr Val Cys Glu Asn Asn Gly Tyr Gly
    210                 215                 220

Met Gly Thr Ala Ala Ala Arg Ser Ser Ala Ser Thr Asp Tyr Tyr Thr
225                 230                 235                 240

Arg Gly Asp Tyr Val Pro Gly Ile Trp Val Asp Gly Met Asp Val Leu
                245                 250                 255

Ala Val Arg Gln Ala Val Arg Trp Ala Lys Glu Trp Cys Asn Ala Gly
            260                 265                 270

Lys Gly Pro Leu Met Ile Glu Met Ala Thr Tyr Arg Tyr Ser Gly His
        275                 280                 285

Ser Met Ser Asp Pro Gly Thr Ser Tyr Arg Thr Arg Glu Glu Val Gln
    290                 295                 300

Glu Val Arg Lys Thr Arg Asp Pro Ile Thr Gly Phe Lys Asp Lys Ile
305                 310                 315                 320

Val Thr Ala Gly Leu Val Thr Glu Asp Glu Ile Lys Glu Ile Asp Lys
                325                 330                 335

Gln Val Arg Lys Glu Ile Asp Ala Ala Val Lys Gln Ala His Thr Asp
            340                 345                 350

Lys Glu Ser Pro Val Glu Leu Met Leu Thr Asp Ile Tyr Tyr Asn Thr
        355                 360                 365

Pro Ala Gln Tyr Val Arg Cys Thr Thr Asp Glu Val Leu Gln Lys Tyr
    370                 375                 380

Leu Thr Ser Glu Glu Ala Val Lys Ala Leu Ala Lys
385                 390                 395

<210> SEQ ID NO 39
<211> LENGTH: 370
<212> TYPE: PRT
<213> ORGANISM: M. capricolum

<400> SEQUENCE: 39

Met Thr Tyr Leu Gly Lys Phe Asp Pro Leu Lys Asn Glu Lys Val Cys
  1               5                  10                  15

Val Leu Asp Lys Asp Gly Lys Val Ile Asn Pro Lys Leu Met Pro Lys
             20                  25                  30

Ile Ser Asp Gln Glu Ile Leu Glu Ala Tyr Lys Ile Met Asn Leu Ser
         35                  40                  45

Arg Arg Gln Asp Ile Tyr Gln Asn Thr Met Gln Arg Gln Gly Arg Leu
     50                  55                  60

Leu Ser Phe Leu Ser Ser Thr Gly Gln Glu Ala Cys Glu Val Ala Tyr
 65                  70                  75                  80

Ile Asn Ala Leu Asn Lys Lys Thr Asp His Phe Val Ser Gly Tyr Arg
                 85                  90                  95

Asn Asn Ala Ala Trp Leu Ala Met Gly Gln Leu Val Arg Asn Ile Met
            100                 105                 110

Leu Tyr Trp Ile Gly Asn Glu Ala Gly Gly Lys Ala Pro Glu Gly Val
```

```
            115                 120                 125
Asn Cys Leu Pro Pro Asn Ile Val Ile Gly Ser Gln Tyr Ser Gln Ala
    130                 135                 140

Thr Gly Ile Ala Phe Ala Asp Lys Tyr Arg Lys Thr Gly Gly Val Val
145                 150                 155                 160

Val Thr Thr Thr Gly Asp Gly Gly Ser Ser Glu Gly Glu Thr Tyr Glu
                165                 170                 175

Ala Met Asn Phe Ala Lys Leu His Glu Val Pro Cys Ile Phe Val Ile
            180                 185                 190

Glu Asn Asn Lys Trp Ala Ile Ser Thr Ala Arg Ser Glu Gln Thr Lys
        195                 200                 205

Ser Ile Asn Phe Ala Val Lys Gly Ile Ala Thr Gly Ile Pro Ser Ile
    210                 215                 220

Ile Val Asp Gly Asn Asp Tyr Leu Ala Cys Ile Gly Val Phe Lys Glu
225                 230                 235                 240

Val Val Glu Tyr Val Arg Lys Gly Asn Gly Pro Val Leu Val Glu Cys
                245                 250                 255

Asp Thr Tyr Arg Leu Gly Ala His Ser Ser Ser Asp Asn Pro Asp Ala
            260                 265                 270

Tyr Arg Pro Lys Gly Glu Phe Glu Met Ala Lys Phe Asp Pro Leu
        275                 280                 285

Ile Arg Leu Lys Gln Tyr Leu Ile Asp Lys Lys Ile Trp Ser Asp Glu
    290                 295                 300

Gln Gln Ala Gln Leu Glu Ala Glu Gln Asp Lys Phe Val Ala Asp Glu
305                 310                 315                 320

Phe Ala Trp Val Glu Lys Asn Lys Asn Tyr Asp Leu Ile Asp Ile Phe
                325                 330                 335

Lys Tyr Gln Tyr Asp Lys Met Asp Ile Phe Leu Glu Glu Gln Tyr Lys
            340                 345                 350

Glu Ala Lys Glu Phe Phe Glu Lys Tyr Pro Glu Ser Lys Glu Gly Gly
        355                 360                 365

His His
    370

<210> SEQ ID NO 40
<211> LENGTH: 369
<212> TYPE: PRT
<213> ORGANISM: B. subtilis

<400> SEQUENCE: 40

Met Gly Val Lys Thr Phe Gln Phe Pro Phe Ala Glu Gln Leu Glu Lys
1               5                   10                  15

Val Ala Glu Gln Phe Pro Thr Phe Gln Ile Leu Asn Glu Glu Gly Glu
            20                  25                  30

Val Val Asn Glu Glu Ala Met Pro Glu Leu Ser Asp Glu Gln Leu Lys
        35                  40                  45

Glu Leu Met Arg Met Val Tyr Thr Arg Ile Leu Asp Gln Arg Ser
    50                  55                  60

Ile Ser Leu Asn Arg Gln Gly Arg Leu Gly Phe Tyr Ala Pro Thr Ala
65                  70                  75                  80

Gly Gln Glu Ala Ser Gln Ile Ala Ser His Phe Ala Leu Glu Lys Glu
                85                  90                  95

Asp Phe Ile Leu Pro Gly Tyr Arg Asp Val Pro Gln Ile Ile Trp His
            100                 105                 110
```

```
Gly Leu Pro Leu Tyr Gln Ala Phe Leu Phe Ser Arg Gly His Phe His
            115                 120                 125

Gly Asn Gln Ile Pro Glu Gly Val Asn Val Leu Pro Pro Gln Ile Ile
        130                 135                 140

Ile Gly Ala Gln Tyr Ile Gln Ala Ala Gly Val Ala Leu Gly Leu Lys
145                 150                 155                 160

Met Arg Gly Lys Lys Ala Val Ala Ile Thr Tyr Thr Gly Asp Gly Gly
                165                 170                 175

Thr Ser Gln Gly Asp Phe Tyr Glu Gly Ile Asn Phe Ala Gly Ala Phe
            180                 185                 190

Lys Ala Pro Ala Ile Phe Val Val Gln Asn Asn Arg Phe Ala Ile Ser
        195                 200                 205

Thr Pro Val Glu Lys Gln Thr Val Ala Lys Thr Leu Ala Gln Lys Ala
    210                 215                 220

Val Ala Ala Gly Ile Pro Gly Ile Gln Val Asp Gly Met Asp Pro Leu
225                 230                 235                 240

Ala Val Tyr Ala Ala Val Lys Ala Ala Arg Glu Arg Ala Ile Asn Gly
                245                 250                 255

Glu Gly Pro Thr Leu Ile Glu Thr Leu Cys Phe Arg Tyr Gly Pro His
            260                 265                 270

Thr Met Ser Gly Asp Asp Pro Thr Arg Tyr Arg Ser Lys Glu Leu Glu
        275                 280                 285

Asn Glu Trp Ala Lys Lys Asp Pro Leu Val Arg Phe Arg Lys Phe Leu
    290                 295                 300

Glu Ala Lys Gly Leu Trp Ser Glu Glu Glu Asn Asn Val Ile Glu
305                 310                 315                 320

Gln Ala Lys Glu Glu Ile Lys Glu Ala Ile Lys Lys Ala Asp Glu Thr
                325                 330                 335

Pro Lys Gln Lys Val Thr Asp Leu Ile Ser Ile Met Phe Glu Glu Leu
            340                 345                 350

Pro Phe Asn Leu Lys Glu Gln Tyr Glu Ile Tyr Lys Glu Lys Glu Ser
        355                 360                 365

Lys

<210> SEQ ID NO 41
<211> LENGTH: 129
<212> TYPE: PRT
<213> ORGANISM: Artificial Sequence
<220> FEATURE:
<223> OTHER INFORMATION: Description of Artificial Sequence:  Consensus

<400> SEQUENCE: 41

Leu Tyr Met Arg Arg Glu Leu Tyr Gly Phe His Leu Gly Gln Glu Ala
  1               5                  10                  15

Gly Lys Asp Tyr Arg His Gly Ser Val Glu Leu Gly Gly Gly Gly
            20                  25                  30

Ser Met His Phe Gly Ile Gly Ala Gln Pro Gly Ala Phe Ala Lys
         35                  40                  45

Tyr Arg Val Thr Gly Asp Gly Asn Gln Gly Gln Phe Glu Asn Met Ala
     50                  55                  60

Leu Trp Leu Pro Ile Phe Val Glu Asn Asn Gly Thr Ala Arg Lys Gly
 65                  70                  75                  80

Pro Gly Val Asp Gly Met Asp Leu Ala Val Ala Lys Ala Gly Gly Pro
                 85                  90                  95

Leu Glu Thr Tyr Arg Tyr Gly His Ser Met Ser Asp Pro Tyr Arg Arg
```

-continued

```
                  100                 105                 110
Glu Asp Pro Ile Leu Lys Leu Ala Glu Glu Lys Lys Ala Pro Pro
            115                 120                 125
Leu

<210> SEQ ID NO 42
<211> LENGTH: 406
<212> TYPE: PRT
<213> ORGANISM: Arabidopsis thaliana

<400> SEQUENCE: 42

Met Ser Ser Ile Ile His Gly Ala Gly Ala Thr Thr Thr Leu Ser
 1               5                  10                  15
Thr Phe Asn Ser Val Asp Ser Lys Lys Leu Phe Val Ala Pro Ser Arg
            20                  25                  30
Thr Asn Leu Ser Val Arg Ser Gln Arg Tyr Ile Val Ala Gly Ser Asp
            35                  40                  45
Ala Ser Lys Lys Ser Phe Gly Ser Gly Leu Arg Val Arg His Ser Gln
            50                  55                  60
Lys Leu Ile Pro Asn Ala Val Ala Thr Lys Glu Ala Asp Thr Ser Ala
 65                  70                  75                  80
Ser Thr Gly His Glu Leu Leu Leu Phe Glu Ala Leu Gln Glu Gly Leu
                    85                  90                  95
Glu Glu Glu Met Asp Arg Asp Pro His Val Cys Val Met Gly Glu Asp
                100                 105                 110
Val Gly His Tyr Gly Gly Ser Tyr Lys Val Thr Lys Gly Leu Ala Asp
            115                 120                 125
Lys Phe Gly Asp Leu Arg Val Leu Asp Thr Pro Ile Cys Glu Asn Ala
130                 135                 140
Phe Thr Gly Met Gly Ile Gly Ala Ala Met Thr Gly Leu Arg Pro Val
145                 150                 155                 160
Ile Glu Gly Met Asn Met Gly Phe Leu Leu Leu Ala Phe Asn Gln Ile
                165                 170                 175
Ser Asn Asn Cys Gly Met Leu His Tyr Thr Ser Gly Gly Gln Phe Thr
            180                 185                 190
Ile Pro Val Val Ile Arg Gly Pro Gly Gly Val Gly Arg Gln Leu Gly
            195                 200                 205
Ala Glu His Ser Gln Arg Leu Glu Ser Tyr Phe Gln Ser Ile Pro Gly
            210                 215                 220
Ile Gln Met Val Ala Cys Ser Thr Pro Tyr Asn Ala Lys Gly Leu Met
225                 230                 235                 240
Lys Ala Ala Ile Arg Ser Glu Asn Pro Val Ile Leu Phe Glu His Val
                245                 250                 255
Leu Leu Tyr Asn Leu Lys Glu Lys Ile Pro Asp Glu Asp Tyr Ile Cys
            260                 265                 270
Asn Leu Glu Glu Ala Glu Met Val Arg Pro Gly Glu His Ile Thr Ile
            275                 280                 285
Leu Thr Tyr Ser Arg Met Arg Tyr His Val Met Gln Ala Ala Lys Thr
            290                 295                 300
Leu Val Asn Lys Gly Tyr Asp Pro Glu Val Ile Asp Ile Arg Ser Leu
305                 310                 315                 320
Lys Pro Phe Asp Leu His Thr Ile Gly Asn Ser Val Lys Lys Thr His
                325                 330                 335
Arg Val Leu Ile Val Glu Glu Cys Met Arg Thr Gly Gly Ile Gly Ala
```

-continued

```
                    340                 345                 350
Ser Leu Thr Ala Ala Ile Asn Glu Asn Phe His Asp Tyr Leu Asp Ala
            355                 360                 365

Pro Val Met Cys Leu Ser Ser Gln Asp Val Pro Thr Pro Tyr Ala Gly
        370                 375                 380

Thr Leu Glu Glu Trp Thr Val Val Gln Pro Ala Gln Ile Val Thr Ala
385                 390                 395                 400

Val Glu Gln Leu Cys Gln
                405

<210> SEQ ID NO 43
<211> LENGTH: 331
<212> TYPE: PRT
<213> ORGANISM: P. purpurea

<400> SEQUENCE: 43

Met Ser Lys Val Phe Met Phe Asp Ala Leu Arg Ala Ala Thr Asp Glu
 1               5                  10                  15

Glu Met Glu Lys Asp Leu Thr Val Cys Val Ile Gly Glu Asp Val Gly
                20                  25                  30

His Tyr Gly Gly Ser Tyr Lys Val Thr Lys Asp Leu His Ser Lys Tyr
            35                  40                  45

Gly Asp Leu Arg Val Leu Asp Thr Pro Ile Ala Glu Asn Ser Phe Thr
        50                  55                  60

Gly Met Ala Ile Gly Ala Ala Ile Thr Gly Leu Arg Pro Ile Val Glu
65                  70                  75                  80

Gly Met Asn Met Ser Phe Leu Leu Leu Ala Phe Asn Gln Ile Ser Asn
                85                  90                  95

Asn Ala Gly Met Leu Arg Tyr Thr Ser Gly Gly Asn Phe Thr Leu Pro
            100                 105                 110

Leu Val Ile Arg Gly Pro Gly Gly Val Gly Arg Gln Leu Gly Ala Glu
        115                 120                 125

His Ser Gln Arg Leu Glu Ala Tyr Phe Gln Ala Ile Pro Gly Leu Lys
    130                 135                 140

Ile Val Ala Cys Ser Thr Pro Tyr Asn Ala Lys Gly Leu Leu Lys Ser
145                 150                 155                 160

Ala Ile Arg Asp Asn Asn Pro Val Val Phe Phe Glu His Val Leu Leu
                165                 170                 175

Tyr Asn Leu Gln Glu Glu Ile Pro Glu Asp Glu Tyr Leu Ile Pro Leu
            180                 185                 190

Asp Lys Ala Glu Val Val Arg Lys Gly Lys Asp Ile Thr Ile Leu Thr
        195                 200                 205

Tyr Ser Arg Met Arg His His Val Thr Glu Ala Leu Pro Leu Leu Leu
    210                 215                 220

Asn Asp Gly Tyr Asp Pro Glu Val Leu Asp Leu Ile Ser Leu Lys Pro
225                 230                 235                 240

Leu Asp Ile Asp Ser Ile Ser Val Ser Val Lys Lys Thr His Arg Val
                245                 250                 255

Leu Ile Val Glu Glu Cys Met Lys Thr Ala Gly Ile Gly Ala Glu Leu
            260                 265                 270

Ile Ala Gln Ile Asn Glu His Leu Phe Asp Glu Leu Asp Ala Pro Val
        275                 280                 285

Val Arg Leu Ser Ser Gln Asp Ile Pro Thr Pro Tyr Asn Gly Ser Leu
    290                 295                 300
```

-continued

Glu Gln Ala Thr Val Ile Gln Pro His Gln Ile Ile Asp Ala Val Lys
305                 310                 315                 320

Asn Ile Val Asn Ser Ser Lys Thr Ile Thr Thr
                325                 330

<210> SEQ ID NO 44
<211> LENGTH: 363
<212> TYPE: PRT
<213> ORGANISM: Arabidopsis thaliana

<400> SEQUENCE: 44

Met Leu Gly Ile Leu Arg Gln Arg Ala Ile Asp Gly Ala Ser Thr Leu
 1               5                  10                  15

Arg Arg Thr Arg Phe Ala Leu Val Ser Ala Arg Ser Tyr Ala Ala Gly
                20                  25                  30

Ala Lys Glu Met Thr Val Arg Asp Ala Leu Asn Ser Ala Ile Asp Glu
            35                  40                  45

Glu Met Ser Ala Asp Pro Lys Val Phe Val Met Gly Glu Glu Val Gly
    50                  55                  60

Gln Tyr Gln Gly Ala Tyr Lys Ile Thr Lys Gly Leu Leu Glu Lys Tyr
65                  70                  75                  80

Gly Pro Glu Arg Val Tyr Asp Thr Pro Ile Thr Glu Ala Gly Phe Thr
                85                  90                  95

Gly Ile Gly Val Gly Ala Ala Tyr Ala Gly Leu Lys Pro Val Val Glu
            100                 105                 110

Phe Met Thr Phe Asn Phe Ser Met Gln Ala Ile Asp His Ile Ile Asn
        115                 120                 125

Ser Ala Ala Lys Ser Asn Tyr Met Ser Ala Gly Gln Ile Asn Val Pro
    130                 135                 140

Ile Val Phe Arg Gly Pro Asn Gly Ala Ala Gly Val Gly Ala Gln
145                 150                 155                 160

His Ser Gln Cys Tyr Ala Ala Trp Tyr Ala Ser Val Pro Gly Leu Lys
                165                 170                 175

Val Leu Ala Pro Tyr Ser Ala Glu Asp Ala Arg Gly Leu Leu Lys Ala
            180                 185                 190

Ala Ile Arg Asp Pro Asp Pro Val Val Phe Leu Glu Asn Glu Leu Leu
        195                 200                 205

Tyr Gly Glu Ser Phe Pro Ile Ser Glu Glu Ala Leu Asp Ser Ser Phe
    210                 215                 220

Cys Leu Pro Ile Gly Lys Ala Lys Ile Glu Arg Glu Gly Lys Asp Val
225                 230                 235                 240

Thr Ile Val Thr Phe Ser Lys Met Val Gly Phe Ala Leu Lys Ala Ala
                245                 250                 255

Glu Lys Leu Ala Glu Glu Gly Ile Ser Ala Glu Val Ile Asn Leu Arg
            260                 265                 270

Ser Ile Arg Pro Leu Asp Arg Ala Thr Ile Asn Ala Ser Val Arg Lys
        275                 280                 285

Thr Ser Arg Leu Val Thr Val Glu Glu Gly Phe Pro Gln His Gly Val
    290                 295                 300

Cys Ala Glu Ile Cys Ala Ser Val Val Glu Glu Ser Phe Ser Tyr Leu
305                 310                 315                 320

Asp Ala Pro Val Glu Arg Ile Ala Gly Ala Asp Val Pro Ile Pro Tyr
                325                 330                 335

Thr Ala Asn Leu Glu Arg Leu Ala Leu Pro Gln Ile Glu Asp Ile Val
            340                 345                 350

-continued

```
Arg Ala Ser Lys Arg Ala Cys Tyr Arg Ser Lys
            355                 360

<210> SEQ ID NO 45
<211> LENGTH: 359
<212> TYPE: PRT
<213> ORGANISM: H. sapiens

<400> SEQUENCE: 45

Met Ala Ala Val Ser Gly Leu Val Arg Arg Pro Leu Arg Glu Val Ser
 1               5                  10                  15

Gly Leu Leu Lys Arg Arg Phe His Trp Thr Ala Pro Ala Ala Leu Gln
                20                  25                  30

Val Thr Val Arg Asp Ala Ile Asn Gln Gly Met Asp Glu Leu Glu
             35                  40                  45

Arg Asp Glu Lys Val Phe Leu Leu Gly Glu Glu Val Ala Gln Tyr Asp
         50                  55                  60

Gly Ala Tyr Lys Val Ser Arg Gly Leu Trp Lys Lys Tyr Gly Asp Lys
 65                  70                  75                  80

Arg Ile Ile Asp Thr Pro Ile Ser Glu Met Gly Phe Ala Gly Ile Ala
                 85                  90                  95

Val Gly Ala Ala Met Ala Gly Leu Arg Pro Ile Cys Glu Phe Met Thr
            100                 105                 110

Phe Asn Phe Ser Met Gln Ala Ile Asp Gln Val Ile Asn Ser Ala Ala
        115                 120                 125

Lys Thr Tyr Tyr Met Ser Gly Gly Leu Gln Pro Val Pro Ile Val Phe
    130                 135                 140

Arg Gly Pro Asn Gly Ala Ser Ala Gly Val Ala Ala Gln His Ser Gln
145                 150                 155                 160

Cys Phe Ala Ala Trp Tyr Gly His Cys Pro Gly Leu Lys Val Val Ser
                165                 170                 175

Pro Trp Asn Ser Glu Asp Ala Lys Gly Leu Ile Lys Ser Ala Ile Arg
            180                 185                 190

Asp Asn Asn Pro Val Val Leu Glu Asn Glu Leu Met Tyr Gly Val
        195                 200                 205

Pro Phe Glu Phe Leu Pro Glu Ala Gln Ser Lys Asp Phe Leu Ile Pro
    210                 215                 220

Ile Gly Lys Ala Lys Ile Glu Arg Gln Gly Thr His Ile Thr Val Val
225                 230                 235                 240

Ser His Ser Arg Pro Val Gly His Cys Leu Glu Ala Ala Val Leu
                245                 250                 255

Ser Lys Glu Gly Val Glu Cys Glu Val Ile Asn Met Arg Thr Ile Arg
            260                 265                 270

Pro Met Asp Met Glu Thr Ile Glu Ala Ser Val Met Lys Thr Asn His
        275                 280                 285

Leu Val Thr Val Glu Gly Gly Trp Pro Gln Phe Gly Val Gly Ala Glu
    290                 295                 300

Ile Cys Ala Arg Ile Met Glu Gly Pro Ala Phe Asn Phe Leu Asp Ala
305                 310                 315                 320

Pro Ala Val Arg Val Thr Gly Ala Asp Val Pro Met Pro Tyr Ala Lys
                325                 330                 335

Ile Leu Glu Asp Asn Ser Ile Pro Gln Val Lys Asp Ile Ile Phe Ala
            340                 345                 350

Ile Lys Lys Thr Leu Asn Ile
```

355

<210> SEQ ID NO 46
<211> LENGTH: 366
<212> TYPE: PRT
<213> ORGANISM: S. cerevisiae

<400> SEQUENCE: 46

| | | | | | | | | | | | | | | |
|---|---|---|---|---|---|---|---|---|---|---|---|---|---|---|
| Met | Phe | Ser | Arg | Leu | Pro | Thr | Ser | Leu | Ala | Arg | Asn | Val | Ala | Arg | Arg |
| 1 | | | | 5 | | | | | 10 | | | | | 15 | |
| Ala | Pro | Thr | Ser | Phe | Val | Arg | Pro | Ser | Ala | Ala | Ala | Ala | Leu | Arg | |
| | | | 20 | | | | | 25 | | | | | 30 | | |
| Phe | Ser | Ser | Thr | Lys | Thr | Met | Thr | Val | Arg | Glu | Ala | Leu | Asn | Ser | Ala |
| | | 35 | | | | | 40 | | | | | 45 | | | |
| Met | Ala | Glu | Glu | Leu | Asp | Arg | Asp | Asp | Val | Phe | Leu | Ile | Gly | Glu | |
| 50 | | | | | 55 | | | | | 60 | | | | | |
| Glu | Val | Ala | Gln | Tyr | Asn | Gly | Ala | Tyr | Lys | Val | Ser | Lys | Gly | Leu | Leu |
| 65 | | | | | 70 | | | | | 75 | | | | | 80 |
| Asp | Arg | Phe | Gly | Glu | Arg | Arg | Val | Val | Asp | Thr | Pro | Ile | Thr | Glu | Tyr |
| | | | | 85 | | | | | 90 | | | | | 95 | |
| Gly | Phe | Thr | Gly | Leu | Ala | Val | Gly | Ala | Ala | Leu | Lys | Gly | Leu | Lys | Pro |
| | | | 100 | | | | | 105 | | | | | 110 | | |
| Ile | Val | Glu | Phe | Met | Ser | Phe | Asn | Phe | Ser | Met | Gln | Ala | Ile | Asp | His |
| | | 115 | | | | | 120 | | | | | 125 | | | |
| Val | Val | Asn | Ser | Ala | Ala | Lys | Thr | His | Tyr | Met | Ser | Gly | Gly | Thr | Gln |
| 130 | | | | | 135 | | | | | 140 | | | | | |
| Lys | Cys | Gln | Met | Val | Phe | Arg | Gly | Pro | Asn | Gly | Ala | Ala | Val | Gly | Leu |
| 145 | | | | 150 | | | | | 155 | | | | | 160 | |
| Gly | Ala | Gln | His | Ser | Gln | Asp | Phe | Ser | Pro | Trp | Tyr | Gly | Ser | Ile | Pro |
| | | | | 165 | | | | | 170 | | | | | 175 | |
| Gly | Leu | Lys | Val | Leu | Val | Pro | Tyr | Ser | Ala | Glu | Asp | Ala | Arg | Gly | Leu |
| | | | 180 | | | | | 185 | | | | | 190 | | |
| Leu | Lys | Ala | Ala | Ile | Arg | Asp | Pro | Asn | Pro | Val | Val | Phe | Leu | Glu | Asn |
| | | 195 | | | | | 200 | | | | | 205 | | | |
| Glu | Leu | Leu | Tyr | Gly | Glu | Ser | Phe | Glu | Ile | Ser | Glu | Glu | Ala | Leu | Ser |
| 210 | | | | | 215 | | | | | 220 | | | | | |
| Pro | Glu | Phe | Thr | Leu | Pro | Tyr | Lys | Ala | Lys | Ile | Glu | Arg | Glu | Gly | Thr |
| 225 | | | | 230 | | | | | 235 | | | | | 240 | |
| Asp | Ile | Ser | Ile | Val | Thr | Tyr | Thr | Arg | Asn | Val | Gln | Phe | Ser | Leu | Glu |
| | | | | 245 | | | | | 250 | | | | | 255 | |
| Ala | Ala | Glu | Ile | Leu | Gln | Lys | Lys | Tyr | Gly | Val | Ser | Ala | Glu | Val | Ile |
| | | | 260 | | | | | 265 | | | | | 270 | | |
| Asn | Leu | Arg | Ser | Ile | Arg | Pro | Leu | Asp | Thr | Glu | Ala | Ile | Ile | Lys | Thr |
| | | 275 | | | | | 280 | | | | | 285 | | | |
| Val | Lys | Lys | Thr | Asn | His | Leu | Ile | Thr | Val | Glu | Ser | Thr | Phe | Pro | Ser |
| 290 | | | | | 295 | | | | | 300 | | | | | |
| Phe | Gly | Val | Gly | Ala | Glu | Ile | Val | Ala | Gln | Val | Met | Glu | Ser | Glu | Ala |
| 305 | | | | 310 | | | | | 315 | | | | | 320 | |
| Phe | Asp | Tyr | Leu | Asp | Ala | Pro | Ile | Gln | Arg | Val | Thr | Gly | Ala | Asp | Val |
| | | | | 325 | | | | | 330 | | | | | 335 | |
| Pro | Thr | Pro | Tyr | Ala | Lys | Glu | Leu | Glu | Asp | Phe | Ala | Phe | Pro | Asp | Thr |
| | | | 340 | | | | | 345 | | | | | 350 | | |
| Pro | Thr | Ile | Val | Lys | Ala | Val | Lys | Glu | Val | Leu | Ser | Ile | Glu | | |
| | | 355 | | | | | 360 | | | | | 365 | | | |

-continued

```
<210> SEQ ID NO 47
<211> LENGTH: 361
<212> TYPE: PRT
<213> ORGANISM: A. suum

<400> SEQUENCE: 47
```

Met Ala Val Asn Gly Cys Met Arg Leu Leu Arg Asn Gly Leu Thr Ser
 1               5                  10                  15

Ala Cys Ala Leu Glu Gln Ser Val Arg Arg Leu Ala Ser Gly Thr Leu
                20                  25                  30

Asn Val Thr Val Arg Asp Ala Leu Asn Ala Ala Leu Asp Glu Glu Ile
            35                  40                  45

Lys Arg Asp Asp Arg Val Phe Leu Ile Gly Glu Glu Val Ala Gln Tyr
        50                  55                  60

Asp Gly Ala Tyr Lys Ile Ser Lys Gly Leu Trp Lys Lys Tyr Gly Asp
65                  70                  75                  80

Gly Arg Ile Trp Asp Thr Pro Ile Thr Glu Met Ala Ile Ala Gly Leu
                85                  90                  95

Ser Val Gly Ala Ala Met Asn Gly Leu Arg Pro Ile Cys Glu Phe Met
            100                 105                 110

Ser Met Asn Phe Ser Met Gln Gly Ile Asp His Ile Ile Asn Ser Ala
        115                 120                 125

Ala Lys Ala His Tyr Met Ser Ala Gly Arg Phe His Val Pro Ile Val
    130                 135                 140

Phe Arg Gly Ala Asn Gly Ala Ala Val Gly Val Ala Gln His Gln Ser
145                 150                 155                 160

Gln Asp Phe Thr Ala Trp Phe Met His Cys Pro Gly Val Lys Val Val
                165                 170                 175

Val Pro Tyr Asp Cys Glu Asp Ala Arg Gly Leu Leu Lys Ala Ala Val
            180                 185                 190

Arg Asp Asp Asn Pro Val Ile Cys Leu Glu Asn Glu Ile Leu Tyr Gly
        195                 200                 205

Met Lys Phe Pro Val Ser Pro Glu Ala Gln Ser Pro Asp Phe Val Leu
    210                 215                 220

Pro Phe Gly Gln Ala Lys Ile Gln Arg Pro Gly Lys Asp Ile Thr Ile
225                 230                 235                 240

Val Ser Leu Ser Ile Gly Val Asp Val Ser Leu His Ala Ala Asp Glu
                245                 250                 255

Leu Ala Lys Ser Gly Ile Asp Cys Glu Val Ile Asn Leu Arg Cys Val
            260                 265                 270

Arg Pro Leu Asp Phe Gln Thr Val Lys Asp Ser Val Ile Lys Thr Lys
        275                 280                 285

His Leu Val Thr Val Glu Ser Gly Trp Pro Asn Cys Gly Val Gly Ala
    290                 295                 300

Glu Ile Ser Ala Arg Val Thr Glu Ser Asp Ala Phe Gly Tyr Leu Asp
305                 310                 315                 320

Gly Pro Ile Leu Arg Val Thr Gly Val Asp Val Pro Met Pro Tyr Ala
                325                 330                 335

Gln Pro Leu Glu Thr Ala Ala Leu Pro Gln Pro Ala Asp Val Val Lys
            340                 345                 350

Met Val Lys Lys Cys Leu Asn Val Gln
        355                 360

```
<210> SEQ ID NO 48
```

-continued

<211> LENGTH: 329
<212> TYPE: PRT
<213> ORGANISM: M. capricolm

<400> SEQUENCE: 48

```
Met Ala Ile Ile Asn Asn Ile Lys Ala Val Thr Asp Ala Leu Asp Cys
  1               5                  10                  15

Ala Met Gln Arg Asp Pro Asn Val Ile Val Phe Gly Glu Asp Val Gly
             20                  25                  30

Thr Glu Gly Gly Val Phe Arg Ala Thr Gln Gly Leu Ala Val Lys Phe
         35                  40                  45

Gly Asn Asp Arg Cys Phe Asn Ala Pro Ile Ser Glu Ala Met Phe Ala
     50                  55                  60

Gly Val Gly Leu Gly Met Ala Met Asn Gly Met Lys Pro Val Leu Glu
 65                  70                  75                  80

Met Gln Phe Glu Gly Leu Gly Leu Ala Ser Leu Gln Asn Ile Phe Thr
                 85                  90                  95

Asn Ile Ser Arg Met Arg Asn Arg Thr Arg Gly Lys Tyr Thr Ala Pro
            100                 105                 110

Met Val Ile Arg Met Pro Met Gly Gly Gly Ile Arg Ala Leu Glu His
        115                 120                 125

His Ser Glu Ala Leu Glu Ala Val Tyr Ala His Ile Pro Gly Val Gln
    130                 135                 140

Ile Val Cys Pro Ser Thr Pro Tyr Asp Thr Lys Gly Leu Ile Leu Ala
145                 150                 155                 160

Ala Ile Asp Ser Pro Asp Pro Val Ile Val Val Glu Pro Thr Lys Leu
                165                 170                 175

Tyr Arg Ala Phe Lys Gln Glu Val Pro Asp Glu His Tyr Ile Val Pro
            180                 185                 190

Ile Gly Glu Gly Tyr Lys Ile Gln Glu Gly Asn Asp Leu Thr Val Val
        195                 200                 205

Thr Tyr Gly Ala Gln Thr Val Asp Cys Gln Lys Ala Ile Ala Leu Leu
    210                 215                 220

Lys Glu Thr His Pro Asn Ala Thr Ile Asp Leu Ile Asp Leu Arg Ser
225                 230                 235                 240

Ile Lys Pro Trp Asp Lys Lys Met Val Ile Glu Ser Val Lys Lys Thr
                245                 250                 255

Gly Arg Leu Leu Val Val His Glu Ala Val Lys Ser Phe Ser Val Ser
            260                 265                 270

Ala Glu Ile Ile Ala Thr Val Asn Glu Glu Cys Phe Glu Tyr Ile Lys
        275                 280                 285

Ala Pro Leu Ser Arg Cys Thr Gly Tyr Asp Val Ile Thr Pro Phe Asp
    290                 295                 300

Arg Gly Glu Gly Tyr Phe Gln Val Asn Pro Lys Lys Val Leu Val Lys
305                 310                 315                 320

Met Gln Glu Leu Leu Asp Phe Lys Phe
                325
```

<210> SEQ ID NO 49
<211> LENGTH: 325
<212> TYPE: PRT
<213> ORGANISM: B. subtilis

<400> SEQUENCE: 49

```
Met Ala Gln Met Thr Met Val Gln Ala Ile Thr Asp Ala Leu Arg Ile
  1               5                  10                  15
```

Glu Leu Lys Asn Asp Pro Asn Val Leu Ile Phe Gly Glu Asp Val Gly
             20                  25                  30

Val Asn Gly Gly Val Phe Arg Ala Thr Glu Gly Leu Gln Ala Glu Phe
         35                  40                  45

Gly Glu Asp Arg Val Phe Asp Thr Pro Leu Ala Glu Ser Gly Ile Gly
     50                  55                  60

Gly Leu Ala Ile Gly Leu Ala Leu Gln Gly Phe Arg Pro Val Pro Glu
 65                  70                  75                  80

Ile Gln Phe Phe Gly Phe Val Tyr Glu Val Met Asp Ser Ile Cys Gly
                 85                  90                  95

Gln Met Ala Arg Ile Arg Tyr Arg Thr Gly Gly Arg Tyr His Met Pro
             100                 105                 110

Ile Thr Ile Arg Ser Pro Phe Gly Gly Val His Thr Pro Glu Leu
         115                 120                 125

His Ser Asp Ser Leu Glu Gly Leu Val Ala Gln Gln Pro Gly Leu Lys
     130                 135                 140

Val Val Ile Pro Ser Thr Pro Tyr Asp Ala Lys Gly Leu Leu Ile Ser
145                 150                 155                 160

Ala Ile Arg Asp Asn Asp Pro Val Ile Phe Leu Glu His Leu Lys Leu
                 165                 170                 175

Tyr Arg Ser Phe Arg Gln Glu Val Pro Glu Gly Glu Tyr Thr Ile Pro
             180                 185                 190

Ile Gly Lys Ala Asp Ile Lys Arg Glu Gly Lys Asp Ile Thr Ile Ile
         195                 200                 205

Ala Tyr Gly Ala Met Val His Glu Ser Leu Lys Ala Ala Ala Glu Leu
     210                 215                 220

Glu Lys Glu Gly Ile Ser Ala Glu Val Val Asp Leu Arg Thr Val Gln
225                 230                 235                 240

Pro Leu Asp Ile Glu Thr Ile Ile Gly Ser Val Glu Lys Thr Gly Arg
                 245                 250                 255

Ala Ile Val Val Gln Glu Ala Gln Arg Gln Ala Gly Ile Ala Ala Asn
             260                 265                 270

Val Val Ala Glu Ile Asn Glu Arg Ala Ile Leu Ser Leu Glu Ala Pro
         275                 280                 285

Val Leu Arg Val Ala Ala Pro Asp Thr Val Tyr Pro Phe Ala Gln Ala
     290                 295                 300

Glu Ser Val Trp Leu Pro Asn Phe Lys Asp Val Ile Glu Thr Ala Lys
305                 310                 315                 320

Lys Val Met Asn Phe
                325

<210> SEQ ID NO 50
<211> LENGTH: 162
<212> TYPE: PRT
<213> ORGANISM: Artificial Sequence
<220> FEATURE:
<223> OTHER INFORMATION: Description of Artificial Sequence: consensus

<400> SEQUENCE: 50

Thr Ala Leu Ala Asp Glu Glu Arg Asp Val Gly Glu Val Gly Tyr Gly
  1               5                  10                  15

Tyr Lys Thr Lys Gly Leu Lys Gly Arg Val Asp Thr Pro Ile Glu Phe
             20                  25                  30

Gly Gly Ala Ala Gly Leu Arg Pro Glu Met Phe Ala Asp Ile Asn Ala
         35                  40                  45

```
Ala Tyr Ser Gly Gly Pro Val Arg Gly Pro Gly Ala His Ser Gln Ala
         50                  55                  60

Pro Gly Leu Lys Val Val Pro Asp Ala Lys Gly Leu Leu Lys Ala Ala
 65                  70                  75                  80

Ile Arg Asp Asn Pro Val Leu Glu Leu Leu Tyr Glu Pro Gly Lys Ala
                 85                  90                  95

Ile Arg Gly Asp Ile Thr Ile Val Thr Tyr Ser Val Leu Ala Ala Leu
                100                 105                 110

Gly Glu Val Ile Leu Arg Ser Pro Leu Asp Thr Ile Ser Val Lys Thr
            115                 120                 125

Arg Leu Val Glu Glu Gly Val Gly Ala Glu Ile Ala Glu Phe Tyr Leu
130                 135                 140

Asp Ala Pro Arg Gly Asp Val Pro Pro Tyr Ala Leu Glu Pro Gln Ile
145                 150                 155                 160

Ala Lys

<210> SEQ ID NO 51
<211> LENGTH: 352
<212> TYPE: PRT
<213> ORGANISM: Arabidopsis thaliana

<400> SEQUENCE: 51

Met Ala Ala Leu Leu Gly Arg Ser Cys Arg Lys Leu Ser Phe Pro Ser
  1               5                  10                  15

Leu Thr His Gly Ala Arg Arg Val Ser Thr Glu Thr Gly Lys Pro Leu
                 20                  25                  30

Asn Leu Tyr Ser Ala Ile Asn Gln Ala Leu His Ile Ala Leu Asp Thr
             35                  40                  45

Asp Pro Arg Ser Tyr Val Phe Gly Glu Asp Val Gly Phe Gly Gly Val
         50                  55                  60

Phe Arg Cys Thr Thr Gly Leu Ala Glu Arg Phe Gly Lys Asn Arg Val
 65                  70                  75                  80

Phe Asn Thr Pro Leu Cys Glu Gln Gly Ile Val Gly Phe Gly Ile Gly
                 85                  90                  95

Leu Ala Ala Met Gly Asn Arg Ala Ile Val Glu Ile Gln Phe Ala Asp
                100                 105                 110

Tyr Ile Tyr Pro Ala Phe Asp Gln Ile Val Asn Glu Ala Ala Lys Phe
            115                 120                 125

Arg Tyr Arg Ser Gly Asn Gln Phe Asn Cys Gly Gly Leu Thr Ile Arg
130                 135                 140

Ala Pro Tyr Gly Ala Val Gly His Gly Gly His Tyr His Ser Gln Ser
145                 150                 155                 160

Pro Glu Ala Phe Phe Cys His Val Pro Gly Ile Lys Val Val Ile Pro
                165                 170                 175

Arg Ser Pro Arg Glu Ala Lys Gly Leu Leu Leu Ser Cys Ile Arg Asp
            180                 185                 190

Pro Asn Pro Val Val Phe Phe Glu Pro Lys Trp Leu Tyr Arg Gln Ala
        195                 200                 205

Val Glu Glu Val Pro Glu His Asp Tyr Met Ile Pro Leu Ser Glu Ala
210                 215                 220

Glu Val Ile Arg Glu Gly Asn Asp Ile Thr Leu Val Gly Trp Gly Ala
225                 230                 235                 240

Gln Leu Thr Val Met Glu Gln Ala Cys Leu Asp Ala Glu Lys Glu Gly
                245                 250                 255
```

```
Ile Ser Cys Glu Leu Ile Asp Leu Lys Thr Leu Leu Pro Trp Asp Lys
            260                 265                 270

Glu Thr Val Glu Ala Ser Val Lys Lys Thr Gly Arg Leu Leu Ile Ser
        275                 280                 285

His Glu Ala Pro Val Thr Gly Gly Phe Gly Ala Glu Ile Ser Ala Thr
    290                 295                 300

Ile Leu Glu Arg Cys Phe Leu Lys Leu Glu Ala Pro Val Ser Arg Val
305                 310                 315                 320

Cys Gly Leu Asp Thr Pro Phe Pro Leu Val Phe Glu Pro Phe Tyr Met
                325                 330                 335

Pro Thr Lys Asn Lys Ile Leu Asp Ala Ile Lys Ser Thr Val Asn Tyr
            340                 345                 350

<210> SEQ ID NO 52
<211> LENGTH: 392
<212> TYPE: PRT
<213> ORGANISM: Human

<400> SEQUENCE: 52

Met Ala Val Val Ala Ala Ala Gly Trp Leu Leu Arg Leu Arg Ala
1               5                   10                  15

Ala Gly Ala Glu Gly His Trp Arg Arg Leu Pro Gly Ala Gly Leu Ala
            20                  25                  30

Arg Gly Phe Leu His Pro Ala Ala Thr Val Glu Asp Ala Ala Gln Arg
        35                  40                  45

Arg Gln Val Ala His Phe Thr Phe Gln Pro Asp Pro Glu Pro Arg Glu
    50                  55                  60

Tyr Gly Gln Thr Gln Lys Met Asn Leu Phe Gln Ser Val Thr Ser Ala
65                  70                  75                  80

Leu Asp Asn Ser Leu Ala Lys Asp Pro Thr Ala Val Ile Phe Gly Glu
                85                  90                  95

Asp Val Ala Phe Gly Gly Val Phe Arg Cys Thr Val Gly Leu Arg Asp
            100                 105                 110

Lys Tyr Gly Lys Asp Arg Val Phe Asn Thr Pro Leu Cys Glu Gln Gly
        115                 120                 125

Ile Val Gly Phe Gly Ile Gly Ile Ala Val Thr Gly Ala Thr Ala Ile
    130                 135                 140

Ala Glu Ile Gln Phe Ala Asp Tyr Ile Phe Pro Ala Phe Asp Gln Ile
145                 150                 155                 160

Val Asn Glu Ala Ala Lys Tyr Arg Tyr Arg Ser Gly Asp Leu Phe Asn
                165                 170                 175

Cys Gly Ser Leu Thr Ile Arg Ser Pro Trp Gly Cys Val Gly His Gly
            180                 185                 190

Ala Leu Tyr His Ser Gln Ser Pro Glu Ala Phe Phe Ala His Cys Pro
        195                 200                 205

Gly Ile Lys Val Val Ile Pro Arg Ser Pro Phe Gln Ala Lys Gly Leu
    210                 215                 220

Leu Leu Ser Cys Ile Glu Asp Lys Asn Pro Cys Ile Phe Phe Glu Pro
225                 230                 235                 240

Lys Ile Leu Tyr Arg Ala Ala Ala Glu Glu Val Pro Ile Glu Pro Tyr
                245                 250                 255

Asn Ile Pro Leu Ser Gln Ala Glu Val Ile Gln Glu Gly Ser Asp Val
            260                 265                 270

Thr Leu Val Ala Trp Gly Thr Gln Val His Val Ile Arg Glu Val Ala
```

```
            275                 280                 285
Ser Met Ala Lys Glu Lys Leu Gly Val Ser Cys Glu Val Ile Asp Leu
    290                 295                 300

Arg Thr Ile Ile Pro Trp Asp Val Asp Thr Ile Cys Lys Ser Val Ile
305                 310                 315                 320

Lys Ser Gly Arg Leu Leu Ile Ser His Glu Ala Pro Leu Thr Gly Gly
                325                 330                 335

Phe Ala Ser Glu Ile Ser Ser Thr Val Gln Glu Glu Cys Phe Leu Asn
            340                 345                 350

Leu Glu Ala Pro Ile Ser Arg Val Cys Gly Tyr Asp Thr Pro Phe Pro
            355                 360                 365

His Ile Phe Glu Pro Phe Tyr Ile Pro Asp Lys Trp Lys Cys Tyr Asp
    370                 375                 380

Ala Leu Arg Lys Met Ile Asn Tyr
385                 390

<210> SEQ ID NO 53
<211> LENGTH: 391
<212> TYPE: PRT
<213> ORGANISM: Bovine

<400> SEQUENCE: 53

Met Ala Ala Val Ala Ala Phe Ala Gly Trp Leu Leu Arg Leu Arg Ala
  1               5                  10                  15

Ala Gly Ala Asp Gly Pro Trp Arg Arg Leu Cys Gly Ala Gly Leu Ser
                20                  25                  30

Arg Gly Phe Leu Gln Ser Ala Ser Ala Tyr Gly Ala Ala Gln Arg Arg
            35                  40                  45

Gln Val Ala His Phe Thr Phe Gln Pro Asp Pro Glu Pro Val Glu Tyr
        50                  55                  60

Gly Gln Thr Gln Lys Met Asn Leu Phe Gln Ala Val Thr Ser Ala Leu
 65                  70                  75                  80

Asp Asn Ser Leu Ala Lys Asp Pro Thr Ala Val Ile Phe Gly Glu Asp
                85                  90                  95

Val Ala Phe Gly Gly Val Phe Arg Cys Thr Val Gly Leu Arg Asp Lys
                100                 105                 110

Tyr Gly Lys Asp Arg Val Phe Asn Thr Pro Leu Cys Glu Gln Gly Ile
            115                 120                 125

Val Gly Phe Gly Ile Gly Ile Ala Val Thr Gly Ala Thr Ala Ile Ala
        130                 135                 140

Glu Ile Gln Phe Ala Asp Tyr Ile Phe Pro Ala Phe Asp Gln Ile Val
145                 150                 155                 160

Asn Glu Ala Ala Lys Tyr Arg Tyr Arg Ser Gly Asp Leu Phe Asn Cys
                165                 170                 175

Gly Ser Leu Thr Ile Arg Ser Pro Trp Gly Cys Val Gly His Gly Ala
            180                 185                 190

Leu Tyr His Ser Gln Ser Pro Glu Ala Phe Phe Ala His Cys Pro Gly
        195                 200                 205

Ile Lys Val Val Pro Arg Ser Pro Phe Gln Ala Lys Gly Leu Leu
    210                 215                 220

Leu Ser Cys Ile Glu Asp Lys Asn Pro Cys Ile Phe Phe Glu Pro Lys
225                 230                 235                 240

Ile Leu Tyr Arg Ala Ala Val Glu Gln Val Pro Val Glu Pro Tyr Asn
                245                 250                 255
```

-continued

Ile Pro Leu Ser Gln Ala Glu Val Ile Gln Glu Gly Ser Asp Val Thr
            260                 265                 270

Leu Val Ala Trp Gly Thr Gln Val His Glu Ile Arg Glu Val Ala Ala
            275                 280                 285

Met Ala Gln Glu Lys Leu Gly Val Ser Cys Glu Val Ile Asp Leu Arg
            290                 295                 300

Thr Ile Leu Pro Trp Asp Val Asp Thr Val Cys Lys Ser Val Ile Lys
305                 310                 315                 320

Thr Gly Arg Leu Leu Val Ser His Glu Ala Pro Leu Thr Gly Gly Phe
            325                 330                 335

Ala Ser Glu Ile Ser Ser Thr Val Gln Glu Gln Cys Phe Leu Asn Leu
            340                 345                 350

Glu Ala Pro Ile Ser Arg Val Cys Gly Tyr Asp Thr Pro Phe Pro His
            355                 360                 365

Ile Phe Glu Pro Phe Tyr Ile Pro Asp Lys Trp Lys Cys Tyr Asp Ala
370                 375                 380

Leu Arg Lys Met Ile Asn Tyr
385                 390

<210> SEQ ID NO 54
<211> LENGTH: 375
<212> TYPE: PRT
<213> ORGANISM: Artificial Sequence
<220> FEATURE:
<223> OTHER INFORMATION: Description of Artificial Sequence: consensus

<400> SEQUENCE: 54

Met Ala Ala Val Ala Ala Gly Trp Leu Leu Arg Leu Arg Ala Ala
1               5                   10                  15

Gly Ala Gly Trp Arg Arg Leu Gly Ala Gly Leu Arg Gly Phe Leu Ala
                20                  25                  30

Ala Ala Gln Arg Arg Gln Val Ala His Phe Thr Phe Gln Pro Asp Pro
            35                  40                  45

Glu Pro Glu Tyr Gly Gln Thr Gln Lys Met Asn Leu Phe Gln Ala Val
        50                  55                  60

Thr Ser Ala Leu Asp Asn Ser Leu Ala Lys Asp Pro Thr Ala Val Ile
65                  70                  75                  80

Phe Gly Glu Asp Val Ala Phe Gly Gly Val Phe Arg Cys Thr Val Gly
                85                  90                  95

Leu Arg Asp Lys Tyr Gly Lys Asp Arg Val Phe Asn Thr Pro Leu Cys
            100                 105                 110

Glu Gln Gly Ile Val Gly Phe Gly Ile Gly Ile Ala Val Thr Gly Ala
            115                 120                 125

Thr Ala Ile Ala Glu Ile Gln Phe Ala Asp Tyr Ile Phe Pro Ala Phe
130                 135                 140

Asp Gln Ile Val Asn Glu Ala Ala Lys Tyr Arg Tyr Arg Ser Gly Asp
145                 150                 155                 160

Leu Phe Asn Cys Gly Ser Leu Thr Ile Arg Ser Pro Trp Gly Cys Val
            165                 170                 175

Gly His Gly Ala Leu Tyr His Ser Gln Ser Pro Glu Ala Phe Phe Ala
            180                 185                 190

His Cys Pro Gly Ile Lys Val Val Ile Pro Arg Ser Pro Phe Gln Ala
            195                 200                 205

Lys Gly Leu Leu Leu Ser Cys Ile Glu Asp Lys Asn Pro Cys Ile Phe
            210                 215                 220

```
Phe Glu Pro Lys Ile Leu Tyr Arg Ala Ala Val Glu Glu Val Pro Glu
225                 230                 235                 240

Pro Tyr Asn Ile Pro Leu Ser Gln Ala Glu Val Ile Gln Glu Gly Ser
                245                 250                 255

Asp Val Thr Leu Val Ala Trp Gly Thr Gln Val His Val Ile Arg Glu
            260                 265                 270

Val Ala Met Ala Glu Lys Leu Gly Val Ser Cys Glu Val Ile Asp Leu
        275                 280                 285

Arg Thr Ile Leu Pro Trp Asp Val Asp Thr Val Cys Lys Ser Val Ile
        290                 295                 300

Lys Thr Gly Arg Leu Leu Ile Ser His Glu Ala Pro Leu Thr Gly Gly
305                 310                 315                 320

Phe Ala Ser Glu Ile Ser Ser Thr Val Gln Glu Cys Phe Leu Asn Leu
                325                 330                 335

Glu Ala Pro Ile Ser Arg Val Cys Gly Tyr Asp Thr Pro Phe Pro His
            340                 345                 350

Ile Phe Glu Pro Phe Tyr Ile Pro Asp Lys Trp Lys Cys Tyr Asp Ala
            355                 360                 365

Leu Arg Lys Met Ile Asn Tyr
370                 375
```